United States Patent
Bruce et al.

(10) Patent No.: US 8,268,834 B2
(45) Date of Patent: Sep. 18, 2012

(54) PYRAZINE DERIVATIVES THAT INHIBIT PHOSPHATIDYLINOSITOL 3-KINASE ENZYME

(75) Inventors: Ian Bruce, Horsham (GB); Emma Budd, Horsham (GB); Lee Edwards, Horsham (GB); Catherine Howsham, Horsham (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/380,901

(22) Filed: Mar. 4, 2009

(65) Prior Publication Data
US 2009/0239847 A1   Sep. 24, 2009

(30) Foreign Application Priority Data
Mar. 19, 2008 (EP) .................................... 08153045

(51) Int. Cl.
A61K 31/4965 (2006.01)
(52) U.S. Cl. .............. 514/255.06; 540/575; 544/105; 544/120; 544/359; 544/407; 546/210; 546/268.1; 548/373.1; 548/469; 548/518; 549/398; 549/505
(58) Field of Classification Search ............. 514/255.06; 540/575; 544/105, 120, 359, 407; 546/210, 546/268.1; 548/373.1, 469, 518; 549/398, 549/505
See application file for complete search history.

(56) References Cited

U.S. PATENT DOCUMENTS

| | | | |
|---|---|---|---|
| 2005/0009840 A1* | 1/2005 | Cui et al. ................. | 514/255.05 |
| 2005/0234101 A1* | 10/2005 | Stenkamp et al. ........... | 514/318 |
| 2006/0030583 A1 | 2/2006 | Arnold et al. | |
| 2009/0163463 A1 | 6/2009 | Bruce et al. | |

FOREIGN PATENT DOCUMENTS

| | | |
|---|---|---|
| DE | 2 051 013 | 12/1971 |
| GB | 2 073 185 | 10/1981 |
| WO | WO 97/43267 | 11/1997 |
| WO | WO 01/46691 | 6/2001 |
| WO | WO 03/093297 | 11/2003 |
| WO | WO 2004/048365 | 6/2004 |
| WO | WO 2004/076412 | 9/2004 |
| WO | WO 2004/085409 | 10/2004 |
| WO | WO 2006/021881 | 3/2006 |
| WO | WO 2006/021886 | 3/2006 |
| WO | WO 2006/051270 | 5/2006 |
| WO | WO 2007/095588 | 8/2007 |
| WO | WO 2008/012326 | 1/2008 |
| WO | WO 2008/038955 | 4/2008 |
| WO | WO 2008/053157 | 5/2008 |
| WO | WO 2008/094992 | 8/2008 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
V. Hagen et al., "Potentiell Kardiotonika" Pharmazie 47(10):767-769, Jan. 2009.
Nobuhiro Sato, "Studies on Pyrazines . . . " Journal of Heterocyclic Chemistry 15(4):665-670, Jun. 1978.
Tokuhiro Watanabe et al., "A Convenient Synthesis of Methylamino and Dimethylamino Subsituted Aromatic Compounds" Synthesis 1:39-41, Jan. 1980.
Katsunori Teranishi and Toshio Goto, "Synthesis and Chemiluminescence of Coelenterazine (Oplophorus Luciferin) Analogues" Bull. Chem. Soc. Jpm. 63(11):3132-3140, 1999.
Keith Jones et al., "A Suzuki Coupling Approach to Pyrazines Related to Coelenterazine" Synlett 6:509-510, Jun. 1996.
Martine Keenan et al., "Highly Efficient and Flexible Total Synthesis of Coelenterazine" Chem. Commun., pp. 323-324, 1997.
Gregory Bennett et al., "Synthesis and Antiinflammatory Activity of Trisubstituted Pyrimidines and Triazines" *Journal Medicinal Chemist* 21 (7):623-628, 1978.

* cited by examiner

*Primary Examiner* — Douglas M Willis
(74) *Attorney, Agent, or Firm* — Michael G. Smith

(57) ABSTRACT

The present invention concerns a compound of formula (I)

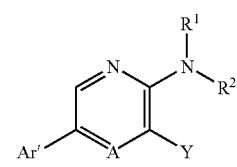

or a salt, suitably a pharmaceutically acceptable salt, or solvate thereof, wherein the groups $R^1$, $R^2$, Ar', A and Y are defined in the description, to compositions and use of the compounds in the treatment of inflammatory and allergic conditions.

6 Claims, No Drawings

PYRAZINE DERIVATIVES THAT INHIBIT PHOSPHATIDYLINOSITOL 3-KINASE ENZYME

This application claims benefit under 35 U.S.C. §119(a-d) or (f) or 356(b) of European Patent Application No. 08153045.3, filed Mar. 19, 2008, the contents of which are incorporated herein by reference in their entirety.

The present invention relates to organic compounds, their preparation and their use as pharmaceuticals.

In a first aspect, the present invention provides compounds of formula I:

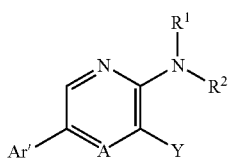

or a salt or solvate thereof, wherein:

$R^1$ and $R^2$ are each independently selected from hydrogen, $C_1$-$C_6$ alkyl, $C_3$-$C_8$ cycloalkyl, $C_1$-$C_3$ alkyl-$C_3$-$C_8$ cycloalkyl, $C_1$-$C_3$ alkyl-$C_1$-$C_6$ alkoxy and $(CH_2)_m$ heterocyclyl; or $R^1$ and $R^2$, together with the nitrogen atom to which they are attached form a 5- or 6-membered nitrogen-containing heterocyclic group;

m is independently selected from 0, 1 and 2;

Y is selected from hydrogen, —$OC_1$-$C_6$ alkyl, —$OC_3$-$C_8$ cycloalkyl, —$OC_1$-$C_3$ alkyl-$C_3$-$C_8$ cycloalkyl, —$O(CH_2)_a$ aryl, —$O(CH_2)_b$ heteroaryl, —$C(O)C_1$-$C_6$ alkyl, —$C(O)C_3$-$C_8$ cycloalkyl, —$C(O)C_1$-$C_3$ alkyl-$C_3$-$C_8$ cycloalkyl, —$C(O)$ aryl, —$C(O)$heteroaryl and $NR^3R^4$, where the ring systems are each optionally substituted by one or more substituents selected from List X;

$R^3$ is selected from hydrogen, $C_1$-$C_6$ alkyl, $C_3$-$C_8$ cycloalkyl and $C_1$-$C_3$ alkyl-$C_3$-$C_8$ cycloalkyl;

$R^4$ is selected from hydrogen, $C_1$-$C_6$ alkyl, aryl and heteroaryl, where the alkyl group is optionally substituted by halo, OH and $C_1$-$C_3$ alkoxy, and the aryl and heteroaryl groups are each optionally substituted by one or more substituents selected from List X;

a and b are each independently 0, 1, 2 or 3;

A is N or $CR^5$;

$R^5$ is selected from hydrogen, $C_1$-$C_6$ alkyl, $C_1$-$C_6$ haloalkyl, $C_3$-$C_8$ cycloalkyl, $C_1$-$C_3$ alkyl-$C_3$-$C_8$ cycloalkyl, $C_3$-$C_8$ cycloalkenyl, aryl, heterocyclyl and a group -Q-Z, where the alkyl groups and the ring systems are each optionally substituted by one or more substituents selected from list X;

Q is —O—$(CH_2)_n$— or —$N(R^6)$—$(CH_2)_o$—;

Z is $C_3$-$C_8$ cycloalkyl, $C_3$-$C_8$ cycloalkenyl, aryl or heterocyclyl, where the ring systems are each optionally substituted by one or more substituents selected from list X;

$R^6$ is hydrogen, $C_1$-$C_6$ alkyl, $C_3$-$C_8$ cycloalkyl or $C_1$-$C_3$ alkyl-$C_3$-$C_8$ cycloalkyl;

n and o are each independently 0, 1 or 2;

Ar' is aryl or heteroaryl, where each of the aryl and heteroaryl groups are optionally substituted by one or more substituents selected from List X;

List X is represented by hydroxyl, halo, cyano, nitro, $C_1$-$C_6$-alkyl, $C_2$-$C_6$-alkenyl, $C_2$-$C_6$-alkynyl, $C_3$-$C_8$ cycloalkyl, $C_1$-$C_3$ alkyl-$C_3$-$C_8$ cycloalkyl, —$OC_1$-$C_6$-alkyl, —$OC_2$-$C_6$-alkenyl, —$OC_2$-$C_6$-alkynyl, —$OC_3$-$C_8$ cycloalkyl, —$OC_1$-$C_3$ alkyl-$C_3$-$C_8$ cycloalkyl, —$(O)_p$—$(C_1$-$C_4$-alkylene)-$R^7$, —$C(O)H$, $C(O)OH$, $C(O)C_1$-$C_6$-alkyl, $C(O)C_3$-$C_8$ cycloalkyl, $C(O)C_1$-$C_3$ alkyl-$C_3$-$C_8$ cycloalkyl, $C(O)$heterocyclyl, $C(O)$aryl, $C(O)OC_1$-$C_6$-alkyl, $C(O)OC_3$-$C_8$ cycloalkyl, $C(O)OC_1$-$C_3$ alkyl-$C_3$-$C_8$ cycloalkyl, $NR^8R^9$, $C(O)NR^{10}R^{11}$, $(CH_2)_zNR^{13}SO_2R^{14}$, —$SC_1$-$C_6$-alkyl, —$S(O)C_1$-$C_6$-alkyl, $SO_2R^{15}$, oxo, heterocyclyl and aryl, where each of the hydrocarbon groups are optionally substituted by one or more halogen, hydroxyl, —$OC_1$-$C_6$-alkyl, phenyl, $NR^{16}R^{17}$ or cyano substituents, and where the aryl and heterocyclyl groups are each optionally substituted by one or more groups selected from hydroxyl, cyano, nitro, $C_1$-$C_6$-alkyl, $C_1$-$C_6$-haloalkyl, $C_1$-$C_6$-alkenyl, $C_1$-$C_6$-alkynyl, —$OC_1$-$C_6$-alkyl, —$OC_2$-$C_6$-alkenyl, —$OC_2$-$C_6$-alkynyl, halogen, $C(O)OH$, $C(O)C_1$-$C_6$-alkyl, $C(O)OC_1$-$C_6$-alkyl, $NR^{18}R^{19}$, $C(O)NR^{20}R^{21}$, $NR^{22}C(O)C_1$-$C_6$-alkyl, $NR^{23}SO_2R^{24}$, —$SC_1$-$C_6$-alkyl, —$S(O)C_1$-$C_6$-alkyl, $SO_2R^{25}$;

$R^7$ represents nitro, $C_1$-$C_6$-alkylcarbonyl, carboxy, $C_1$-$C_6$-alkoxycarbonyl, $C_1$-$C_6$-thioalkyl, $C_1$-$C_6$-alkylsulfinyl, $C_1$-$C_6$-alkylsulfonyl, aminosulfonyl, $C_1$-$C_6$-alkylaminosulfonyl, di-$C_1$-$C_6$-alkylaminosulfonyl, aryl, a C-linked 5-6 membered heteroaryl group or a C- or N-linked 5-6 membered non-aromatic heterocyclyl group, where the ring systems are each optionally substituted by one or more hydroxyl, cyano, nitro, $C_1$-$C_6$-alkyl, $C_1$-$C_6$-alkenyl, $C_1$-$C_6$-alkynyl, $C_1$-$C_6$-alkoxy, $C_1$-$C_6$-alkenyloxy, $C_1$-$C_6$-alkynyloxy, halogen, $C_1$-$C_6$-alkylcarbonyl, carboxy, $C_1$-$C_6$-alkoxycarbonyl, amino, $C_1$-$C_6$-alkylaminocarbonyl, di-$C_1$-$C_6$-alkylaminocarbonyl, $C_1$-$C_6$-alkylcarbonylamino, $C_1$-$C_6$-alkylcarbonyl($C_1$-$C_6$-alkyl)amino, $C_1$-$C_6$-alkylsulfonylamino, $C_1$-$C_6$-alkylsulfonyl($C_1$-$C_6$-alkyl)amino, $C_1$-$C_6$-thioalkyl, $C_1$-$C_6$-alkylsulfinyl, $C_1$-$C_6$-alkylsulfonyl, aminosulfonyl, $C_1$-$C_6$-alkylaminosulfonyl or di-$C_1$-$C_6$-alkylaminosulfonyl groups, where each of the hydrocarbon groups are each optionally substituted by one or more halogen, hydroxyl, $C_1$-$C_6$-alkoxy, amino or cyano substituents;

p is 0 or 1;

z is 0, 1 or 2;

$R^8$, $R^{10}$, $R^{12}$, $R^{13}$, $R^{16}$, $R^{17}$, $R^{18}$, $R^{19}$, $R^{20}$, $R^{21}$, $R^{22}$ and $R^{23}$ are each independently selected from hydrogen, $C_1$-$C_6$ alkyl, $C_3$-$C_8$ cycloalkyl and $C_1$-$C_3$ alkyl-$C_3$-$C_8$ cycloalkyl;

$R^9$ and $R^{11}$ are each independently selected from H, $C_1$-$C_6$ alkyl, $C_3$-$C_6$ cycloalkyl, $C_1$-$C_3$ alkyl-$C_3$-$C_6$ cycloalkyl, $C_1$-$C_3$ alkyl-aryl, $C_1$-$C_3$ alkyl-heterocyclyl, aryl, heterocyclyl, $C(O)C_1$-$C_6$ alkyl, $C(O)C_3$-$C_8$ cycloalkyl, $C(O)C_1$-$C_3$ alkyl-$C_3$-$C_8$ cycloalkyl, $C(O)$aryl, $C(O)$heterocyclyl and $C_1$-$C_3$ alkyl-$OC_1$-$C_3$ alkyl, wherein the cycloalkyl ring is optionally substituted by one or more substituents selected from OH and $NH_2$;

$R^{14}$, $R^{15}$, $R^{24}$ and $R^{25}$ are each independently selected from $C_1$-$C_6$ alkyl, $C_3$-$C_8$ cycloalkyl, $C_1$-$C_3$ alkyl-$C_3$-$C_8$ cycloalkyl, aryl, $NR^{26}R^{27}$ and heterocyclyl, where each of the alkyl and cycloalkyl groups are optionally substituted by one or more halogen, hydroxyl, —$OC_1$-$C_6$-alkyl, phenyl, amino or cyano substituents, and where the aryl and heterocyclyl groups are each optionally substituted by one or more groups selected from hydroxyl, amino, cyano, nitro, $C_1$-$C_6$-alkyl, $C_1$-$C_6$-haloalkyl, —$OC_1$-$C_6$-alkyl, halogen, $C(O)OH$, $C(O)C_1$-$C_6$-alkyl and $C(O)OC_1$-$C_6$-alkyl;

$R^{26}$ is hydrogen or $C_1$-$C_6$ alkyl;

$R^{27}$ is selected from hydrogen, $C_1$-$C_6$ alkyl, $C_3$-$C_8$ cycloalkyl, $C_1$-$C_3$ alkyl-$C_3$-$C_8$ cycloalkyl, $C(O)C_1$-$C_6$ alkyl, aryl, heterocyclyl, $C_1$-$C_3$ alkyl-aryl and $C_1$-$C_3$ alkyl-heterocyclyl, where each of the alkyl and cycloalkyl groups are optionally substituted by one or more halogen, hydroxyl, —$OC_1$-$C_6$-alkyl, phenyl, amino or cyano substituents, and where the aryl and heterocyclyl groups are each optionally substituted by one or more groups selected from hydroxyl, amino, cyano, nitro, $C_1$-$C_6$-alkyl, $C_1$-$C_6$-haloalkyl, —$OC_1$-$C_6$-alkyl, halogen, C(O)OH, C(O)$C_1$-$C_6$-alkyl and C(O)O$C_1$-$C_6$-alkyl;

Heterocyclyl is a 5 to 10 membered saturated, partially saturated or aromatic heterocyclic group containing at least one heteroatom selected from N, O and S, and is optionally substituted by one or more groups selected from hydroxyl, cyano, nitro, $C_1$-$C_6$-alkyl, $C_1$-$C_6$-haloalkyl, $C_1$-$C_6$-alkenyl, $C_1$-$C_6$-alkynyl, —$OC_1$-$C_6$-alkyl, —$OC_2$-$C_6$-alkenyl, —$OC_2$-$C_6$-alkynyl, halogen, C(O)OH, C(O)$C_1$-$C_6$-alkyl, C(O)O$C_1$-$C_6$-alkyl, $NR^{28}R^{29}$, C(O)$NR^{30}R^{31}$, $NR^{32}$C(O)$C_1$-$C_6$-alkyl, $NR^{33}SO_2R^{34}$, —$SC_1$-$C_6$-alkyl, —S(O)$C_1$-$C_6$-alkyl, $SO_2R^{35}$;

$R^{28}$, $R^{29}$, $R^{30}$, $R^{31}$, $R^{32}$ and $R^{33}$ are each independently selected from hydrogen, $C_1$-$C_6$ alkyl, $C_3$-$C_8$ cycloalkyl and $C_1$-$C_3$ alkyl-$C_3$-$C_8$ cycloalkyl; and $R^{34}$ and $R^{35}$ are each independently selected from $C_1$-$C_6$ alkyl, $C_3$-$C_8$ cycloalkyl, $C_1$-$C_3$ alkyl-$C_3$-$C_8$ cycloalkyl, aryl, $NR^{26}R^{27}$ and a 5 to 10 membered heterocyclic group, where the heterocyclic group contains at least one heteroatom selected from N, O and S and where each of the alkyl and cycloalkyl groups are optionally substituted by one or more halogen, hydroxyl, —$OC_1$-$C_6$-alkyl, phenyl, amino or cyano substituents, and where the aryl and heterocyclic groups are each optionally substituted by one or more groups selected from hydroxyl, amino, cyano, nitro, $C_1$-$C_6$-alkyl, $C_1$-$C_6$-haloalkyl, —$OC_1$-$C_6$-alkyl, halogen, C(O)OH, C(O)$C_1$-$C_6$-alkyl and C(O)O$C_1$-$C_6$-alkyl, provided that when Y is a ketone group, then Ar' is not a phenyl group substituted in the 3-position by a benzyl substituted amide group.

Alkyl, alkenyl, alkynyl, alkylene, and alkoxy groups, containing the requisite number of carbon atoms, can be unbranched or branched. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of alkylene include methylene, 1,1-ethylene, 1,2-ethylene, 1,1-propylene, 1,2-propylene, 1,3-propylene and 2,2-propylene.

In the absence of any indication to the contrary, "alkyl" represents $C_1$-$C_6$ alkyl, "alkenyl" represents $C_2$-$C_6$ alkenyl, "alkynyl" represents $C_2$-$C_6$ alkynyl and "cycloalkyl" represents $C_3$-$C_8$ cycloalkyl.

"Halogen" or "halo" may be fluorine, chlorine, bromine or iodine.

Reference to a group optionally substituted refers to replacement of a C—H bond by the requisite bond. Where the substituent is a halogen, the group formed is defined as a haloalkyl group. For example, where the substituent is fluoro, common haloalkyl groups are trifluoroalkyl, 2,2,2-trifluoroethyl or 2,2,2,1,1-pentafluoroethyl groups.

"$C_1$-$C_6$-haloalkyl" refers to an alkyl group substituted by up to seven halogen groups, preferably fluoro groups. For example, where the substituent is fluoro, common haloalkyl groups are trifluoroalkyl, 2,2,2-trifluoroethyl or 2,2,2,1,1-pentafluoroethyl groups.

"amino" includes the unsubstituted —$NH_2$ group, the —N(H)$C_1$-$C_6$ group and the —N($C_1$-$C_6$)$_2$ group. That is to say, the term "amino" encompasses both the monoalkyl- and dialkyl-substituted amino derivatives.

"cycloalkyl" denotes a hydrocarbon ring having the requisite number of carbon atoms, for example cyclopropyl, cyclobutyl, cyclopentyl, cyclohexyl, cycloheptyl or cyclooctyl.

"carbocyclic group" denotes a saturated, partially saturated or aromatic hydrocarbon ring having the requisite number of carbon atoms.

The term "aryl" or "$C_6$-$C_{14}$ aryl" refers to an aromatic carbocyclic group comprising one to three rings. Examples include phenyl, naphthyl, anthracyl and phenanthryl.

The term "heterocyclic" "heterocyclic group" or derivatives thereof refers to a 5 to 10 membered saturated, partially unsaturated or aromatic ring comprising one or more O, N or S heteroatoms. Specific examples of heterocyclyl groups include [1,3]dioxolane, [1,4]dioxane, oxiranyl, aziridinyl, oxetanyl, azetidinyl, tetrahydrofuranyl, pyrrolidinyl, tetrahydropyranyl, piperidinyl, morpholino, thiomorpholinyl, piperazinyl, azepinyl, oxapinyl, oxazepinyl, diazepinyl and heteroaryl groups (see below).

The heterocyclic or heterocyclyl groups are typically bonded via a ring carbon atom. However, where the heterocyclic or heterocyclyl group contains a nitrogen heteroatom, the group may be bonded via a ring carbon atom or a ring nitrogen atom as appropriate. For example, piperidine, piperazine and morpholine groups may be bound via the carbon or one of the ring nitrogen atoms.

The term "heteroaryl" or "heteroaryl group" refers to an aromatic heterocyclic group. Examples of monocyclic heteroaryl groups include pyridyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl. Examples of bicyclic heteroaryl groups include indolyl, benzofuranyl, quinolyl, isoquinolyl and indazolyl.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The following suitable or optional features of a compound of formula (I) may be incorporated into the definition of formula (I) and combined in any number of ways. Thus, the skilled person will appreciate that combinations of the various suitable or optional features set out hereinbelow as embodiments of the invention are within the scope of the invention.

In an embodiment of the invention defined above, A is N.

In a further embodiment of the invention defined anywhere above, Ar' is phenyl or a 5- or 6-membered nitrogen-containing heteroaryl, where each of the phenyl and heteroaryl groups are optionally substituted by one or more substituents selected from List X.

In a yet further embodiment of the invention as defined anywhere above, Ar' is a group

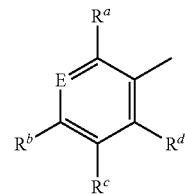

wherein E is N or $CR^e$ $R^a$ is selected from H, halo, $C_1$-$C_6$ alkyl, $C_1$-$C_6$ haloalkyl, $OC_1$-$C_6$ alkyl and $OC_1$-$C_6$ haloalkyl;

$R^b$ is selected from H, $NR^{40}R^{41}$, halo, $C_1$-$C_6$ alkyl, $C_1$-$C_6$ haloalkyl, $OC_1$-$C_6$ alkyl and OH $R^c$ is selected from H, halo, $C_1$-$C_6$ alkyl, $C_1$-$C_6$ haloalkyl, $NR^{42}R^{43}$, C(O)H, C(O)OH, C(O)$C_1$-$C_6$ alkyl, C(O)$C_3$-$C_6$ cycloalkyl, C(O)$C_1$-$C_3$ alkyl-$C_3$-$C_6$ cycloalkyl, C(O)O$C_1$-$C_6$ alkyl, C(O)O$C_3$-$C_6$ cycloalkyl, C(O)O$C_1$-$C_3$ alkyl-$C_3$-$C_6$ cycloalkyl, C(O)NR$^{42}$R$^{43}$, C(O)heterocyclyl, C(O)aryl, NR$^{44}$C(O)C$_1$-C$_6$ alkyl, NR$^{44}$C(O)C$_3$-C$_6$ cycloalkyl, NR$^{44}$C(O)aryl, NR$^{44}$C(O)heterocyclyl, (CH$_2$)$_c$NR$^{44}$S(O)$_2$R$^{45}$, (CH$_2$)$_c$S(O)$_2$R$^{45}$, heterocyclyl and aryl; or R$^b$ and R$^c$, together with the carbon atoms to which they are attached form a 5- or 6-membered carbocyclic or heterocyclic group fused to the ring system, where the carbocyclic and heterocyclic groups are optionally substituted by one or more substituents selected from oxo, C(O)C$_1$-C$_3$ alkyl and C$_1$-C$_6$ alkyl;

R$^d$ is selected from H, C$_1$-C$_6$ alkyl and OC$_1$-C$_6$ alkyl; or

R$^c$ and R$^d$, together with the carbon atoms to which they are attached form a 5- or 6-membered carbocyclic or heterocyclic group fused to the ring system, where the carbocyclic and heterocyclic groups are optionally substituted by one or more substituents selected from oxo, C(O)C$_1$-C$_3$ alkyl and C$_1$-C$_6$ alkyl;

R$^e$ is selected from H, C$_1$-C$_3$ alkyl, C$_1$-C$_3$ haloalkyl and halo;

R$^{40}$, R$^{42}$ and R$^{44}$ are each independently selected from H and C$_1$-C$_6$ alkyl;

R$^{41}$ and R$^{43}$ are each independently selected from H, C$_1$-C$_6$ alkyl, C$_3$-C$_6$ cycloalkyl, C$_1$-C$_3$ alkyl-C$_3$-C$_6$ cycloalkyl, C$_1$-C$_3$ alkyl-aryl, C$_1$-C$_3$ alkyl-heterocyclyl, aryl, heterocyclyl, C(O) C$_1$-C$_6$ alkyl and C$_1$-C$_3$ alkyl-OC$_1$-C$_3$ alkyl, wherein the cycloalkyl ring is optionally substituted by one or more substituents selected from OH and NH$_2$;

R$^{45}$ is selected from C$_1$-C$_6$ alkyl, C$_3$-C$_6$ cycloalkyl, C$_1$-C$_3$ alkyl-C$_3$-C$_6$ cycloalkyl, NR$^{42}$R$^{43}$, aryl and heterocyclyl;

c is 0, 1 or 2; and heterocyclyl is a 5- to 7-membered nitrogen-containing heterocyclic group which is optionally substituted by one or more groups selected from OH, C$_1$-C$_3$ alkyl, C$_3$-C$_6$ cycloalkyl, C$_1$-C$_3$ alkyl-C$_3$-C$_6$ cycloalkyl and C$_1$-C$_3$ hydroxyalkyl.

In a further embodiment, R$^c$ is SO$_2$R$^{45}$, wherein R$^{45}$ is —NHR$^{43}$ or heterocyclyl, suitably an N-bonded heterocyclic group.

In an embodiment of the invention as defined anywhere above, Y is selected from —C(O)C$_1$-C$_6$ alkyl, —C(O)C$_3$-C$_8$ cycloalkyl, —C(O)C$_1$-C$_3$ alkyl-C$_3$-C$_8$ cycloalkyl, —C(O) aryl and —C(O)heteroaryl, where the ring systems are each optionally substituted by one or more substituents selected from List X.

In a yet further embodiment of the invention, Y is selected from —C(O)aryl and —C(O)heteroaryl, where the ring systems are each optionally substituted by one or more substituents selected from List X. Suitably, the aryl group is phenyl and the heteroaryl group is selected from 5- and 6-membered nitrogen-containing heteroaromatic groups.

A suitable individual compound of the invention is selected from:

[3-Amino-6-(6-amino-5-trifluoromethyl-pyridin-3-yl)-pyrazin-2-yl]-pyridiny-3-yl-methanone,
{3-Amino-6-[2-methyl-5-(morpholine-4-sulfonyl)-phenyl]pyrazin-2-yl}-pyridin-3-yl-methanone,
N-{5-[5-Amino-6-(pyridine-3-carbonyl)-pyrazin-2-yl]-2-chloro-pyridin-3-yl}-benzenesulfonamide,
[3-Amino-6-(3-methznesulfonyl-phenyl)-pyrazin-2-yl]-pyridin-3-yl-methanone,
{3-Amino-6-[3-(pyrrolidine-1-sulfonyl)-phenyl]-pyrazin-2-yl}-pyridin-3-yl-methanone,
[3-Amino-6-(4-chloro-3-methyl-phenyl)-pyrazin-2-yl]-pyridin-3-yl-methanone,
N'-{3-[5-amino-6-(pyridine-3-carbonyl)-pyrazin-2-yl]-phenyl}-N,N-dimethyl-sulfamide,
[3-Amino-6-(5-methanesulfonyl-pyridin-3-yl)-pyrazin-2-yl]-pyridin-3-yl-methanone,
[3-Amino-6-(3-chloro-5-methyl-phenyl)-pyrazin-2-yl]-pyridin-3-yl-methanone,
3-[5-Amino-6-(pyridine-3-carbonyl)-pyrazin-2-yl]-N-cyclopropyl-benzenesulfonamide,
[3-Amino-6-(3,4-dichloro-phenyl)pyrazin-2-yl]-pyridin-3-yl-methanone,
Cyclopropanesulfonic acid {3-[5-amino-6-(pyridine-3-carbonyl)-pyrazin-2-yl]-4-methyl-phenyl}-amide,
5-[5-Amino-6-(pyridine-3-carbonyl)-pyrazin-2-yl]-2-chloro-N-phenyl-benzenesulfonamide,
[3-Amino-6-(4-chloro-3-trifluoromethyl-phenyl)-pyrazin-2-yl]-pyridin-3-yl-methanone,
[3-Amino-6-(3-chloro-phenyl)-pyrazin-2-yl]-pyridin-3-yl-methanone,
[3-Amino-6-(3-amino-4-chloro-phenyl)-pyrazin-2-yl]-pyridin-3-yl-methanone,
{3-Amino-6-[4-methoxy-3-morpholine-4-sulfonyl)-phenyl]-pyrazin-2-yl}-pyridin-3-yl-methanone,
[3-Amino-6-(6-chloro-pyridin-3-yl)-pyrazin-2-yl]-pyridin-3-yl-methanone,
1-{3-[5-Amino-6-(pyridine-3-carbonyl)-pyrazin-2-yl]-phenyl}-ethanone,
[3-amino-6-(5-triflouromethyl-pyridin-3-yl)-pyrazin-2-yl]-pyridin-3-yl-methanone,
[3-Amino-6-(3-furan-2-yl-phenyl-pyrazin-2-yl]-pyridin-3-yl-methanone,
5-[5-Amino-6-(pyridine-3-carbonyl)-pyrazine-2-yl]-2-chloro-N,N-dimethyl-benzamide,
[3-Amino-6-(2-chloro-pyridin-4-yl)-pyrazin-2-yl]-pyridin-3-yl-methanone,
3-[5-Amino-6-(pyridine-3-carbonyl)-pyrazin-2-yl]-N-benzyl-4-methyl-benzene sulphonamide,
[3-Amino-6-(1-benzyl-1H-pyrazol-4-yl)-pyrazin-2-yl]-pyrdin-3-yl-methanone,
3-[5-Amino-6-(pyridine-3-carbonyl)-pyrazin-2-yl]-4-fluoro-N-methyl-benzamide,
[3-Amino-6-(6-hydroxy-pyridin-3-yl)-pyrazin-2-yl]-pyridin-3-yl-methanone,
{3-Amino-6-[5-morpholine-4-carbonyl)-pyridin-3-yl]-pyrazin-2-yl}-pyridin-3-yl-methanone,
[3-Amino-6-(3-pyrazol-1yl-phenyl)-pyrazin-2-yl]-pyridin-3-yl-methanone,
[3-Amino-6-(3-morpholin-4-yl-phenyl)-pyrazin-2-yl]-pyridin-3-yl-methanone,
[3-Amino-6-(4-methoxy-pyridin-3-yl)-pyrazin-2-yl]-pyridin-3-yl-methanone,
[3-Amino-6-(2-methoxy-pyridin-4-yl)-pyrazin-2-yl]-pyridin-3-yl-methanone,
N-{3-[5-Amino-6-(pyridine-3-carbonyl)-pyrazin-2-yl]-benzyl}-methansulfonamide,
[3-Amino-6-(1H-pyrazol-4-yl)-pyrazin-2-yl]-pyridin-3-yl-methanone,
(3-Amino-6-benzo[1,3]dioxol-5-yl-pyrazin-2-yl)-pyridin-3-yl-methanone,
[3-Amino-6-(2-trifluoromethoxy-phenyl)-pyrazin-2-yl]-pyridin-3-yl-methanone,
{3-Amino-6-[3-morpholine-4-carbonyl)-phenyl]-pyrazin-2-yl}-pyridin-3-yl-methanone,
{3-Amino-6-[4-fluoro-3-(morpholine-4-carbonyl)-phenyl]-pyrazin-2-yl}-pyridin-3-yl-methanone,
3-[5-Amino-6-(pyridine-3-carbonyl)-pyrazin-2-yl]-4-fluoro-N-isopropyl-benzamide,
{3-Amino-6-[2-methyl-5-(morpholine-4-sulfonyl)-phenyl]-pyrazin-2-yl}-(4-chloro-phenyl)-methanone, {3-Amino-5-methyl-6-[2-methyl-5-(morpholine-4-sulfonyl)-phenyl]-pyrazin-2-yl}-phenyl-methanone,
{3-Amino-6-[2-methyl-5-(morpholine-4-sulfonyl)-phenyl]-pyrazin-2-yl}-phenyl-methanone,
3-(5-Amino-6-benzoyl-pyrazin-2-yl)-N-cyclopropyl-benzenesulfonamide,
{3-Amino-6-[2-methyl-5-(morpholine-4-sulfonyl)-phenyl]-pyrazin-2-yl}-(3,5-difluoro-phenyl)-methanone,
{3-Amino-6-[3-(morpholine-4-fulxonyl)-[phenyl]-pyrazin-2-yl}-(4-fluoro-phenyl)-methanone,
{3-(2-methoxy-ethylamino)-6-[3-morpholine-4-sulfonyl)-phenyl]-pyrazin-2-yl}-pyridin-3-yl-methanone,
[3-Amino-6-(1H-indol-5-yl)-pyrazin-2-yl]-pyridin-3-yl-methanone,
[3-Amino-6-(6-amino-pyridin-3-yl)-pyrazin-2-yl]-pyridin-3-yl-methanone,
3-[5-Amino-6-(pyridine-3-carbonyl)-pyrazin-2-yl]-benzoic acid,
3-[5-Amino-6-(pyridine-3-carbonyl)-pyrazin-2-yl]-benzaldehyde,
[3-Amino-6-(3-amino-phenyl)-pyrazin-2-yl]-pyridin-3-yl-methanone,
[3-Amino-6-(1H-indol-6-yl)-pyrazin-2-yl]-pyridin-3-yl-methanone,
N-{3-[5-(2-Methoxy-ethylamino)-6-(pyridine-3-carbonyl)-pyrazin-2-yl]phenyl}-acetamide,
N-{3-[5-Isopropylamino-6-(pyridine-3-carbonyl)-pyrazin-2-yl]phenyl}acetamide,
N-Cyclopropyl-3-[5-morpholin-4-yl-6-(pyridine-3-carbonyl)-pyrazin-2-yl]benzenesulfonamide,
N-Cyclopropyl-3-[5-(2-methoxy-ethylamino)-6-(pyridine-2-carbonyl)-pyrazin-2-yl]benzenesulfonamide,
N-{3-[5-Amino-6-(-trifluoromethylpyridine-3-carbonyl)pyrazin-2-yl]phenyl}acetamide,
3-[5-Amino-6-(pyridine-3-carbonyl)-pyrazin-2-yl]-N-(2-methoxy-ethyl)-benzenesulfonamide,
5-[5-Amino-6-(pyridine-3-carbonyl)-pyrazin-2-yl]-2-chloro-N-(4-hydroxy-cyclohexyl)-benzene sulfonamide,
{3-Amino-6-[3-(morpholine-4-sulfonyl)-4-trifluoromethyl-phenyl]-pyrazin-2-yl}-pyridin-3-yl-methanone,
5-[5-Amino-6-(pyridine-3-carbonyl)-pyrazin-2-yl-N-cyclopropyl-2,4-difluoro-benzenesulfonamide,
1-{6-[5-Amino-6-(pyridine-3-carbonyl)-pyrazin-2-yl]-2,3-dihydro-indol-1-yl}-ethanone,
6-[5-Amino-6-(pyridine-3-carbonyl)-pyrazin-2-yl]-1,3-dihydro-indol-2-one,
{3-Amino-6-[3-(4-methyl-piperazine-1-sulfonyl)-5-trifluoromethyl-phenyl]-pyrazin-2-yl}-pyridin-3-yl-methanone,
6-[5-Amino-6-(pyridine-3-carbonyl)-pyrazin-2-yl]-4H-benzo[1,4]oxazin-3-one,
[3-Amino-6-(1H-indol-4-yl)-pyrazin-2-yl]-pyridin-3-yl-methanone,
3-[5-Amino-6-(pyridine-3-carbonyl)-pyrazin-2-yl]-5-trifluoromethyl-benzenesulfonamide,
{3-Amino-6-[3-(4-methyl-piperazine-1-sulfonyl)-4-trifluoromethyl-phenyl]-pyrazin-2-yl}-pyridin-3-yl-methanone,
{3-Amino-6-[5-morpholine-4-sulfonyl)-pyridin-3-yl]-pyrazin-2-yl}-pyridin-3-yl-methanone,
{3-Amino-6-[2,4-difluoro-5-(4-methyl-piperazine-1-sulfonyl)-phenyl]-pyrazin-2-yl}-pyridin-3-yl-methanone,
{3-Amino-6-[-4-chloro-3-(4-methyl-piperazine-1-sulfonyl)-phenyl]-pyrazin-2-yl}-pyridin-3-yl-methanone,
{3-Amino-6-[3-(4-cyclopropyl-piperazine-1-sulfonlyl)-phenyl]-pyrazin-2-yl}-pyridin-3-yl-methanone,
{3-Amino-6-[3-(4-methyl-[1,4]diazepane-1-sulfonyl)-phenyl]-pyrazin-2-yl}pyridine-3-yl-methanone,
{3-Amino-6-[2,4-difluoro-5-(morpholine-4-sulfonyl)-phenyl]-pyrazin-2-yl}-pyridin-3-yl-methanone,
(3-Amino-6-{3-[4-(2-hydroxy-ethyl)-piperazine-1-sulfonyl]-phenyl}-pyrazin-2-yl)-pyridin-3-yl-methanone,
3-[5-Amino-6-(pyridine-3-carbonyl)-pyrazin-2-yl]-N-[2-(4-methyl-piperazin-1-yl)-ethyl]-benzenesulfonamide,
3-[5-Amino-6-(pyridine-3-carbonyl)-pyrazin-2-yl]-N-cyclobutyl-benzenesuflonamide,
{3-Amino-6-[3-(4-methyl-piperazine-1-sulfonyl)-phenyl]-pyrazin-2-yl}-pyridin-3-yl-methanone,
5-[5-Amino-6-(pyridine-3-carbonyl)-pyrazin-2-yl]-2-chloro-N-cyclopropyl-benzenesuflonamide,
{3-Amino-6-[4-chloro-3-(morpholine-4-sulfonyl)-phenyl]-pyrazin-2-yl}-pyridin-3-yl-methanone,
3-[5-Amino-6-(pyridine-3-carbonyl)-pyrazin-2-yl]-N-cyclopropylmethyl-benzenesulfonamide,
{3-Amino-6-[3-(4-methyl-piperazine-1-sulfonyl)-phenyl]-pyrazin-2-yl}-(4-chloro-phenyl)-methanone,
{3-amino-6-[4-chloro-3-(4-methyl-piperazine-1-sulfonyl)-phenyl]-pyrazin-2-yl}-(4-chloro-phenyl)-methanone,
{3-Amino-6-[4-chloro-3-(4-isopropyl-pierazine-1-sulfonyl)-phenyl]-pyrazin-2-yl}-(4-chloro-phenyl)-methanone,
3-[5-Amino-6-(4-fluoro-benzoyl)-pyrazin-2-yl]-N-(2-methoxy-ethyl)-benzenesulfonamide,
[3-Amino-6-(3,4-dichloro-phenyl)-pyrazin-2-yl]-(4-piperidin-1-ylmethyl-phenyl)-methanone,
{3-Amino-6-[2-methyl-5-(morpholine-4-sulfonyl)-phenyl]-pyrazin-2-yl}-cyclopropyl-methanone,
3-[6-Amino-5-(4-tert-butyl-benzoyl)-pyridin-3-yl]-N-cyclopropyl-benzenesulfonamide,
3-(6-Amino-5-benzoyl-pyridin-3-yl)-N-cyclopropyl-benzenesulfonamide,
[2-Amino-5-(3-chloro5-methyl-phenyl)-pyridin-3-yl]-phenyl-methanone,
{2-Amino-5-[2-methyl-5-(morpholine-4-sulfonyl)-phenyl]-pyridin-3-yl}-pyridin-3-yl-methanone,
{2-Amino-5-[3-(4-methyl-piperazine-1-sulfonyl)-phenyl]-pyridin-3-yl}-pyridin-2-yl-methanone,
[2-Amino-5-(3-chloro5-methyl-phenyl)-pyridin-3-yl]-phenyl-methanone,
5-[5-Amino-6-(pyridine-3-carbonyl)-pyrazin-2-yl]-N-cyclopropylmethyl-2,4-difluoro-benzenesulfonamide,
5-[5-Amino-6-(pyridine-3-carbonyl)-pyrazin-2-yl]-2,4-difluoro-N-(2-methoxy-ethyl)-benzenesulfonamide,
5-[5-Amino-6-(pyridine-3-carbonyl)-pyrazin-2-yl]-N-(2-methoxy-ethyl)-2-trifluoromethyl-benzenesulfonamide,
5-[5-Amino-6-(pyridine-3-carbonyl)-pyrazin-2-yl]-2,4-difluoro-N-(4-hydroxy-cyclohexyl)-benzenesulfonamide,
{3-Amino-6-[2-methyl-5-(morpholine-4-sulfonyl)-phenyl]-pyrazin-2-yl}-pyridin-3-yl-methanone O-methyl-oxime,
5-(5-Amino-6-cyclopropanecarbonyl-pyrazin-2-yl)-2,4-difluoro-N-(4-hydroxy-cyclohexyl)-benzenesulfonamide,
3-(5-Amino-6-cyclopropanecarbonyl-pyrazin-2-yl)-N-(2-methoxy-ethyl)-benzenesulfonamide, {3-Amino-6-[2-methyl-5-(morpholine-4-sulfonyl)-phenyl]-pyrazin-2-yl}-pyridin-3-yl-methanone O-(2-dimethylamino-ethyl)-oxime, 3-[5-Amino-6-(pyridin-3-yloxy)-pyrazin-2-yl]-N-cyclopropyl-benzenesulfonamide, 5-(5-Amino-pyrazin-2-yl)-2-chloro-N-(4-hydroxy-cyclohexyl)-benzenesulfonamide, 5-(5-Amino-pyrazin-2-yl)-2,4-difluoro-N-(2-methoxy-ethyl)-benzenesulfonamide, 5-(5-Amino-pyrazin-2-yl)-N-(4-hydroxy-cyclohexyl)-2-trifluoromethyl-benzenesulfonamide, {3-Amino-6-[3-(morpholine-4-sulfonyl)-phenyl]-pyrazin-2-yl}-pyridin-3-yl-methanone, 5-[5-Amino-6-(pyridine-3-carbonyl)-pyrazin-2-yl]-2-chloro-N-(2-methoxy-ethyl)-benzenesulfonamide, {3-(2-Methoxy-ethylamino)-6-[2-methyl-5-(morpholine-4-sulfonyl)-phenyl]-pyrazin-2-yl}-pyridin-3-yl-methanone, 5-[2-Methyl-5-(morpholine-4-sulfonyl)-phenyl]-N*3*-pyridin-3-yl-pyrazine-2,3-diamine, N-{3-[5-Amino-6-(pyridine-3-carbonyl)-pyrazin-2-yl]-phenyl}-methanesulfonamide,

[3-Amino-6-(5-amino-2-methyl-phenyl)-pyrazin-2-yl-methanone,

N-{3-[5-Amino-6-(pyridine-3-carbonyl)-pyrazin-2-yl]-4-methyl-phenyl}-acetamide and pharmaceutically acceptable salts thereof.

Compounds of formula I that contain a basic centre are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid, hydroiodic acid, nitric acid, sulfuric acid, phosphoric acid; and organic acids, for example aliphatic monocarboxylic acids such as formic acid, acetic acid, trifluoroacetic acid, propionic acid and butyric acid, caprylic acid, dichloroacetic acid, hippuric acid, aliphatic hydroxy acids such as lactic acid, citric acid, tartaric acid or malic acid, gluconic acid, mandelic acid, dicarboxylic acids such as maleic acid or succinic acid, adipic acid, aspartic acid, fumaric acid, glutamic acid, malonic acid, sebacic acid, aromatic carboxylic acids such as benzoic acid, p-chloro-benzoic acid, nicotinic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid, ethanesulfonic acid, ethane-1,2-disulfonic acid, 2-hydroxy-ethanesulfonic acid, (+) camphor-10-sulfonic acid, naphthalene-2-sulfonic acid, naphthalene-1,5-disulfonic acid or p-toluenesulfonic acid. These salts may be prepared from compounds of formula I by known salt-forming procedures. Pharmaceutically acceptable solvates are generally hydrates.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine, arginine, benethamine, benzathine, diethanolamine, 4-(2-hydroxy-ethyl)morpholine, 1-(2-hydroxyethyl) pyrrolidine, N-methyl glutamine, piperazine, triethanolamine or tromethamine. These salts may be prepared from compounds of formula I by known salt-forming procedures. Compounds of formula I that contain acidic, e.g. carboxyl, groups may also exist as zwitterions with the quaternary ammonium centre.

Pharmaceutically acceptable solvates in accordance with the invention include those wherein the solvent of crystallisation may be isotopically substituted e.g. $D_2O$, $d_6$-acetone or $d_6$-DMSO.

Compounds of formula I in free form may be converted into salt form, and vice versa, in a conventional manner. The compounds in free or salt form can be obtained in the form of hydrates or solvates containing a solvent used for crystallisation. Compounds of formula I can be recovered from reaction mixtures and purified in a conventional manner. Isomers, such as enantiomers, may be obtained in a conventional manner, e.g. by fractional crystallisation or asymmetric synthesis from correspondingly asymmetrically substituted, e.g. optically active, starting materials.

Some compounds of the invention contain at least one asymmetric carbon atom and thus they exist in individual optically active isomeric forms or as mixtures thereof, e.g. as racemic mixtures. In cases where additional asymmetric centres exist the present invention also embraces both individual optically active isomers as well as mixtures, e.g. diastereomeric mixtures, thereof.

The invention includes all such forms, in particular the pure isomeric forms. The different isomeric forms may be separated or resolved one from the other by conventional methods, or any given isomer may be obtained by conventional synthetic methods or; by stereospecific or asymmetric syntheses. Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

The invention includes all pharmaceutically acceptable isotopically-labelled compounds of formula I wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen e.g. $^2H$ and $^3H$, carbon e.g. $^{11}C$, $^{13}C$ and $^{14}C$, chlorine e.g. $^{36}Cl$, fluorine e.g. $^{18}F$, iodine e.g. $^{123}I$ and $^{125}I$, nitrogen e.g. $^{13}N$ and $^{15}N$, oxygen e.g. $^{15}O$, $^{17}O$ and $^{18}O$, and sulfur e.g. $^{35}S$.

Certain isotopically-labelled compounds of formula I, for example those incorporating a radioactive isotope, are useful in drug and/or substrate tissue distribution studies. The radioactive isotopes tritium ($^3H$) and carbon-14 ($^{14}C$) are particularly useful for this purpose in view of their ease of incorporation and ready means of detection. Substitution with heavier isotopes such as deuterium ($^2H$) may afford certain therapeutic advantages that result from greater metabolic stability, for example increased in vivo half-life or reduced dosage requirements, and hence may be preferred in some circumstances. Substitution with positron emitting isotopes, such as $^{11}$C, $^{18}$F, $^{15}$O, and $^{13}$N can be useful in Positron Emission Topography (PET) studies for examining substrate receptor occupancy.

Isotopically-labelled compounds of formula I can generally be prepared by conventional techniques known to those skilled in the art or by processes analogous to those described in the accompanying examples using an appropriate isotopically-labelled reagent in place of the non-labelled reagent previously used.

Some of the compounds of Formula I may exist in different tautomeric forms. Tautomerism is well known to those skilled in the art and the skilled person will readily appreciate which groups are able to tautomerise to form the different tautomeric forms. The invention includes all tautomeric forms of the compounds of Formula I.

Specific suitable compounds of formula I are described hereinafter in the Examples.

The invention provides, in another aspect, a process for preparing a compound of formula (I). For example, compounds of formula (I) are prepared according to Scheme 1.

The reaction between A1 and A2 is carried out using a suitable palladium catalyst, such as Pd(dppf)Cl$_2$, in a suitable solvent, such as DCM or DMF. The reaction typically includes a base, such as sodium carbonate or Et$_3$N and may be carried out at elevated temperatures, such as at reflux.

As an alternative to the above scheme, A1 may be reacted with a suitable boron compound in the presence of a catalyst in order to form the boronic acid/boronic anhydride derivative of A1 and then reacted with Ar'—Br (A3) to form a compound of Formula I in a two-step procedure.

An alternative method of preparing compounds of formula (I), is shown in scheme 2. For example, compounds of formula (I) where A, Ar', R$^1$ and R$^2$ are as defined above, and Y is a ketone group represented by C(O)Y', are prepared as shown.

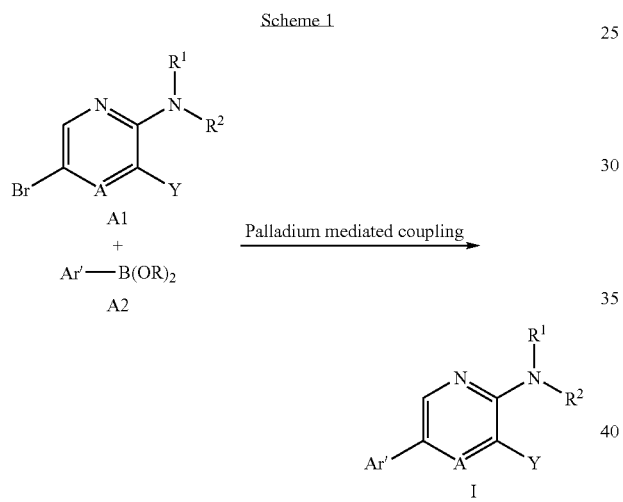

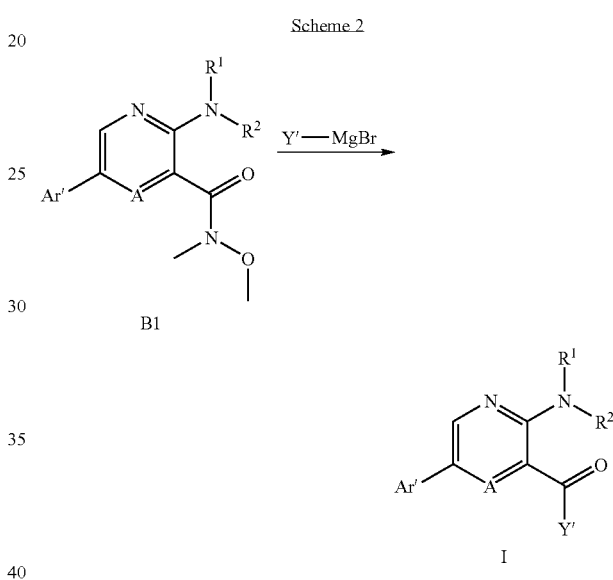

When A is N and Y is C(O)Y', compounds of Formula A1 may be formed by the route set out in Scheme 3:

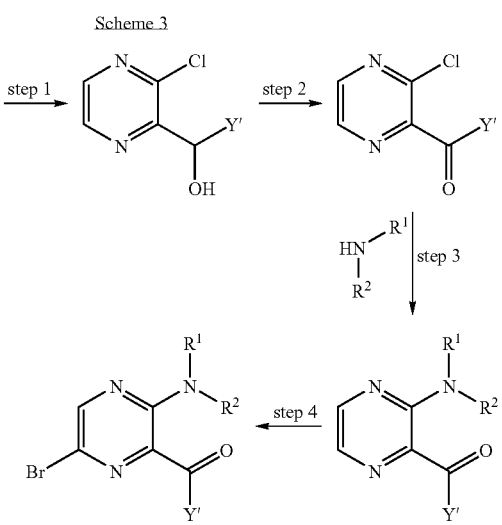

When A is CH and Y is C(O)Y', compounds of Formula A1 may be formed by the route set out in Scheme 4:

Scheme 4

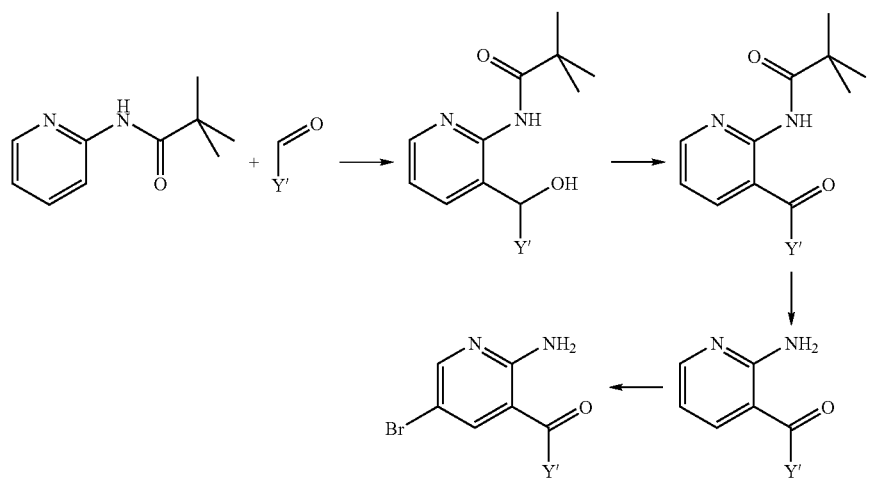

When R1 and R2 are both hydrogen, compounds of Formula B1 may be formed by the route set out in Scheme 5.

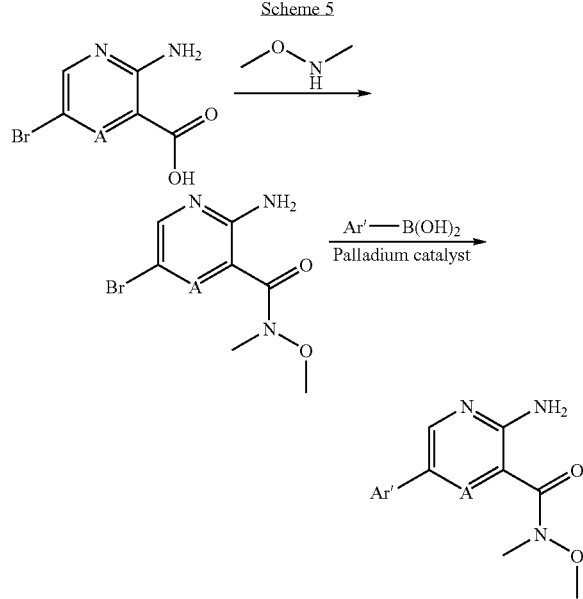

Compounds of formula I and their pharmaceutically acceptable salts are useful as pharmaceuticals. In particular, they exhibit inhibition of phosphatidylinositol 3-kinase (PI 3-kinase) enzymes, especially the gamma isoform (p110γ), which are responsible for generating phosphorylated signalling products. Thus, the compounds of the present invention are useful in the treatment of disorders involving PI 3-kinase, particularly PI 3-kinase gamma isoform.

The inhibitory properties of compounds of formula I may be demonstrated in the following test procedures:

Baculovirus expressing different fragments of human PI 3-Kγ fused to glutathione S-transferase (GST) have been previously described by Stoyanova, S., Bulgarelli-Leva, G., Kirsch, C., Hanck, T., Klinger, R., Wetzker, R., Wymann, M. P. (1997) Lipid- and protein kinase activities of G protein-coupled PI 3-kinase g: structure-activity analysis and interactions with wortmannin. Biochem. J., 324:489. Residues 38-1102 of human PI 3-Kγ are subcloned into the BamH1 and EcoR1 sites of the transfer vector pAcG2T (Pharmingen) to create a GST-PI 3-Kγ lacking the first 37 residues of PI 3-Kγ. To express the recombinant protein, Sf9 (Spodoptera frugiperda 9) insect cells are routinely maintained at densities between $3 \times 10^5$ and $3 \times 10^6$ cells/ml in serum containing TNMFH medium (Sigma). Sf9 cells, at a density of $2 \times 10^6$ are infected with human GST-PI 3-KγΔ34 baculovirus at a multiplicity of infection (m.o.i.) of 1 for 72 hours. The infected cells are harvested by centrifugation at 1400 g for 4 minutes at 4° C. and the cell pellets are frozen at −80° C. Both Sf9 and Sf21 cells work equally well. Sf9 cells ($1 \times 10^9$) are resuspended in 100 ml cold (4° C.) lysis buffer (50 mM Tris-HCl pH 7.5, 1% Triton X-100, 150 mM NaCl, 1 mM NaF, 2 mM DTT and protease inhibitors. Cells are incubated on ice for 30 minutes then centrifuged at 15000 g for 20 minutes at 4° C. Purification of the supernatant sample is carried out at 4° C. by affinity chromatography using SEPHAROSE™ agarose gel beads coupled to glutathione (from Amersham Pharmacia Biotech). A cell lysate/GST resin ratio of 50:1 is used. The GST resin is firstly pre-rinsed to remove ethanol preservative and then equilibrated with lysis buffer. Cell lysate (supernatant) is added (usually as 50 ml lysate to 1 ml GST resin in 50 ml tubes) and gently rotated on a mixer at 4° C. for 2-3 hours. The unbound flow through sample is collected by centrifugation at 1000 g for 5 minutes at 4° C. using a DENLEY™ centrifuge. The 1 ml GST resin containing bound material is transferred to a 15 ml FALCON™ centrifuge tube for subsequent washing and elution steps. Firstly a series of 3 cycles of washings (mixing by gentle inversion) is performed with 15 ml ice cold wash Buffer A (50 mM Tris-HCl pH 7.5, 1% Triton X-100, 2 mM DTT) interspersed with centrifugation at 1000 g for 5 minutes at 4° C. A final single wash step is performed with 15 ml ice cold wash Buffer B (50 mM Tris-HCl pH 7.5, 2 mM DTT) and then centrifuged at 1000 g for 5 minutes at 4° C. The washed GST resin is finally eluted with 4 cycles of 1 ml ice cold elution buffer (50 mM Tris-HCl pH 7.5, 10 mM reduced glutathione, 2 mM DTT, 150 mM NaCl, 1 mM NaF, 50% ethylene glycol and protease inhibitors) interspersed with centrifugation at 1000 g for 5 minutes at 4° C. Samples are aliquoted and stored at −20° C.

An in vitro kinase assay was established that measures the transfer of the terminal phosphate of adenosine triphosphate to phosphatidylinositol. The kinase reaction is performed in a white 96 well microtitre plate as a Scintillation Proximity Assay. Each well contains 10 µl test compound in 5% dimethylsulfoxide and 20 µl assay mix (40 mM Tris, 200 mM NaCl, 2 mM ethyleneglycol-aminoethyl-tetraacetic acid (EGTA), 15 µg/ml phosphatidylinositol, 12.5 µM adenosine triphosphate (ATP), 25 mM $MgCl_2$, 0.1 µCi [$^{33}$P]ATP). The reaction is started by the addition of 20 µl of enzyme mix (40 mM Tris, 200 mM NaCl, 2 mM EGTA containing recombinant GST-p110γ). The plate is incubated at room temperature for 60 minutes and the reaction terminated by the adding 150 µl of WGA-bead stop solution (40 mM Tris, 200 mM NaCl, 2 mM EGTA, 1.3 mM ethylene diamine tetraacetic acid (EDTA), 2.6 µM ATP and 0.5 mg of Wheat Germ Agglutinin-SPA beads (Amersham Biosciences) to each well. The plate is sealed, incubated at room temperature for 60 minutes, centrifuged at 1200 rpm and then counted for 1 minute using a scintillation counter. Total activity is determined by adding 10 µl of 5% dimethylsulfoxide (DMSO) and non-specific activity is determined by adding 10 µl 50 mM EDTA in place of the test compound.

All compounds of the Examples herein below have $IC_{50}$ values below 1 µM in the aforementioned assay. In particular, Examples 1, 13, 28, 35, 49, 51, 67, 74, 86 and 92 have respective Pi3K (gamma) $IC_{50}$ values of 0.033, 0.012, 0.373, 0.587, 0.362, 0.393, 0.431, 0.125, 0.753 and 0.030 µM.

Having regard to their inhibition of phosphatidylinositol 3-kinase enzymes, compounds of formula I in free or pharmaceutically acceptable salt form, hereinafter alternately referred to as "agents of the invention", are useful in the treatment of conditions which are mediated by the activation of the PI 3-kinase enzymes, particularly inflammatory or allergic conditions. Treatment in accordance with the invention may be symptomatic or prophylactic.

Accordingly, agents of the invention are useful in the treatment of inflammatory or obstructive airways diseases, resulting, for example, in reduction of tissue damage, airways inflammation, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy).

Other diseases or conditions which may be treated with agents of the invention include thrombosis, hypertension, heart ischaemia and pancreatitis, (Nature review November 2006 Vol 5), treatment of anaemia including haemolytic anaemia, aplastic anaemia and pure red cell anaemia (WO 2006/040318), septic shock, rheumatoid arthritis, osteoarthritis, proliferative diseases such as cancer, atherosclerosis, allograft rejection following transplantation, stroke, obesity, restenosis, diabetes, e.g. diabetes mellitus type I (juvenile diabetes) and diabetes mellitus type II, diarrheal diseases, ischemia/reperfusion injuries, retinopathy, such as diabetic retinopathy or hyperbaric oxygen-induced retinopathy, and conditions characterised by elevated intraocular pressure or secretion of ocular aqueous humor, such as glaucoma.

Agents of the present invention may be useful in the treatment or prevention of heart failure such as (acute and chronic) congestive heart failure, left ventricular dysfunction including impaired cardiac contractility, hypertrophic cardiomyopathy, diabetic cardiac myopathy and other types of detrimental cardiac dysfunction and remodelling.

Other diseases or conditions which may be treated with agents of the invention include septic shock, rheumatoid arthritis, osteoarthritis, proliferative diseases such as cancer, atherosclerosis, allograft rejection following transplantation, stroke, obesity, restenosis, diabetes, e.g. diabetes mellitus type I (juvenile diabetes) and diabetes mellitus type II, diarrheal diseases, ischemia/reperfusion injuries, retinopathy, such as diabetic retinopathy or hyperbaric oxygen-induced retinopathy, and conditions characterised by elevated intraocular pressure or secretion of ocular aqueous humor, such as glaucoma.

The agents of the invention may also be useful in the treatment of visceral disorders, inflammatory bowel disease, inflammatory bowel disorder, cystitis, e.g. interstitial cystitis and urinary incontinence including bladder detrusor hyperreflexia and bladder hypersensitivity.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, *J. Immunol. Methods* (1997) 202:49-57; Renzi et al, *Am. Rev. Respir. Dis.* (1993) 148:932-939; Tsuyuki et al., *J. Clin. Invest.* (1995) 96:2924-2931; and Cernadas et al (1999) *Am. J. Respir. Cell Mol. Biol.* 20:1-8.

The agents of the invention are also useful as co-therapeutic agents for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosage or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory or antihistamine drug substance, said agent of the invention and said drug substance being in the same or different pharmaceutical composition. Such anti-inflammatory drugs include steroids, in particular glucocorticosteroids such as budesonide, beclamethasone dipropionate, fluticasone propionate, ciclesonide or mometasone furoate and compounds described in WO 0200679, WO 0288167, WO 0212266 and WO 02100879, LTB4 antagonists such as those described in U.S. Pat. No. 5,451,700, LTD4 antagonists such as montelukast and zafirlukast, dopamine receptor agonists such as cabergoline, bromocriptine, ropinirole and 4-hydroxy-7-[2-[[2-[[3-(2-phenylethoxy)-propyl]-sulfonyl]ethyl]-amino]ethyl]-2(3H)-benzothiazolone and pharmaceutically acceptable salts thereof (the hydrochloride being Viozan®—AstraZeneca), and PDE4 inhibitors such as Ariflo® (GlaxoSmithKline), Roflumilast (Byk Gulden), V-11294A (Napp), BAY19-8004 (Bayer), SCH-351591 (Schering-Plough), Arofylline (Almirall Prodesfarma), PD189659 (Parke-Davis), AWD-12-281 (Asta Medica), CDC-801 (Celgene) and KW-4490 (Kyowa Hakko Kogyo) as well as those described in WO 98/18796 and WO 03/39544. Such bronchodilatory drugs include anticholinergic or antimuscarinic agents, in particular ipratropium bromide, oxitropium bromide and tiotropium salts but also those described in WO 01/04118, WO 02/51841, WO 02/53564, WO 03/00840, WO 03/87094, WO 04/05285, WO 02/00652, WO 03/53966, EP 424021, U.S. Pat. No. 5,171,744, U.S. Pat. No. 3,714,357 and WO 03/33495, and beta-2 adrenoceptor agonists such as salbutamol, terbutaline, salmeterol and, especially, formoterol and pharmaceutically acceptable salts thereof, and compounds (in free or salt or solvate form) of formula I of PCT International patent publication No. WO 00/75114, which document is incorporated herein by reference, preferably compounds of the Examples thereof, especially 5-[(R)-2-(5,6-Diethyl-indan-2-ylamino)-1-hydroxy-ethyl]-8-hydroxy-1H-quinolin-2-one, and pharmaceutically acceptable salts thereof. Co-therapeutic antihistamine drug substances include cetirizine hydrochloride, acetaminophen, clemastine fumarate, promethazine, loratidine, desloratidine, diphenhydramine and fexofenadine hydrochloride. Combinations of agents of the invention and steroids, beta-2 agonists, PDE4 inhibitors or LTD4 antagonists may be used, for example, in the treatment of COPD or, particularly, asthma. Combinations of agents of the invention and anticholinergic or antimuscarinic agents, PDE4 inhibitors, dopamine receptor agonists or LTB4 antagonists may be used, for example, in the treatment of asthma or, particularly, COPD.

Other useful combinations of agents of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-aminium chloride (TAK-770), and CCR-5 antagonists described in U.S. Pat. No. 6,166,037 (particularly claims 18 and 19), WO00/66558 (particularly claim 8), and WO00/66559 (particularly claim 9).

Pi3 kinase inhibitors, e.g. those compounds of the invention, may be combined with an angiotensin receptor blocker, e.g. valsartan (an angiotensin receptor blocker) and achieve greater therapeutic effect than the administration of valsartan alone. The combination regimen also surprisingly reduces the rate of progression of cardiac, renal and cerebral end-organ damage. The combination elicits enhanced antihypertensive effects (whether malignant, essential, reno-vascular, diabetic, isolated systolic, or other secondary type of hypertension) and lessening of pulse pressure. The combination is also effective in treating supraventricular and ventricular arrhythmias, atrial fibrillation, atrial flutter or detrimental vascular remodeling. It can further be shown that the combination is beneficial in the treatment and prevention of myocardial infarction and its sequelae, and is useful in treating atherosclerosis, angina (whether stable or unstable), renal insufficiency (diabetic and non-diabetic), peripheral vascular disease, cognitive dysfunction, and stroke. Furthermore, the improvement in endothelial function with the combination therapy provides benefit in diseases in which normal endothelial function is disrupted such as heart failure, angina pectoris and diabetes. Furthermore, the combination may be used for the treatment or prevention of primary and secondary pulmonary hypertension, renal failure conditions, such as diabetic nephropathy, glomerulonephritis, scleroderma, glomerular sclerosis, proteinuria of primary renal disease, and also renal vascular hypertension, diabetic retinopathy, the management of other vascular disorders, such as migraine, peripheral vascular disease, Raynaud's disease, luminal hyperplasia, cognitive dysfunction (such as Alzheimer's), glaucoma and stroke.

Agents of the invention may also be useful in the treatment of diseases or disorders mediated by lymphocytes interactions, e.g. in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, Graves ophthalmopathy, alopecia areata and others, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis and further eczematous dermatitises, seborrhoeic dermatitis, cutaneous manifestations of immunologically-mediated disorders, inflammatory eye disease, myocarditis or hepatitis, gut ischemia, traumatic shock, cancer, e.g. breast cancer, T cell lymphomas or T cell leukemias, infectious diseases, e.g. toxic shock (e.g. superantigen induced), septic shock, adult respiratory distress syndrome or viral infections, e.g. AIDS, viral hepatitis, chronic bacterial infection, or senile dementia. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus.

Agents of the invention may be administered in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders. For example, the compounds of formula I may be used in combination with a calcineurin inhibitor, e.g. cyclosporin A or FK 506; a mTOR inhibitor, e.g. rapamycin, 40-O-(2-hydroxyethyl)-rapamycin, CCI779, ABT578, AP23573, biolimus-7 or biolimus-9; an ascomycin having immuno-suppressive properties, e.g. ABT-281 or ASM981; corticosteroids; cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; a JAK3 kinase inhibitor, e.g. N-benzyl-3,4-dihydroxy-benzylidene-cyanoacetamide α-cyano-(3,4-dihydroxy-)]N-benzylcinnamamide (Tyrphostin AG 490), prodigiosin 25-C (PNU156804), [4-(4'-hydroxyphenyl)-amino-6,7-dimethoxyquinazoline] (WHI-P131), [4-(3'-bromo-4'-hydroxylphenyl)-amino-6,7-dimethoxyquinazoline] (WHI-P154), [4-(3', 5'-dibromo-4'-hydroxylphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690,550), or a compound as disclosed in WO 04/052359 or WO 05/066156; a S1P receptor agonist or modulator, e.g. FTY720 optionally phosphorylated or an analog thereof, e.g. 2-amino-2-[4-(3-benzyloxyphenylthio)-2-chlorophenyl]ethyl-1,3-propanediol optionally phosphorylated or 1-{4-[1-cyclohexyl-3-trifluoromethyl-benzyloxyimino)-ethyl]-2-ethyl-benzyl}-azetidine-3-carboxylic acid or its pharmaceutically acceptable salts; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists.

The agents of the invention may also be useful in the treatment of visceral disorders, inflammatory bowel disease, inflammatory bowel disorder, cystitis, e.g. interstitial cystitis and urinary incontinence including bladder detrusor hyperreflexia and bladder hypersensitivity.

The agents of the invention may also be used in the treatment of anaemia, according to WO2006/040318.

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

The present invention also provides a pharmaceutical composition comprising a compound of formula I in free form or in the form of a pharmaceutically acceptable salt, optionally together with a pharmaceutically acceptable diluent or carrier therefor. The composition may contain a co-therapeutic agent, such as an anti-inflammatory, bronchodilatory or antihistamine drug as hereinbefore described. Such compositions may be prepared using conventional diluents or excipients and techniques known in the galenic art. Thus oral dosage forms may include tablets and capsules.

Formulations for topical administration may take the form of creams, ointments, gels or transdermal delivery systems, e.g. patches. Compositions for inhalation may comprise aerosol or other atomisable formulations or dry powder formulations.

When the composition comprises an aerosol formulation, it preferably contains, for example, a hydrofluoroalkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

Dosages of agents of the invention employed in practising the present invention will of course vary depending, for example, on the particular condition to be treated, the effect desired and the mode of administration. In general, suitable daily dosages for oral administration are of the order of 0.1 to 10 mg/kg.

A further aspect of the invention provides a compound of Formula I as defined anywhere above for use as a pharmaceutical.

A yet further aspect of the invention provides a compound of Formula I as defined anywhere above for use as a pharmaceutical in the treatment of inflammatory or allergic conditions, in particular, the inflammatory or allergic conditions discussed hereinabove.

EXAMPLES

Suitable compounds of the present invention include compounds of formula 1a as set out in Table 1

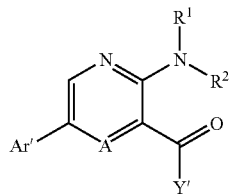

TABLE 1-continued

| Ex. | Structure | [M + H]+ |
|---|---|---|
| 6 | 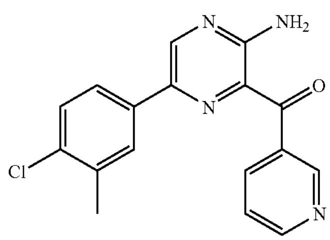 | 325 |
| 7 | 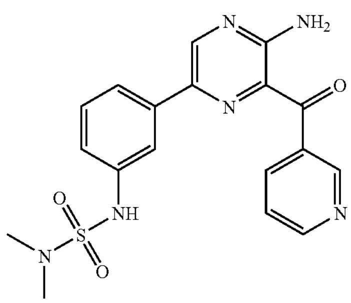 | 399 |
| 8 | 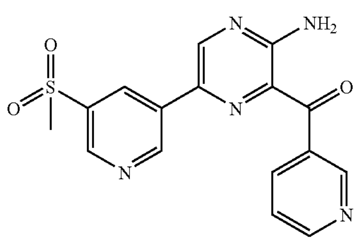 | 356 |
| 9 | 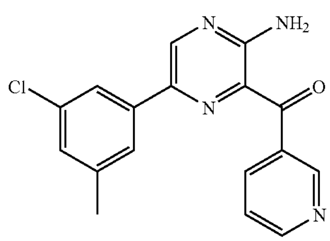 | 325 |
| 10 | 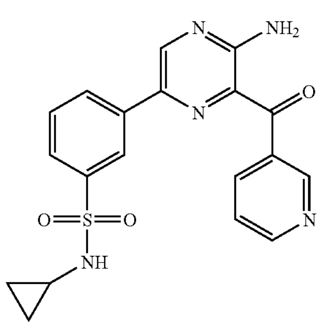 | 396 |
| 11 | | 345/347 |
| 12 | | 410 |
| 13 | | 466 |
| 14 | | 379 |
| 15 | | 311 |

TABLE 1-continued

| Ex. | Structure | [M + H]+ |
|---|---|---|
| 16 | 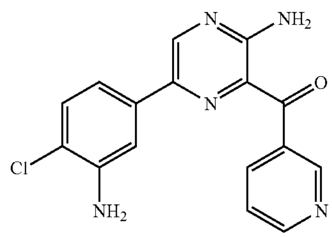 | 326 |
| 17 | 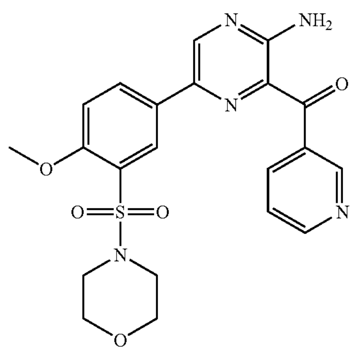 | 456 |
| 18 | 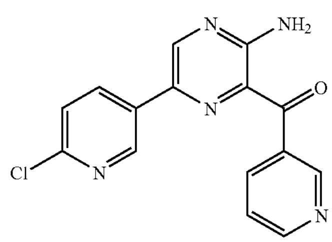 | 312 |
| 19 | 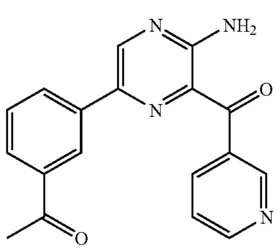 | 319 |
| 20 | 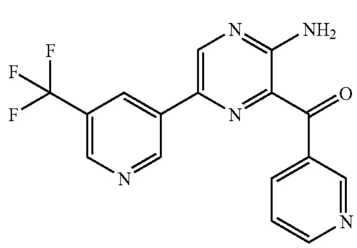 | 346 |
| 21 | | 343 |
| 22 | | 382 |
| 23 | | 312 |
| 24 | | 460 |
| 25 | | 357 |

TABLE 1-continued
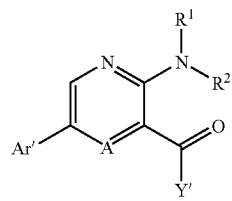
| Ex. | Structure | [M + H]+ |
|---|---|---|
| 26 | 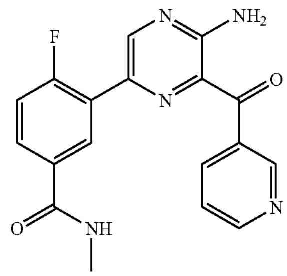 | 352 |
| 27 | 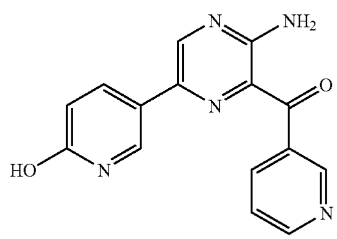 | 294 |
| 28 | 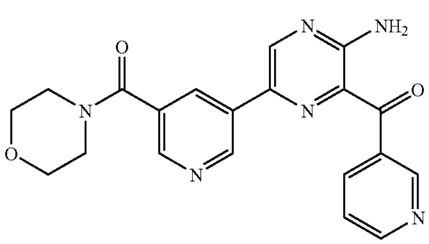 | no ion |
| 29 | 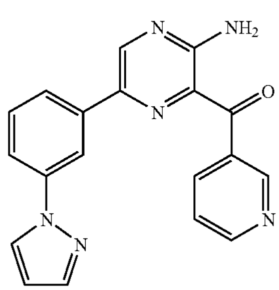 | 343 |
| 30 | 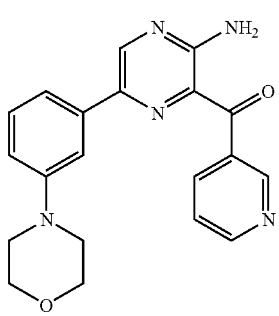 | 362 |
TABLE 1-continued
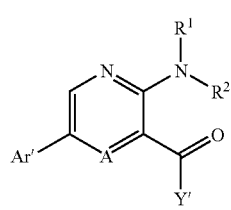
| Ex. | Structure | [M + H]+ |
|---|---|---|
| 31 | 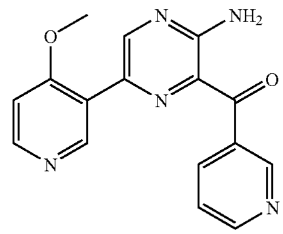 | 308 |
| 32 | 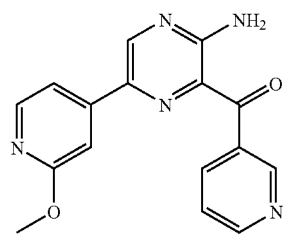 | 308 |
| 33 | 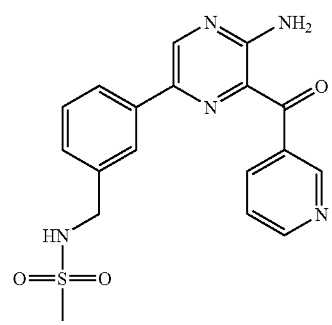 | 384/386 |
| 34 | 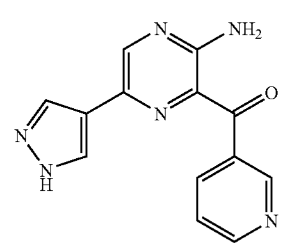 | 267 |
| 35 | 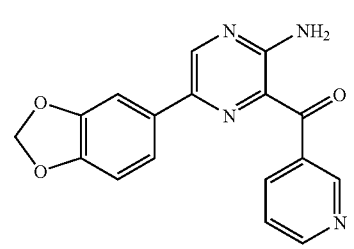 | 321 |

TABLE 1-continued

![Ia structure]

| Ex. | Structure | [M + H]⁺ |
|---|---|---|
| 36 | (3-trifluoromethoxyphenyl pyrazine with pyridin-3-yl ketone) | 361 |
| 37 | (3-(morpholinocarbonyl)phenyl pyrazine with pyridin-3-yl ketone) | 390 |
| 38 | (4-fluoro-3-(morpholinocarbonyl)phenyl pyrazine with pyridin-3-yl ketone) | 408 |
| 39 | (4-fluoro-3-(isopropylcarbamoyl)phenyl pyrazine with pyridin-3-yl ketone) | 380 |
| 40 | (4-methyl-3-(morpholinosulfonyl)phenyl pyrazine with 4-chlorobenzoyl) | 473 |
| 41 | (methyl-substituted pyrazine with 4-methyl-3-(morpholinosulfonyl)phenyl and benzoyl) | 453 |
| 42 | (4-methyl-3-(morpholinosulfonyl)phenyl pyrazine with benzoyl) | 439 |
| 43 | (3-(cyclopropylsulfamoyl)phenyl pyrazine with benzoyl) | 395 |

TABLE 1-continued

| Ex. | Structure | [M + H]+ |
|---|---|---|
| 44 | | 475 |
| 45 | | 443 |
| 46 | | 484 |
| 47 | | 316 |
| 48 | 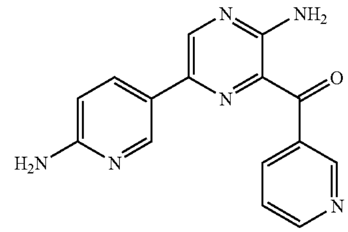 | 293 |
| 49 | 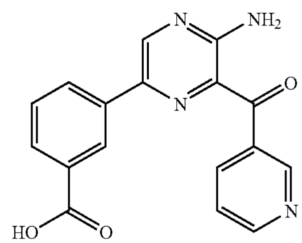 | 321 |
| 50 | 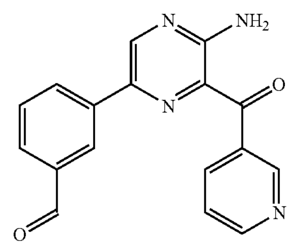 | 305 |
| 51 | 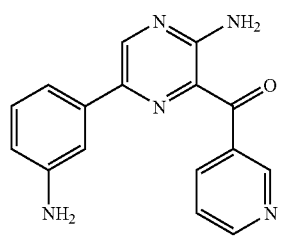 | 292 |
| 52 | 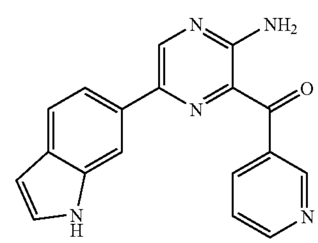 | 316 |

TABLE 1-continued
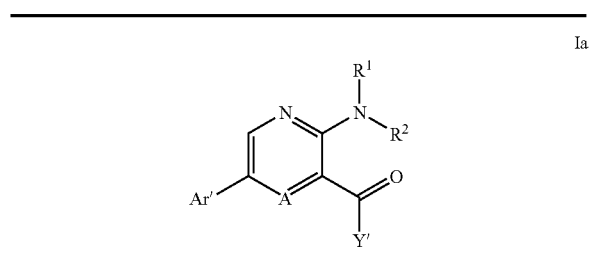
| Ex. | Structure | [M + H]+ |
|---|---|---|
| 53 | 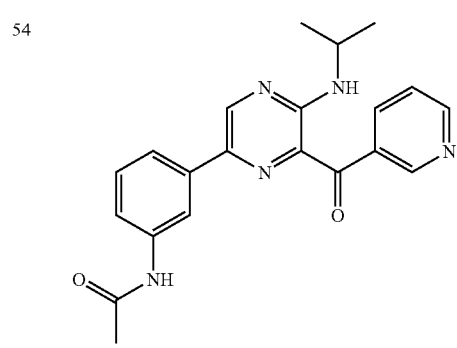 | 392 |
| 54 | 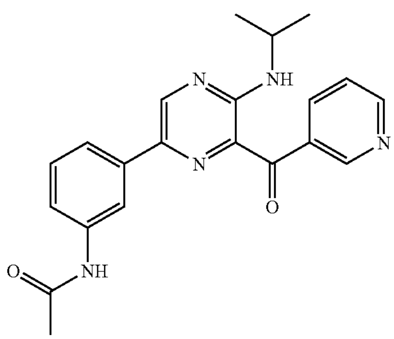 | 376 |
| 55 | 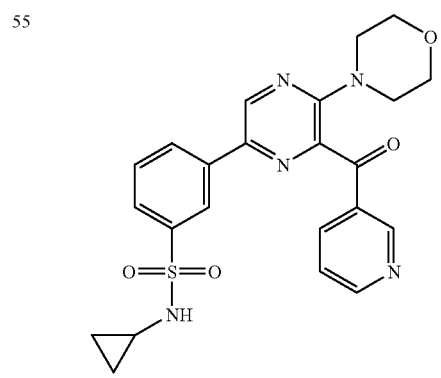 | MNa+ 488 |
TABLE 1-continued
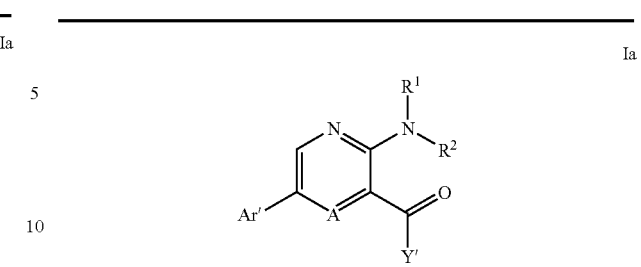
| Ex. | Structure | [M + H]+ |
|---|---|---|
| 56 | 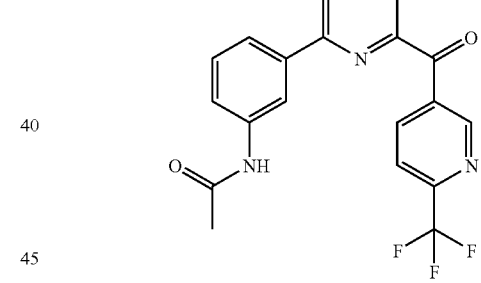 | MNa+ 476 |
| 57 | 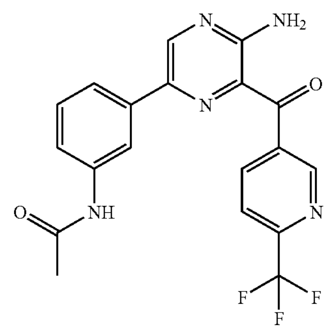 | MNa+ 424 |
| 58 | 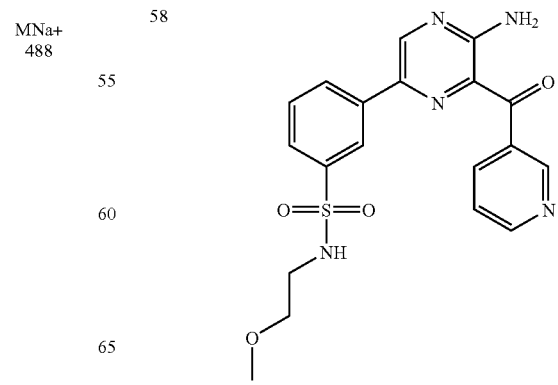 | 414 |

TABLE 1-continued

Ia

| Ex. | Structure | [M + H]+ |
|---|---|---|
| 59 | | 488 |
| 60 | | 494 |
| 61 | | 432 |
| 62 | | 360 |
| 63 | 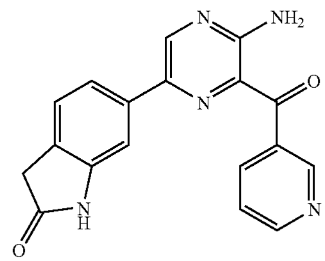 | 332 |
| 64 | 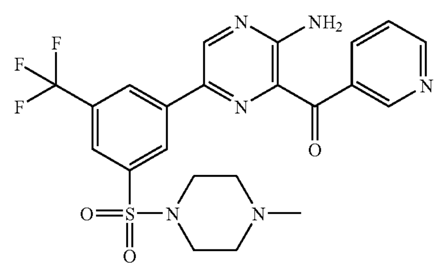 | 507 |
| 65 | 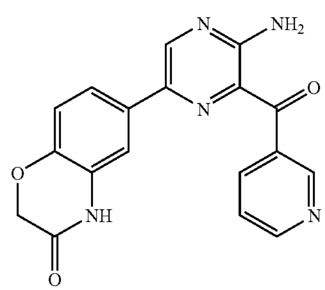 | 348 |
| 66 | 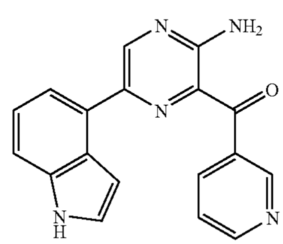 | 316 |
| 67 | 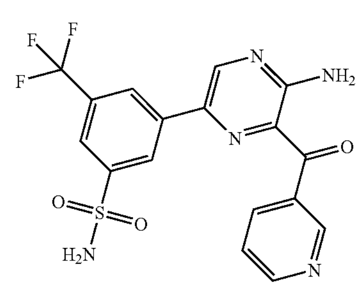 | 424 |

TABLE 1-continued
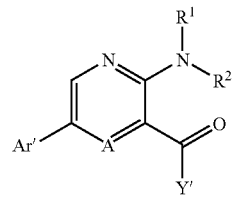
| Ex. | Structure | [M + H]⁺ |
|---|---|---|
| 68 | 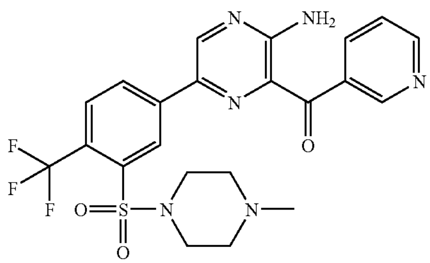 | 507 |
| 69 | 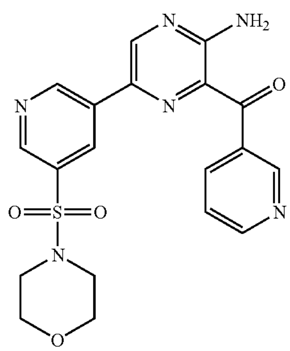 | 427 |
| 70 | 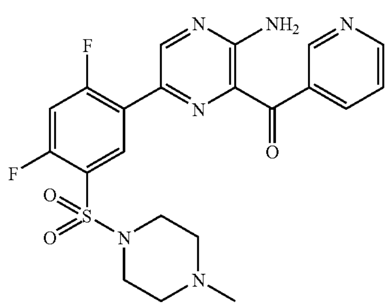 | 475 |
| 71 | 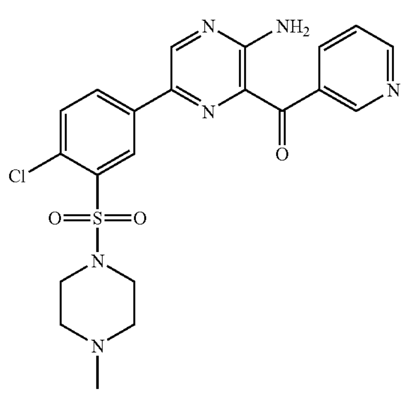 | 473 |
TABLE 1-continued
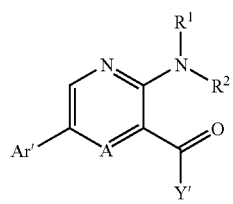
| Ex. | Structure | [M + H]⁺ |
|---|---|---|
| 72 | 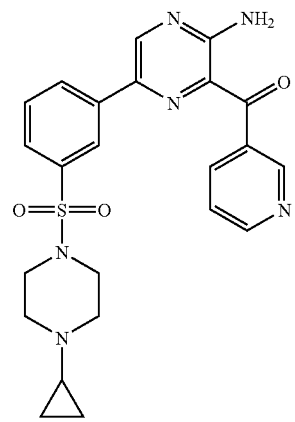 | 465 |
| 73 | 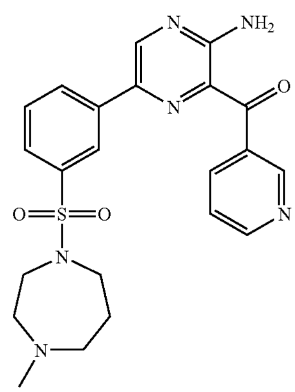 | 453 |
| 74 | 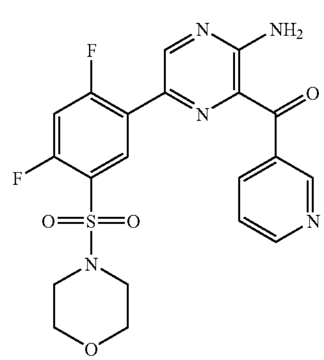 | 462 |

TABLE 1-continued

| Ex. | Structure | [M + H]⁺ |
|---|---|---|
| 75 | | 469 |
| 76 | | 482 |
| 77 | | 410 |
| 78 | 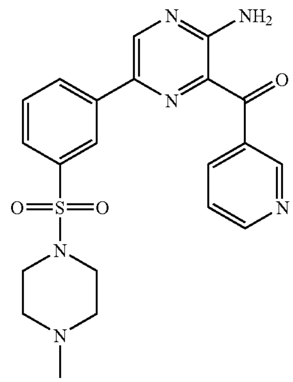 | 439 |
| 79 | 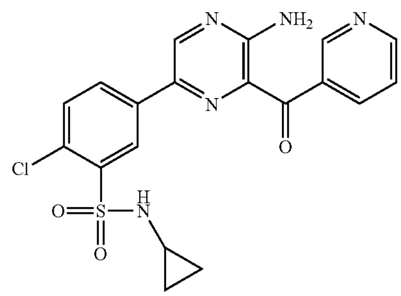 | 430 |
| 80 | 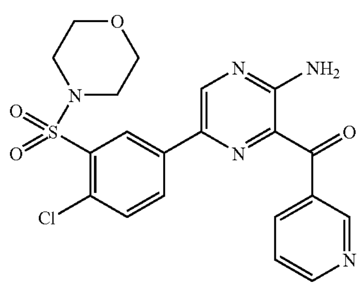 | 460 |
| 81 | 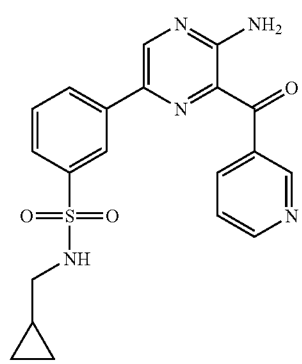 | 410 |

TABLE 1-continued

Structure Ia

| Ex. | Structure | [M + H]+ |
|---|---|---|
| 82 | 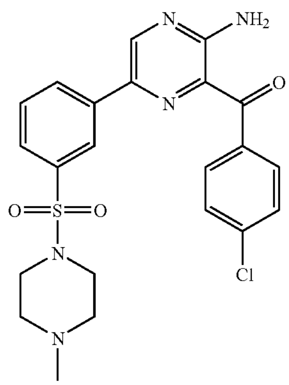 | 472/474 |
| 83 | 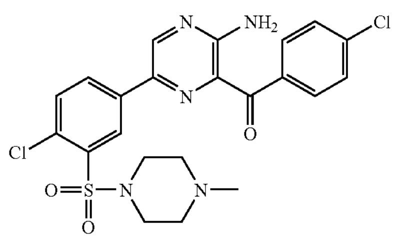 | 506 |
| 84 | 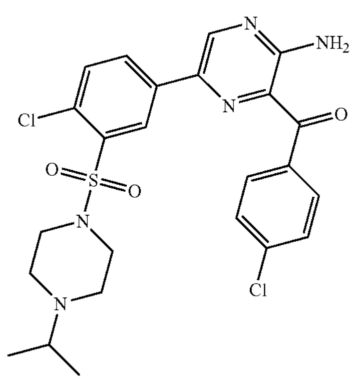 | 534 |
| 85 | 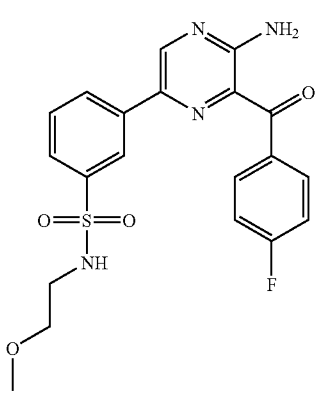 | 431 |
| 86 | | 441/443 |
| 87 | | 403 |
| 88 | | 450 |
| 89 | | 394 |

TABLE 1-continued
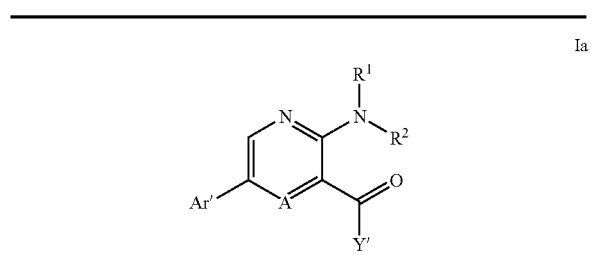
| Ex. | Structure | [M + H]+ |
|---|---|---|
| 90 | 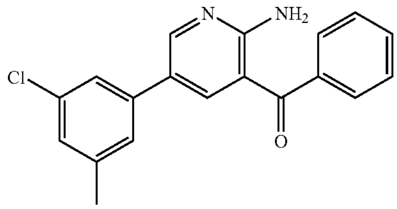 | 323 |
| 91 | 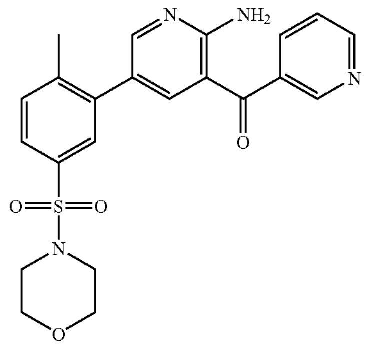 | 439 |
| 92 | 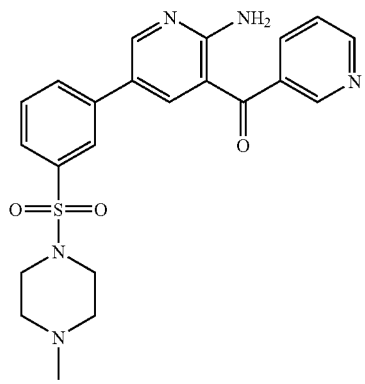 | 438 |
| 93 | 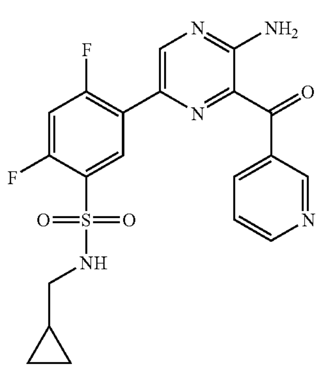 | 446 |
TABLE 1-continued
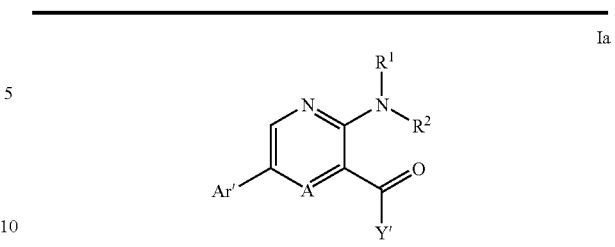
| Ex. | Structure | [M + H]+ |
|---|---|---|
| 94 | 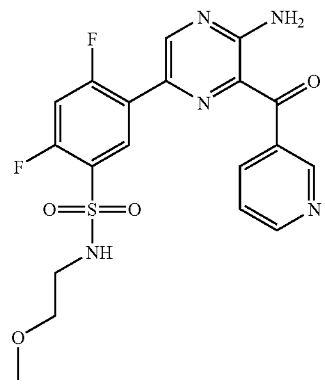 | 450 |
| 95 | 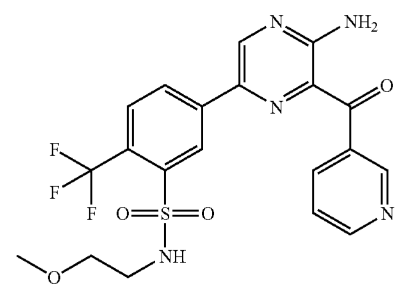 | 482 |
| 96 | 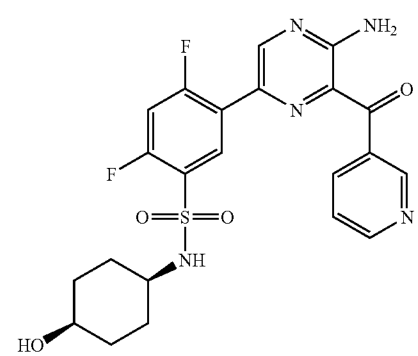 | 490 |
| 97 | 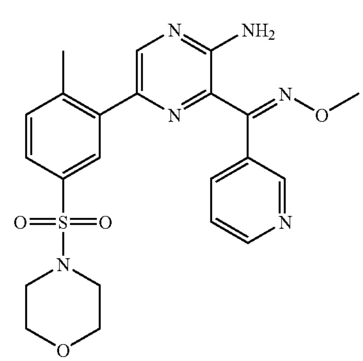 | 469 |

TABLE 1-continued
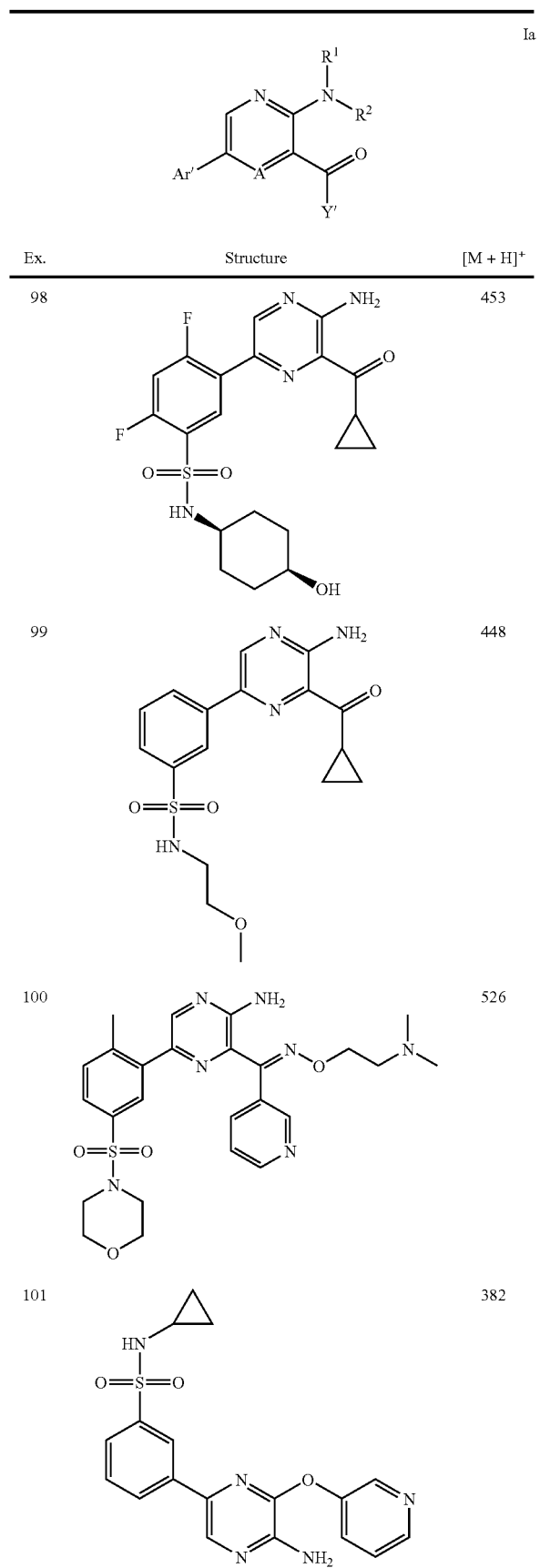
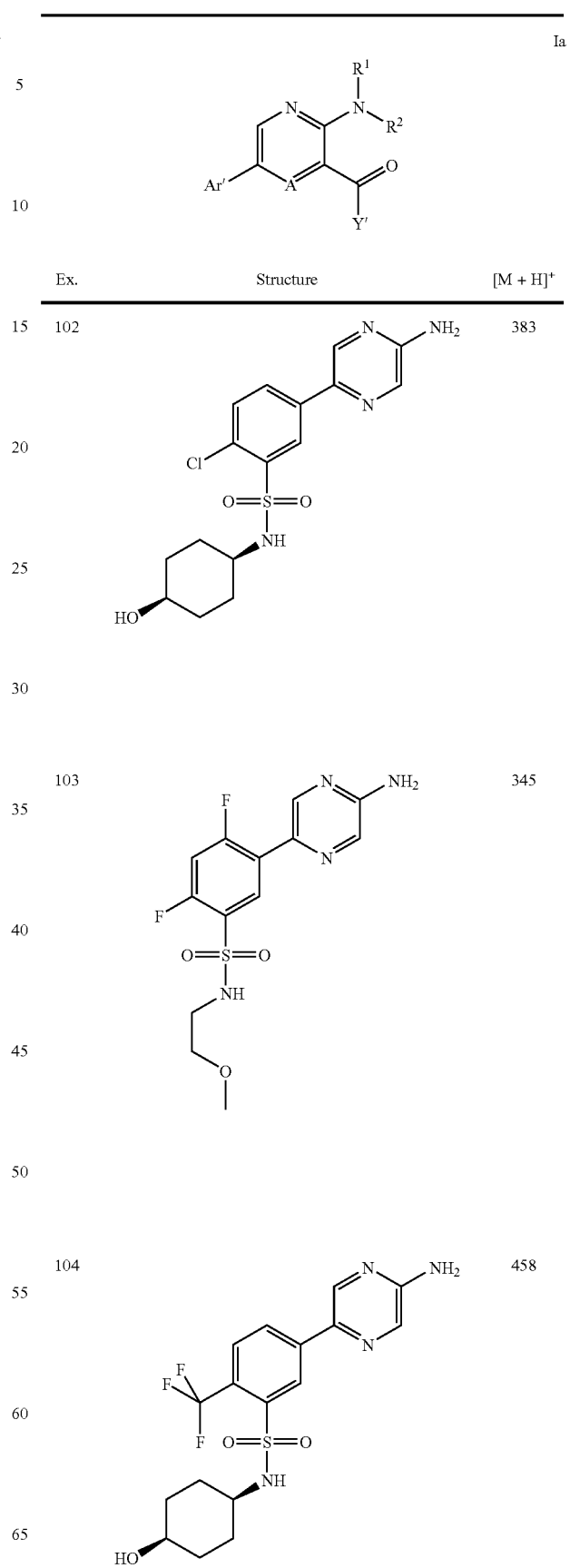

TABLE 1-continued

| Ex. | Structure | [M + H]⁺ |
|---|---|---|
| 105 | | 426 |
| 106 | | 448 |
| 107 | | 498 |
| 108 | 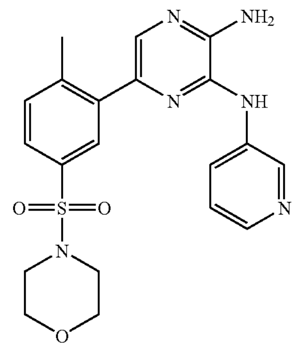 | 427 |
| 109 | 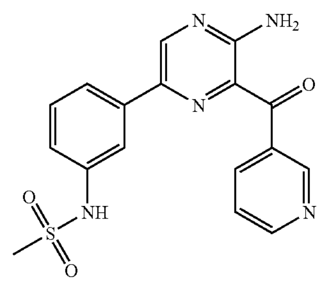 | 370 |
| 110 | 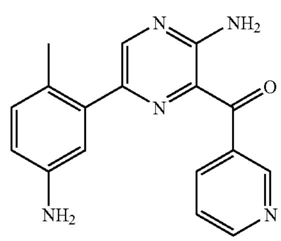 | 306 |
| 111 | 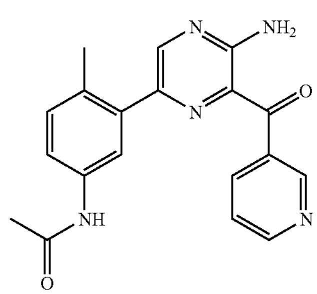 | 348 |

General Conditions:

Mass spectra are run on LCMS systems using electrospray ionization. These are either Agilent 1100 HPLC/Micromass Platform Mass Spectrometer combinations or Waters Acquity UPLC with SQD Mass Spectrometer. [M+H]⁺ and [M+Na]⁺ refers to mono-isotopic molecular weights.

NMR spectra are run on open access Bruker AVANCE 400 NMR spectrometers using ICON-NMR. Spectra are measured at 298K and are referenced using the solvent peak.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

In addition various trade reagents and materials available from have been utilized. Such reagents and materials include: Isolute™ (available from Biotage] and can be readily obtained from the suppliers indicated.

Abbreviations:

In the Experimental Section the following abbreviations have been used:

DMF dimethyl-formamide
THF tetrahydrofuran
MeOH methanol
DCM dichloromethane
DME dimethoxyethane
EtOAc ethyl acetate
EtOH ethanol
MeOH methanol
LCMS liquid chromatographic mass spectroscopy
NMR nuclear magnetic resonance
Pd(dppf) $Cl_2$ [1,1'-Bis(diphenylphosphino)ferrocene]dichloropalladium(II)
TFA trifluoroacetic acid
HPLC high performance liquid chromatography
HATU O-(7-Azabenzotriazol-1-yl)-N,N,N',N'-tetramethyluronium hexafluorophosphate
MeCN acetonitrile
EDC.HCl N-(3-Dimethylaminopropyl)-N'-ethylcarbodiimide hydrochloride
HOBt 1-Hydroxybenzotriazole
TMEDA N,N,N',N'-Tetramethylethylenediamine
br broad
s singlet
m multiplet
d doublet
dd doublet of doublets
t triplet Referring to the examples that follow, compounds of the preferred embodiments are synthesized using the methods described herein, or other methods, which are known in the art.

It is understood that the invention is not limited to the embodiments set forth herein for illustration, but embraces all such forms thereof as come within the scope of the above disclosure.

Preparation of Final Compounds

Example 1

[3-Amino-6-(6-amino-5-trifluoromethyl-pyridin-3-yl)-pyrazin-2-yl]-pyridiny-3-yl-methanone To a stirred suspension of (3-Amino-6-bromo-pyrazin-2-yl)-pyridin-3-yl-methanone (Intermediate AA) (0.10 g, 0.37 mmol) and 5-(4,4,5,5-Tetramethyl-[1,3,2]-dioxaborolan-2-yl)-3-trifluoromethyl-pyridin-2-ylamine (Intermediate K) (0.115 g, 0.40 mmol) in 2M $Na_2CO_3$ (1 ml) is added DME (3 ml) and Pd(dppf)$Cl_2$.DCM (0.027 g, 0.037 mmol). The resulting red suspension is heated at 120° C. for 15 hours. The crude reaction mixture is purified by reverse phase chromatography (Isolute™ C18, 0-100% MeCN in water −0.1% TFA) to afford the title compound as a yellow solid. $^1$H NMR (400 MHz, DMSO-d6) δ 9.10 (1H, d), 9.02 (1H, s), 8.08 (1H, dd), 8.78 (1H, d), 8.36 (1H, dt), 8.20 (1H, d), 8.02 (2H, br s), 7.61 (1H, ddd), 6.76 (2H, br s). MS m/z 362.0 [M+2H]$^+$ Examples 2-39

These compounds namely,

{3-Amino-6-[2-methyl-5-(morpholine-4-sulfonyl)-phenyl]pyrazin-2-yl}-pyridin-3-yl-methanone (Ex. 2), $^1$H NMR (400 MHz, DMSO-d6) δ 9.14 (1H, m), 8.79 (1H, dd), 8.75 (1H, s), 8.30 (1H, dt), 8.18 (2H, s), 7.78 (1H, d), 7.71 (1H, m), 7.66 (1H, m), 7.60 (1H, ddd), 3.70 (4H, t), 2.91 (4H, t), 2.51 (3H, s). MS m/z 440 [M+H]$^+$ N-{5-[5-Amino-6-(pyridine-3-carbonyl)-pyrazin-2-yl]-2-chloro-pyridin-3-yl}-benzenesulfonamide (Ex. 3), $^1$H NMR (400 MHz, DMSO-d6) δ 10.37 (1H, s), 9.05 (1H, d), 9.04 (1H, s), 8.82 (1H, dd), 8.79 (1H, d), 8.188 (2H, s), 8.181 (1H, d,), 7.62-757 (4H, m), 7.51-7.47 (2H, m); MS m/z 467 [M+H]$^+$

[3-Amino-6-(3-methznesulfonyl-phenyl)-pyrazin-2-yl]-pyridin-3-yl-methanone (Ex. 4), $^1$H NMR (400 MHz, DMSO-d6) δ 9.15 (1H, s), 9.13 (1H, m), 8.83 (1H, dd), 7.44 (1H, m), 8.41 (1H, m), 8.25 (1H, dt), 8.17 (2H, br s), 7.71 (1H, dt), 7.74 (1H, t), 7.66 (1H, dd). MS m/z 355 [M+H]$^+$ {3-Amino-6-[3-(pyrrolidine-1-sulfonyl)-phenyl]-pyrazin-2-yl}-pyridin-3-yl-methanone (Ex. 5), $^1$H NMR (400 MHz, DMSO-d6) δ 9.11 (1H, s), 9.06 (1H, d), 8.78 (1H, dd), 8.32 (1H, dt), 8.26 (1H, dt), 8.21 (1H, m), 8.14 (2H, s), 7.77 (1H, m), 7.71 (1H, t), 7.56 (1H, ddd), 3.11 (4H, t), 1.63 (4H, m). MS m/z 410 [M+H]$^+$

[3-Amino-6-(4-chloro-3-methyl-phenyl)-pyrazin-2-yl]-pyridin-3-yl-methanone (Ex. 6), $^1$H NMR (400 MHz, DMSO-d6) δ 9.09 (1H, d), 9.02 (1H, s), 8.79 (1H, dd), 8.31 (1H, dt), 8.07 (2H, s), 7.92 (1H, d), 7.73 (1H, dd), 7.60 (1H, ddd), 7.48 (1H, d), 2.36 (3H, s). MS m/z 325 [M+H]$^+$ N'-{3-[5-amino-6-(pyridine-3-carbonyl)-pyrazin-2-yl]-phenyl}-N,N-dimethyl-sulfamide (Ex. 7) $^1$H NMR (400 MHz, DMSO-d6) δ 9.96 (1H, s), 9.06 (1H, d), 8.90 (1H, s), 8.78 (1H, dd), 8.36 (1H, dt), 8.05 (2H, s), 7.70 (1H, t), 7.61 (1H, m), 7.58 (1H, ddd), 7.38 (1H, t), 7.19 (1H, m), 2.64 (6H, s). MS m/z 399 [M+H]$^+$

[3-Amino-6-(5-methanesulfonyl-pyridin-3-yl)-pyrazin-2-yl]-pyridin-3-yl-methanone (Ex. 8), $^1$H NMR (400 MHz, DMSO-d6) δ 9.40 (1H, d), 9.22 (1H, s), 9.09 (1H, s), 9.04 (1H, d), 8.80 (1H, d), 8.71 (1H, t), 8.36 (1H, dt), 8.24 (2H, s), 7.59 (1H, dd), 3.35 (3H, s). MS m/z 356 [M+H]$^+$

[3-Amino-6-(3-chloro-5-methyl-phenyl)-pyrazin-2-yl]-pyridin-3-yl-methanone (Ex. 9), $^1$H NMR (400 MHz, DMSO-d6) δ 8.93 (1H, d), 8.63 (1H, dd), 8.49 (1H, s), 8.13 (1H, dt), 7.95 (2H, s), 7.45 (1H, ddd), 7.40 (1H, d), 7.29 (1H, m), 7.27 (1H, m), 2.18 (3H, s). MS m/z 325 [M+H]$^+$ 3-[5-Amino-6-(pyridine-3-carbonyl)-pyrazin-2-yl]-N-cyclopropyl-benzenesulfonamide (Ex. 10) $^1$H NMR (400 MHz, DMSO-d6) δ 9.15 (2H, s), 8.86 (1H, d), 8.42 (1H, d), 8.39 (1H, s), 8.28 (1H, s), 8.21 (2H, s), 7.96 (1H, s), 7.86 (1H, d), 7.78 (1H, t), 7.64 (1H, dd), 2.19 (1H, m), 0.51 (2H, m), 0.44 (2H, m). MS m/z 396 [M+H]$^+$

[3-Amino-6-(3,4-dichloro-phenyl)pyrazin-2-yl]-pyridin-3-yl-methanone (Ex. 11), $^1$H NMR (400 MHz, DMSO-d6) δ 9.09 (2H, m), 8.07 (1H, dd), 8.29 (1H, dt), 8.13 (2H, m), 7.89 (1H, dd), 7.73 (1H, d), 7.59 (1H, ddd). MS m/z 345/347 [M+H]$^+$ Cyclopropanesulfonic acid {3-[5-amino-6-(pyridine-3-carbonyl)-pyrazin-2-yl]-4-methyl-phenyl}-amide (Ex. 12), $^1$H NMR (400 MHz, DMSO-d6) δ 9.08 (1H, d), 8.77 (1H, dd), 8.59 (1H, s), 8.31 (1H, dt), 8.09 (2H, s), 7.58 (1H, ddd), 7.37 (1H, d), 7.28 (1H, d), 7.22 (1H, dd), 2.60 (1H, m), 2.29 (3H, s), 0.95 (4H, m). MS m/z 410 [M+H]$^+$ 5-[5-Amino-6-(pyridine-3-carbonyl)-pyrazin-2-yl]-2-chloro-N-phenyl-benzenesulfonamide (Ex. 13) $^1$H NMR (400 MHz, DMSO-d6) δ 10.67 (1H, s), 9.11 (1H, d), 9.10 (1H, s), 8.73 (1H, dd), 8.59 (1H, d), 8.42 (1H, dt), 8.23 (2H, br s), 8.21 (1H, dd), 7.76 (1H, d), 7.64 (1H, dd), 7.22 (2H, t), 7.17 (2H, d), 7.01 (1H, t) (; MS m/z 466 [M+H]$^+$

[3-Amino-6-(4-chloro-3-trifluoromethyl-phenyl)-pyrazin-2-yl]-pyridin-3-yl-methanone (Ex. 14), $^1$H NMR (DMSO-d6) δ 9.16 (1H, s), 9.10 (1H, br s), 8.83 (1H, d), 8.37 (1H, dt), 8.30 (1H, d), 8.24 (1H, dd), 8.18 (2H, br s), 7.83 (1H, d), 7.64 (1H, dd); MS m/z 379 [M+H]$^+$

[3-Amino-6-(3-chloro-phenyl)-pyrazin-2-yl]-pyridin-3-yl-methanone (Ex. 15), $^1$H NMR (DMSO-d6) δ 9.14 (1H, d), 9.08 (1H, s), 8.84 (1H, dd), 8.35 (1H, dt), 8.13 (2H, br s), 7.99-7.95 (2H, m), 7.66 (1H, ddd), 7.59-7.55 (2H, m); MS m/z 311 [M+H]$^+$

[3-Amino-6-(3-amino-4-chloro-phenyl)-pyrazin-2-yl]-pyridin-3-yl-methanone (Ex. 16), $^1$H NMR (DMSO-d6) δ 9.07 (1H, d), 8.83 (1H, s), 8.78 (1H, dd), 8.33 (1H, dt), 8.01 (2H, br s), 7.62 (1H, ddd), 7.28-7.25 (3H, m), 7.08 (1H, d), 5.42 (2H br s; MS m/z 326 [M+H]$^+$ {3-Amino-6-[4-methoxy-3-morpholine-4-sulfonyl)-phenyl]-pyrazin-2-yl}-pyridin-3-yl-methanone (Ex. 17), $^1$H NMR (DMSO-d6) δ 9.06 (1H, d), 9.02 (1H, s), 8.79 (1H, dd), 8.37 (1H, dt), 8.23 (1H, d), 8.21 (2H, dd), 8.06 (2H, br s), 7.58 (1H, ddd), 7.38 (1H, d), 7.07 (N14-H t), 3.90 (3H, s) 3.59 (4H, t), 3.06 (4H, t); MS m/z 456 [M+H]$^+$

[3-Amino-6-(6-chloro-pyridin-3-yl)-pyrazin-2-yl]-pyridin-3-yl-methanone (Ex. 18), $^1$H NMR (DMSO-d6) δ 9.12 (1H, d), 9.10 (1H, s), 8.93 (1H, d), 8.82 (1H, dd), 8.38 (1H, dt), 8.29 (1H, dd), 8.17 (2H, br s), 7.67 (1H, ddd), 7.63 (1H, d); MS m/z 312/314 [M+H]$^+$ 1-{3-[5-Amino-6-(pyridine-3-carbonyl)-pyrazin-2-yl]-phenyl}-ethanone (Ex. 19), $^1$H NMR (400 MHz, DMSO-d6) δ 9.13 (1H, s), 9.12 (1H, m), 8.79 (1H, dd), 8.48 (1H, t), 8.35 (1H, dt), 8.18 (1H, dt), 8.11 (2H, s), 7.93 (1H, dt), 7.60 (2H, m), 2.61 (3H, s). MS m/z 319 [M+H]$^+$

[3-amino-6-(5-triflouromethyl-pyridin-3-yl)-pyrazin-2-yl]-pyridin-3-yl-methanone (Ex. 20), $^1$H NMR (400 MHz, DMSO-d6) δ 9.38 (1H, d), 9.22 (1H, s), 9.10 (1H, d), 8.95 (1H, d), 8.80 (1H, dd), 8.58 (1H, t), 8.33 (1H, dt), 8.22 (2H, br s), 7.60 (1H, dd); MS m/z 346 [M+H]$^+$

[3-Amino-6-(3-furan-2-yl-phenyl-pyrazin-2-yl]-pyridin-3-yl-methanone (Ex. 21), $^1$H NMR (400 MHz, DMSO-d6) δ 9.14 (1H, d), 9.11 (1H, s), 8.28 (1H, dd), 8.36 (1H, dt), 8.25 (1H, t), 8.09 (2H, s), 7.85 (1H, d), 7.79 (1H, d), 7.71 (1H, d), 7.94 (1H, ddd), 7.51 (1H, t), 7.01 (1H, d), 6.65 (1H, dd); MS m/z 343 [M+H]$^+$ 5-[5-Amino-6-(pyridine-3-carbonyl)-pyrazine-2-yl]-2-chloro-N,N-dimethyl-benzamide (Ex. 22), $^1$H NMR (400 MHz, DMSO-d6) δ 9.08 (2H, m), 8.78 (1H, dd), 8.29 (1H, dt), 8.10 (2H, s), 7.92 (1H, d), 7.90 (1H, s), 7.59 (1H, m), 7.57 (1H, ddd), 3.03 (3H, s), 2.80 (3H, s). MS m/z 382 [M+H]$^+$

[3-Amino-6-(2-chloro-pyridin-4-yl)-pyrazin-2-yl]-pyridin-3-yl-methanone (Ex. 23), $^1$H NMR (400 MHz, DMSO-d6) δ 9.19 (1H, s), 9.11 (1H, d), 8.82 (1H, dd), 8.46 (1H, d), 8.35 (1H, dt), 8.31 (2H, br s), 7.95 (1H, dd), 7.86 (1H, dd), 7.66 (1H, dd). MS m/z 312 [M+H]$^+$ 3-[5-Amino-6-(pyridine-3-carbonyl)-pyrazin-2-yl]-N-benzyl-4-methyl-benzene sulphonamide (Ex. 24), $^1$H NMR (400 MHz, DMSO-d6) δ 9.04 (1H, d), 8.62 (1H, dd), 8.46 (1H, s), 8.23 (1H, dt), 8.03 (2H, s), 7.81 (1H, d), 7.72 (1H, br), 7.44-7.39 (3H, m), 7.19 (3H, m), 7.08 (2H, m), 3.78 (2H, s), 2.40 (3H, s). MS m/z 460 [M+H]$^+$

[3-Amino-6-(1-benzyl-1H-pyrazol-4-yl)-pyrazin-2-yl]-pyrdin-3-yl-methanone (Ex. 25), $^1$H NMR (400 MHz, DMSO-d6) δ 9.07 (1H, dd), 8.76 (1H, dd), 8.74 (1H, s), 8.31 (1H, dt), 8.22 (1H, s), 7.90 (H2, s), 7.87 (1H, s), 7.58 (1H, ddd), 7.37-7.24 (5H, m), 5.37 (2H, s); MS m/z 357 [M+H]$^{30}$ 3-[5-Amino-6-(pyridine-3-carbonyl)-pyrazin-2-yl]-4-fluoro-N-methyl-benzamide (Ex. 26), $^1$H NMR (400 MHz, DMSO-d6) δ 9.12 (1H, s), 8.79 (2H, dd), 8.47 (1H, m), 8.39 (1H, m), 8.21 (1H, dd), 8.14 (2H, s), 7.87 (1H, m), 7.59 (1H, dd), 7.43 (1H, dd), 2.79 (3H, d). MS m/z 352 [M+H]$^+$

[3-Amino-6-(6-hydroxy-pyridin-3-yl)-pyrazin-2-yl]-pyridin-3-yl-methanone (Ex. 27), $^1$H NMR (400 MHz, DMSO-d6) δ 12.00 (1H, br), 9.13 (1H, s), 8.91 (1H, s), 8.85 (1H, d), 8.42 (1H, dt), 7.99 (2H, m), 7.91 (1H, d), 7.73 (1H, dd), 6.43 (1H, d). MS m/z 294 [M+H]$^+$ {3-Amino-6-[5-morpholine-4-carbonyl)-pyridin-3-yl]-pyrazin-2-yl}-pyridin-3-yl-methanone (Ex. 28), $^1$H NMR (400 MHz, DMSO-d6) δ 9.17 (1H, d), 9.13 (1H, s), 9.12 (1H, m), 8.79 (1H m), 8.61 (1H, d), 8.30 (1H, dt), 8.26 (1H, t), 8.17 (2H, s), 7.60 (1H, dd), 3.71-3.45 (6H, br d), 3.35 (2H, br). MS m/z no-ion [M+H]+

[3-Amino-6-(3-pyrazol-1yl-phenyl)-pyrazin-2-yl]-pyridin-3-yl-methanone (Ex. 29), $^1$H NMR (400 MHz, DMSO-d6) δ 9.14-9.13 (2H, m), 8.80 (1H, dd), 8.55 (1H, d), 8.37 (1H, t), 8.37 (2H, dt), 8.11 (2H, s), 7.86-7.82 (2H, m), 7.78 (1H, d), 7.62-7.55 (2H, m), 6.60 (1H, dd); MS m/z 343[M+H]$^+$

[3-Amino-6-(3-morpholin-4-yl-phenyl)-pyrazin-2-yl]-pyridin-3-yl-methanone (Ex. 30), $^1$H NMR (400 MHz, DMSO-d6) δ 9.12 (1H, d), 9.03 (1H, s), 8.80 (1H, dd), 8.36 (1H, dt), 8.04 (2H, s), 7.63 (1H, dd), 7.47 (1H, s), 7.40 (1H, d), 7.30 (1H, t), 6.98 (1H, dd), 3.77 (4H, t), 3.13 (4H, t); MS m/z 362 [M+H]$^+$

[3-Amino-6-(4-methoxy-pyridin-3-yl)-pyrazin-2-yl]-pyridin-3-yl-methanone (Ex. 31), $^1$H NMR (400 MHz, DMSO-d6) δ 9.11 (1H, d), 8.87 (1H, s), 8.76 (1H, dd), 8.71 (2H, s), 8.69 (1H, d), 8.32 (1H, dt), 8.18 (2H, br s), 7.58 (2H, m), 4.12 (3H, s). MS m/z 308 [M+H]$^+$

[3-Amino-6-(2-methoxy-pyridin-4-yl)-pyrazin-2-yl]-pyridin-3-yl-methanone (Ex. 32), $^1$H NMR (400 MHz, DMSO-d6) δ 9.12 (2H, s), 8.83 (1H, s), 8.35 (1H, m), 8.23 (3H, m), 7.66 (1H, dd), 7.48 (1H, d), 7.29 (1H, d), 3.88 (3H, s). MS m/z 308 [M+H]$^+$ N-{3-[5-Amino-6-(pyridine-3-carbonyl)-pyrazin-2-yl]-benzyl}-methansulfonamide (Ex. 33), $^1$H NMR (400 MHz, DMSO-d6) δ 9.16 (1H, s), 9.08 (1H, s), 8.86 (1H, m), 8.43 (1H, m), 8.14 (2H, s), 7.98 (1H, s), 7.89 (1H, d), 7.69 (1H, dd), 7.64 (1H, s), 7.52 (1H, t), 7.44 (1H, t), 4.28 (2H, s), 2.94 (3H, s). MS m/z 384/386 [M+H]$^+$

[3-Amino-6-(1H-pyrazol-4-yl)-pyrazin-2-yl]-pyridin-3-yl-methanone (Ex. 34), $^1$H NMR (400 MHz, DMSO-d6) δ 9.16 (1H, s), 8.79 (2H, m), 8.42 (1H, d), 8.03 (2H, s), 7.93 (2H, s), 7.68 (1H, dd), 5.50-4.50 (1H, v br). MS m/z 267 [M+H]$^+$ (3-Amino-6-benzo[1,3]dioxol-5-yl-pyrazin-2-yl)-pyridin-3-yl-methanone (Ex. 35), $^1$H NMR (400 MHz, DMSO-d6) δ 9.09 (1H, d), 8.96 (1H, s), 8.77 (1H, dd), 8.28 (1H, dt), 7.99 (2H, s), 7.59 (1H, dd), 7.45 (1H, dd), 7.42 (1H, d), 7.00 (1H, d), 6.05 (2H, s). MS m/z 321 [M+H]$^+$

[3-Amino-6-(2-trifluoromethoxy-phenyl)-pyrazin-2-yl]-pyridin-3-yl-methanone (Ex. 36), $^1$H NMR (400 MHz, DMSO-d6) δ 9.13 (1H, d), 8.79 (1H, dd), 8.72 (1H, s), 8.33 (1H, dd), 8.17 (2H, s), 7.80 (1H, dd), 7.63-7.53 (4H, m). MS m/z 361 [M+H]$^+$ {3-Amino-6-[3-morpholine-4-carbonyl)-phenyl]-pyrazin-2-yl}-pyridin-3-yl-methanone (Ex. 37), $^1$H NMR (400 MHz, DMSO-d6) δ 9.11 (1H, d), 9.07 (1H, s), 8.79 (1H, dd), 8.30 (1H, dt), 8.08 (2H, bs), 8.00 (1H, bd), 7.91 (1H, bs), 7.60 (1H, ddd), 7.53 (1H, t), 7.41 (1H, d), 7.70-3.44 (4H, br hump); MS m/z 390 [M+H]$^+$ {3-Amino-6-[4-fluoro-3-(morpholine-4-carbonyl)-phenyl]-pyrazin-2-yl}-pyridin-3-yl-methanone (Ex. 38), $^1$H NMR (400 MHz, DMSO-d6) δ 9.09 (1H, d), 9.05 (1H, s), 8.78 (1H, dd), 8.28 (1H, dt), 8.07 (2H, s), 8.01-7.97 (1H, m), 7.93 (1H, dd), 7.58 (1H, ddd), 7.41 (1H, t), 3.50 (4H, t), 3.25 (4H, t). MS m/z 408 [M+H]$^+$ 3-[5-Amino-6-(pyridine-3-carbonyl)-pyrazin-2-yl]-4-fluoro-N-isopropyl-benzamide (Ex. 39), $^1$H NMR (400 MHz, DMSO-d6) δ 9.12 (1H, s), 8.81-8.78 (2H, m), 8.43 (1H, d), 8.25 (2H, dd), 8.15 (1H, bs), 7.88 (1H, bs), 7.60 (1H, t), 7.42 (1H, t), 7.53 (1H, t), 7.10 (N14-H, t), 4.13-4.04 (1H, br m), 1.18 (6H, d); MS m/z 380 [M+H]$^+$ are prepared by an analogous procedure to Example 1 by replacing 5-(4,4,5,5-tetramethyl-[1,3,2]-dioxaborolan-2-yl)-3-trifluoromethyl-pyridin-2-ylamine (Intermediate K) with the appropriate boronic acid or boronic ester. The compounds are recovered from reaction mixtures and purified using conventional techniques such as flash chromatography, filtration, recrystallisation and trituration.

Examples 40-46

These compounds, namely
{3-Amino-6-[2-methyl-5-(morpholine-4-sulfonyl)-phenyl]-pyrazin-2-yl}-(4-chloro-phenyl)-methanone (Ex. 40), $^1$H NMR (400 MHz, DMSO-d6) δ 8.65 (1H, s), 7.99 (2H, s), 7.90 (2H, d), 7.76 (1H, d), 7.64 (1H, dd), 7.57 (1H, d), 7.54 (2H, d), 3.61 (4H, t), 2.83 (4H, t), 2.44 (3H, s). MS m/z 473 [M+H]$^+$ {3-Amino-5-methyl-6-[2-methyl-5-(morpholine-4-sulfonyl)-phenyl]-pyrazin-2-yl}-phenyl-methanone (Ex. 41), $^1$H NMR (DMSO-6) δ 7.94 (2H, br s), 7.90-7.88 (2H, m), 7.75-7.72 (3H, m), 7.67 (1H, d), 7.63-7.58 (2H, m), 7.51-7.47 (2H, m), 3.70 (4H, t), 2.93 (4H, t), 2.31 (3H, s), 2.29 (3H, s); MS m/z 453 [M+H]$^+$ {3-Amino-6-[2-methyl-5-(morpholine-4-sulfonyl)-phenyl]-pyrazin-2-yl}-phenyl-methanone (Ex. 42), $^1$H NMR (400 MHz, DMSO-d6) δ 8.63 (1H, s), 7.95 (2H, s), 7.86 (2H, m), 7.76 (1H, d), 7.63 (1H, dd), 7.60-7.55 (2H, m), 7.47 (2H, m), 3.59 (4H, t), 2.82 (4H, t), 2.44 (3H, s). MS m/z 439 [M+H]$^+$ 3-(5-Amino-6-benzoyl-pyrazin-2-yl)-N-cyclopropyl-benzenesulfonamide (Ex. 43), $^1$H NMR (DMSO-6) δ 9.03 (1H, s), 8.36 (1H, t), 8.23 (1H, t), 8.01-7.97 (4H, m), 7.88 (1H, d), 7.78 (1H, d), 7.71-7.62 (2H, m), 7.54 (2H, t), 2.12-2.07 (1H, m), 0.44-0.34 (4H, m); MS m/z 395 [M+H]$^+$ {3-Amino-6-[2-methyl-5-(morpholine-4-sulfonyl)-phenyl]-pyrazin-2-yl}-(3,5-difluoro-phenyl)-methanone (Ex. 44), $^1$H NMR (DMSO-d6) δ 8.66 (1H, s), 8.05 (2H, s), 7.74 (1H, d), 7.65 (1H, dd), 7.59-7.47 (4H, m), 3.61 (4H, t), 2.83 (4H, t), 2.43 (3H, s). MS m/z 475 [M+H]$^+$ {3-Amino-6-[3-(morpholine-4-fulxonyl)-[phenyl]-pyrazin-2-yl}-(4-fluoro-phenyl)-methanone (Ex. 45), $^1$H NMR (DMSO-6) δ 9.09 (1H, s), 8.32 (1H, d), 8.18 (1H, s), 8.07-8.04 (4H, m), 7.77-7.70 (2H, m), 7.38-7.32 (2H, m), 3.63 (4H, t), 2.86 (4H, t); MS m/z 443 [M+H]$^+$ {3-(2-methoxy-ethylamino)-6-[3-morpholine-4-sulfonyl)-phenyl]-pyrazin-2-yl}-pyridin-3-yl-methanone (Ex. 46), $^1$H NMR (400 MHz, DMSO-d6) δ 9.25 (1H, s), 9.10 (1H, m), 8.79 (1H, s), 8.71 (1H, d), 8.37 (1H, d), 8.13 (1H, s), 8.01 (1H, d), 7.67 (1H, d), 7.58 (1H, t), 7.48 (1H, d), 3.83 (2H, m), 3.68 (4H, m), 3.62 (2H, t), 3.39 (3H, s), 2.94 (4H, m). MS m/z 484 [M+H]$^+$ are prepared by an analogous procedure to Example 1 by replacing 5-(4,4,5,5-Tetramethyl-[1,3,2]-dioxaborolan-2-yl)-3-trifluoromethyl-pyridin-2-ylamine (Intermediate K) with the appropriate boronic acid or boronic ester and (3-Amino-6-bromo-pyrazin-2-yl)-pyridin-3-yl-methanone (Intermediate AA) with the appropriate pyrazine bromide. The pyrazine bromides are prepared as outlined in section 'Preparation of intermediate compounds'.

Example 47

[3-Amino-6-(1H-indol-5-yl)-pyrazin-2-yl]-pyridin-3-yl-methanone

Bis(benzonitrile)palladium(II)chloride (5.2 mg, 0.013 mmol) and 1,4-bis(diphenylphosphino)butane (6.7 mg, 0.015 mmol) in toleune (0.6 ml) are stirred for 20 minutes. (3-Amino-6-bromo-pyrazin-2-yl)-pyridin-3-yl-methanone (Intermediate AA) (0.075 g, 0.27 mmol), 5-indoylboronic acid (0.056 g, 0.35 mmol), ethanol (0.36 ml) and 1M Na$_2$CO$_3$ (0.65 ml) are added and the reaction is heated using microwave radiation at 140° C. for 20 minutes. The mixture is diluted with EtOAc and sat. aq. NaHCO$_3$. The layers are separated and the aqueous layer is extracted with EtOAc. The combined organic extracts are dried (MgSO$_4$), and purified by preperative HPLC (0-100% MeCN in water −0.1% TFA) to yield the title compound as an orange solid. $^1$H NMR (400 MHz, DMSO-d6) δ 11.27 (1H, s), 9.21 (1H, s), 9.09 (1H, s), 8.86 (1H, dd), 8.39-8.41 (1H, dt), 8.19 (1H, s), 7.99 (2H, s), 7.65-7.73 (2H, m), 7.5 (1H, d), 7.44 (1H, t), 6.53 (1H, s). MS m/z 316 [M+H]$^+$ Examples 48-52

These compounds, namely
[3-Amino-6-(6-amino-pyridin-3-yl)-pyrazin-2-yl]-pyridin-3-yl-methanone (Ex. 48), $^1$H NMR (400 MHz, DMSO-d6) δ 9.06 (1H, dd), 8.87 (1H, s), 8.73-8.74 (1H, dd), 8.465 (1H, d), 8.24-8.27 (1H, dt), 7.90 (2H, s), 7.80-7.83 (1H, dd), 7.54-7.57 (1H, m), 6.46 (1H, d), 6.18 (2H, s); MS m/z 293 [M+H]$^+$ 3-[5-Amino-6-(pyridine-3-carbonyl)-pyrazin-2-yl]-benzoic acid (Ex. 49), $^1$H NMR (400 MHz, DMSO-d6) δ 9.07 (1H, d), 9.05 (1H, s), 8.75-8.77 (1H, dd), 8.44 (1H, s), 8.3-8.32 (1H, td), 8.11-8.14 (1H, d), 8.07 (2H, s), 7.89-7.91 (1H, d), 7.54-7.58 (2H, m). 7.89-7.91 (1H, d); MS m/z 321 [M+H]$^+$ 3-[5-Amino-6-(pyridine-3-carbonyl)-pyrazin-2-yl]-benzaldehyde (Ex. 50), $^1$H NMR (400 MHz, CDCl$_3$) δ 10.08 (1H, s), 9.33 (1H, d), 8.86 (1H, s), 8.81-8.82 (1H, d), 8.36-8.39 (2H, m), 8.15-8.17 (1H, d), 7.89-7.90 (1H, d), 7.64 (1H, t), 7.48-7.51 (1H, dd); MS m/z 305 [M+H]$^+$

[3-Amino-6-(3-amino-phenyl)-pyrazin-2-yl]-pyridin-3-yl-methanone (Ex. 51), $^1$H NMR (DMSO-d6) δ 9.05-9.06 (1H, d), 8.80 (1H, s), 8.74-8.75 (1H, dd), 8.29-8.31 (1H, dt), 7.96 (2H, s), 7.56-7.59 (1H, m), 7.01-7.08 (3H, m), 5.54-5.56 (1H, d), 5.13 (2H, s); MS m/z 292 [M+H]$^+$

[3-Amino-6-(1H-indol-6-yl)-pyrazin-2-yl]-pyridin-3-yl-methanone (Ex. 52), $^1$H NMR (DMSO-6) δ 11.25 (1H, s) 9.15 (1H, s), 9.02 (1H, s), 8.81 (1H, dd), 8.35-8.33 (1H, m), 7.95 (2H, br s), 7.90 (1H, s), 7.63-7.60 (3H, m), 7.39 (1H, t), 6.44 (1H, s); MS m/z 316 [M+H]$^+$ are prepared in an analogous manner to Example 47 by replacing 5-indoylboronic acid with the appropriate boronic acid. The compounds are recovered from reaction mixtures and purified using conventional techniques.

Example 53

N-{3-[5-(2-Methoxy-ethylamino)-6-(pyridine-3-carbonyl)-pyrazin-2-yl]phenyl}-acetamide Palladium(II)acetate (2.83 mg, 0.006 mmol) and 1,1-bis(diphenylphosphino)ferrocene (5.42 mg, 0.0095 mmol) are dissolved in DMF (2 ml) and the mixture is stirred at 50° C. for 10 min. The mixture is cooled to room temperature and 3-acetamidobenzene boronic acid (25.5 mg, 0.14 mmol), [6-bromo-3-(2-methoxy-ethylamino)pyrazin-2-yl]pyridin-2yl-methanone (Intermediate AC) (40 mg, 0.12 mmol) in DMF (1.5 ml) and triethylamine (24.9 µl, 0.18 mmol) are added. After stirring for 17 hours at 80° C. the solvent is removed in vacuo. Purification by flash chromatography eluting with $CH_2Cl_2$/MeOH, 98:2 affords the title compound. $^1$H NMR (DMSO-6) δ 10.0 (1H, s) 9.4 (1H, d), 8.9 (1H, t), 8.77-8.73 (1H, m), 8.4 (1H, dt), 8.1 (1H, s), 7.61-7.59 (1H, m), 7.54 (2H, t), 3.8-3.72 (2H, m), 3.62-3.56 (2H, m) 3.31 (3H, s) 2.02 (3H, s); MS m/z 376 [M+H]$^+$

Examples 54-57

These compounds, namely

N-{3-[5-Isopropylamino-6-(pyridine-3-carbonyl)-pyrazin-2-yl]phenyl}acetamide (Ex. 54), $^1$H NMR (400 MHz, DMSO-d6) δ 9.80 (1H, s), 9.06 (1H, d), 8.93 (1H, s), 8.77-8.74 (2H, m), 8.40 (1H, dt), 8.10 (1H, s), 7.59 (1H, dd), 7.54 (2H, m), 7.34 (1H, t), 4.42 (1H, m), 2.04 (3H, s), 1.31 (6H, d). MS m/z 376 [M+H]$^+$ N-Cyclopropyl-3-[5-morpholin-4-yl-6-(pyridine-3-carbonyl)-pyrazin-2-yl]benzenesulfonamide (Ex. 55), $^1$H NMR (DMSO-6) δ 9.18 (1H, d) 8.97 (1H, s), 8.84 (1H, dd), 8.41 (1H, dt), 8.24 (1H, t), 8.17 (1H, dt), 7.88 (1H, d), 7.77-7.74 (1H, m), 7.67 (1H, t), 7.61 (1H, dd) 3.62 (4H, t) 3.46 (4H, t) 2.08 (1H, m) 0.39-0.30 (4H, m); MS m/z 488 [M+Na]$^+$ N-Cyclopropyl-3-[5-(2-methoxy-ethylamino)-6-(pyridine-2-carbonyl)-pyrazin-2-yl]benzenesulfonamide (Ex. 56), $^1$H NMR (400 MHz, DMSO-d6) δ 9.16 (1H, s), 8.77 (1H, t), 8.68 (1H, t), 8.20 (1H, t), 8.11 (1H, d), 7.96 (1H, m), 7.86 (1H, d), 7.81 (1H, d), 7.73 (1H, d), 7.63 (1H, t), 7.58 (1H, ddd), 7.50 (1H, m), 3.77 (2H, q), 3.58 (2H, t), 3.32 (3H, s), 2.04 (1H, m), 0.40-0.29 (4H, m). MS m/z 476 [M+Na]$^+$ N-{3-[5-Amino-6-(-trifluoromethylpyridine-3-carbonyl)pyrazin-2-yl]phenyl}acetamide (Ex. 57), $^1$H NMR (DMSO-6) δ 9.97 (1H, s) 9.16 (1H, d), 8.90 (1H, s), 8.66 (1H, d), 8.21 (1H, s), 8.11-8.08 (2H, m), 7.54 (1H, d), 7.47 (1H, d), 7.35 (1H, t), 2.03 (3H, s); MS m/z 424 [M+Na]$^+$ are prepared in an analogous manner to Ex. 53, substituting 3-acetamidobenzene boronic acid (25.5 mg, 0.14 mmol) and [6-bromo-3-(2-methoxy-ethylamino)pyrazin-2-yl]pyridin-2yl-methanone (Intermediate AC) with the appropriate boronic acid and pyrazine bromide. The pyrazine bromides are prepared as described in section 'Preparation of Intermediate Compounds'.

Example 58

3-[5-Amino-6-(pyridine-3-carbonyl)-pyrazin-2-yl]-N-(2-methoxy-ethyl)-benzenesulfonamide A suspension of (3-Amino-6-bromo-pyrazin-2-yl)-pyridin-3-yl-methanone (Intermediate AA) (0.05 g, 0.18 mmol), bis(pinacolato)diboron (0.05 g, 0.19 mmol), Pd(dppf)Cl$_2$.DCM (0.015 g, 0.018 mmol) and potassium acetate (0.03 g, 0.27 mmol) in DME (4 ml) is heated at reflux for 4 hours. Pd(dppf)Cl$_2$.DCM (7 mg, 0.009 mmol), 3-Bromo-N-(2-methoxy-ethyl)-benzenesulfonamide (Intermediate DD) (0.05 g, 0.18 mmol), 2M Na$_2$CO$_3$ (1 ml) and DME (3 ml) are added to the suspension, which is heated at reflux for a further 1 hour. After cooling, the reaction mixture is diluted with EtOAc, washed with water, dried (MgSO$_4$) and filtered through a short pad of Celite® (filter material). The solvent is removed in vacuo, and the residue purified by flash column chromatography (SiO$_2$, iso-hexane/EtOAc) to afford the title compound as a yellow solid. $^1$H NMR (400 MHz, DMSO-d6) δ 9.16 (2H, m), 8.86 (1H, dd), 8.43 (1H, dt), 8.37 (1H, m), 8.23 (3H, m), 7.85 (1H, m), 7.77 (1H, m), 7.66 (1H, ddd), 3.38 (2H, t), 3.22 (3H, s), 3.01 (2H, m). MS m/z 414.01 [M+H]$^+$

Examples 59-81

These compounds namely,

5-[5-Amino-6-(pyridine-3-carbonyl)-pyrazin-2-yl]-2-chloro-N-(4-hydroxy-cyclohexyl)-benzene sulfonamide (Ex. 59), $^1$H NMR (400 MHz, DMSO-d6) δ 9.07 (1H, s), 9.05 (1H, d), 8.80 (1H, dd), 8.49 (1H, d), 8.38 (1H, dt), 8.15-8.13 (3H, m), 7.84 (1H, d), 7.74 (1H, d), 7.57 (1H, dd), 4.45 (1H, bs), 3.27-3.22 (1H, m), 3.00-2.93 (1H, m), 1.69 (2H, d), 1.59 (2H, d), 1.28-1.20 (2H, m), 1.07-0.99 (2H, m); MS m/z 488 [M+H]$^+$ {3-Amino-6-[3-(morpholine-4-sulfonyl)-4-trifluoromethyl-phenyl]-pyrazin-2-yl}-pyridin-3-yl-methanone (Ex. 60), $^1$H NMR (400 MHz, DMSO-d6) δ 9.19 (1H, s), 9.07 (1H, dd), 8.79 (1H, dd), 8.46 (1H, m), 8.39 (1H, d), 8.31 (1H, dt), 8.26 (2H, s), 8.12 (1H, d), 7.59 (1H, ddd), 3.59 (4H, t), 3.03 (4H, t); MS m/z 494 [M+H]$^+$ 5-[5-Amino-6-(pyridine-3-carbonyl)-pyrazin-2-yl-N-cyclopropyl-2,4-difluoro-benzenesulfonamide (Ex. 61), $^1$H NMR (400 MHz, DMSO-d6) δ 9.02 (1H, d), 8.78 (1H, d), 8.75 (1H, dd), 8.34 (1H, dt), 8.28 (1H, d), 8.20 (1H, m), 8.18 (2H, s), 7.73 (1H, t), 7.53 (1H, dd), 2.19 (1H, m), 0.43 (2H, m), 0.38 (2H, m). MS m/z 432 [M+H]$^+$ 1-{6-[5-Amino-6-(pyridine-3-carbonyl)-pyrazin-2-yl]-2,3-dihydro-indol-1-yl}-ethanone (Ex. 62), $^1$H NMR (400 MHz, DMSO-d6) δ 9.14 (1H, s), 8.95 (1H, s), 8.87 (1H, dd), 8.69 (1H, s), 8.57 (1H, d), 8.12 (2H, s), 7.71 (1H, t), 7.63 (1H, d), 7.39 (1H, d), 7.20 (N14-H, t), 4.21 (2H, t), 3.24 (2H, t), 2.26 (3H, s); MS m/z 360 [M+H]$^+$ 6-[5-Amino-6-(pyridine-3-carbonyl)-pyrazin-2-yl]-1,3-dihydro-indol-2-one (Ex. 63), $^1$H NMR (400 MHz, DMSO-d6) δ 10.51 (H, s), 9.08 (1H, s), 8.96 (1H, s), 8.81 (1H, d), 8.35 (1H, dt), 8.02 (2H, s), 7.63 (1H, dd), 7.53 (1H, dd), 7.28 (2H, d), 3.50 (2H, s); MS m/z 332 [M+H]$^+$ {3-Amino-6-[3-(4-methyl-piperazine-1-sulfonyl)-5-trifluoromethyl-phenyl]-pyrazin-2-yl}-pyridin-3-yl-methanone (Ex. 64), $^1$H NMR (400 MHz, DMSO-d6) δ 9.29 (1H, s), 9.09 (1H, dd), 8.80 (1H, dd), 8.65 (1H, s), 8.41 (1H, s), 8.32 (1H, dt), 8.26 (2H, s), 7.90 (1H, s), 7.57 (1H, ddd), 2.93 (4H, bs), 2.37 (4H, bs), 2.15 (3H, bs); MS m/z 507 [M+H]$^+$ 6-[5-Amino-6-(pyridine-3-carbonyl)-pyrazin-2-yl]-4H-benzo[1,4]oxazin-3-one (Ex. 65), $^1$H NMR (400 MHz, DMSO-d6) δ 10.87 (1H, s), 9.06 (1H, s), 8.86 (1H, s), 8.78 (1H, dd), 8.33 (1H, dt), 7.99 (2H, s), 7.62 (1H, dd), 7.51 (1H, dd), 7.36 (1H, d), 7.04 (1H, d), 4.60 (2H, s); MS m/z 348 [M+H]$^+$

[3-Amino-6-(1H-indol-4-yl)-pyrazin-2-yl]-pyridin-3-yl-methanone (Ex. 66), $^1$H NMR (400 MHz, DMSO-d6) δ 11.24 (1H, s), 9.15 (1H, br s), 8.97 (1H, s), 8.80 (1H, br s), 8.37 (1H, d), 8.01 (2H, s), 7.60 (1H, br s), 7.48 (2H, dd), 7.29 (1H, t), 7.17 (1H, t), 7.11 (N14-H, t), 6.56 (1H, s); MS m/z 316 [M+H]$^+$ 3-[5-Amino-6-(pyridine-3-carbonyl)-pyrazin-2-yl]-5-trifluoromethyl-benzenesulfonamide (Ex. 67), $^1$H NMR (400

MHz, DMSO-d6) δ 9.20 (1H, s), 9.06 (1H, d), 8.81 (1H, dd), 8.62 (1H, s), 8.47 (1H, s), 8.37 (1H, dt), 8.23 (2H, s), 8.10 (1H, s), 7.59 (2H, s), 7.58 (1H, ddd); MS m/z 424 [M+H]$^+$ {3-Amino-6-[3-(4-methyl-piperazine-1-sulfonyl)-4-trifluoromethyl-phenyl]-pyrazin-2-yl}-pyridin-3-yl-methanone (Ex. 68), $^1$H NMR (400 MHz, DMSO-d6) δ 9.20 (1H, s), 9.11 (1H, d), 8.81 (1H, dd), 8.46 (2H, m), 8.33 (1H, dt), 8.30 (2H, s), 8.16 (1H, d), 7.61 (1H, ddd), 3.78 (2H, bs), 3.17 (6H, bs), 2.79 (3H, bs); MS m/z 507[M+H]$^+$ {3-Amino-6-[5-morpholine-4-sulfonyl)-pyridin-3-yl]-pyrazin-2-yl}-pyridin-3-yl-methanone (Ex. 69), $^1$H NMR (400 MHz, DMSO-d6) δ 9.47 (1H, d), 9.23 (1H, s), 9.13 (1H, d), 8.86 (2H, d), 8.86 (1H, dd), 8.42 (1H, t), 8.37 (1H, dt), 8.26 (2H, bs), 7.64 (1H, dd), 3.66 (2H, t), 2.95 (2H, t); MS m/z 427[M+H]$^+$ {3-Amino-6-[2,4-difluoro-5-(4-methyl-piperazine-1-sulfonyl)-phenyl]-pyrazin-2-yl}-pyridin-3-yl-methanone (Ex. 70), $^1$H NMR (400 MHz, DMSO-d6) δ 9.09 (1H, dd), 8.81 (1H, d), 8.78 (1H, dd,) 8.33 (1H, dt), 8.23 (2H, s), 8.15 (1H, t), 7.87 (1H, t), 7.58 (1H, ddd), 3.78 (1H, bs), 3.47 (2H, bs), 3.21 (2H, bs), 2.83 (4H, bs); MS m/z 475 [M+H]$^+$ {3-Amino-6-[–4-chloro-3-(4-methyl-piperazine-1-sulfonyl)-phenyl]-pyrazin-3-yl-methanone (Ex. 71), $^1$H NMR (400 MHz, CDCl$_3$-d1) δ 9.27 (1H, dd), 8.82 (2H, m), 8.54 (1H, d), 8.40 (1H, dt), 7.99 (1H, dd), 7.62 (1H, d), 7.54-7.49 (1H, m), 3.35 (4H, br s), 2.48 (4H, br s), 2.31 (3H, s); MS m/z 473 [M+H]$^+$ {3-Amino-6-[3-(4-cyclopropyl-piperazine-1-sulfonlyl)-phenyl]-pyrazin-2-yl}-pyridin-3-yl-methanone (Ex. 72), $^1$H NMR (400 MHz, DMSO-d6) δ 9.11 (1H, s), 9.09 (1H, d), 8.79 (1H, dd), 8.31 (2H, m), 8.16 (2H, s), 8.12 (1H, s), 7.73 (1H, t), 7.69 (1H, m), 7.56 (1H, dd), 2.81 (4H, br), 2.58 (4H, m), 1.63 (1H, m), (0.38 2H, m), 0.19 (2H, m). MS m/z 465 [M+H]$^+$ {3-Amino-6-[3-(4-methyl-[1,4]diazepane-1-sulfonyl)-phenyl]-pyrazin-2-yl}pyridine-3-yl-methanone (Ex. 73), $^1$H NMR (400 MHz, DMSO-d6) δ 9.11 (1H, s), 9.09 (1H, d), (8.78 (1H, dd), (8.31, dt), 8.25 (1H, m), 8.19 (1H, m), 8.15 (2H, s), 7.76 (1H, m), 7.69 (1H, t), 7.56 (1H, ddd), 3.35 (2H, m), 3.25 (2H, t), 2.57 (2H, m), 2.27 (3H, s), 1.74 (2H, m). MS m/z 453 [M+H]$^+$ {3-Amino-6-[2,4-difluoro-5-(morpholine-4-sulfonyl)-phenyl]-pyrazin-2-yl}-pyridin-3-yl-methanone (Ex. 74), $^1$H NMR (400 MHz, DMSO-d6) δ 9.07 (1H, dd), 8.80 (1H, d), 8.76 (1H, dd), 8.31 (1H, dt), 8.20 (2H, s), 8.10 (1H, t), 7.79 (1H, t), 7.55 (1H, dd), 3.65 (4H, t), 2.98 (4H, t); MS m/z 462 [M+H]$^+$ (3-Amino-6-{3-[4-(2-hydroxy-ethyl)-piperazine-1-sulfonyl]-phenyl}-pyrazin-2-yl)-pyridin-3-yl-methanone (Ex. 75), $^1$H NMR (400 MHz, DMSO-d6) δ 9.20 (1H, s), 9.07 (1H, d), 8.86 (1H, dd), 8.38 (2H, m), 8.23 (3H, m), 7.89 (1H, d), 7.82 (1H, t), 7.78 (1H, m), 7.65 (1H, dd), 4.42 (1H, s), 3.49 (2H, m), 2.93 (4H, br), 2.57 (4H, br), 2.43 (2H, br). MS m/z 469 [M+H]$^+$ 3-[5-Amino-6-(pyridine-3-carbonyl)-pyrazin-2-yl]-N-[2-(4-methyl-piperazin-1-yl)-ethyl]-benzenesulfonamide (Ex. 76), $^1$H NMR (400 MHz, DMSO-d6) δ 9.07 (2H, s), 8.78 (1H, dd), 8.35 (1H, m), 8.30 (1H, s), 8.15 (3H, m), 7.78 (1H, d), 7.67 (1H, t), 7.58 (1H, dd), 7.48 (1H, m), 2.86 (2H, m), 2.27 (10H, m), 2.06 (s, 3H). MS m/z 482 [M+H]$^+$ 3-[5-Amino-6-(pyridine-3-carbonyl)-pyrazin-2-yl]-N-cyclobutyl-benzenesuflonamide (Ex. 77), $^1$H NMR (400 MHz, DMSO-d6) δ 9.14 (1H, d), 9.12 (1H, s), 8.87 (1H, dd), 8.41 (1H, m), 8.33 (1H, m), 8.22 (1H, m), 8.19 (1H, s), 7.98 (2H, d), 7.81 (1H, m), 7.70 (1H, t), 7.65 (1H, ddd), 3.70 (1H, m), 1.90 (2H, m), 1.73 (2H, m). MS m/z 410. [M+H]$^+$ {3-Amino-6-[3-(4-methyl-piperazine-1-sulfonyl)-phenyl]-pyrazin-2-yl}-pyridin-3-yl-methanone (Ex. 78), $^1$H NMR (400 MHz, DMSO-d6) δ 9.18 (1H, s), 9.15 (1H, dd), 8.84 (1H, dd), 8.37 (2H, m), 8.21 (3H, m), 7.79 (1H, dd), 7.76 (1H, dt), 7.62 (1H, ddd), 2.93 (4H, m), 2.41 (4H, m), 2.19 (3H, s). MS m/z 439 [M+H]$^+$ 5-[5-Amino-6-(pyridine-3-carbonyl)-pyrazin-2-yl]-2-chloro-N-cyclopropyl-benzenesuflonamide (Ex. 79), $^1$H NMR (400 MHz, DMSO-d6) δ 9.07 (1H, s), 9.04 (1H, d), 8.79 (1H, dd), 8.50 (1H, d), 8.37 (1H, dt), 8.22 (1H, d), 8.19-8.16 (3H, m), 7.76 (1H, d), 7.58 (1H, dd), 2.20-2.15 (1H, m), 0.45-0.38 (4H, m); MS m/z 430[M+H]$^+$ {3-Amino-6-[4-chloro-3-(morpholine-4-sulfonyl)-phenyl]-pyrazin-2-yl}-pyridin-3-yl-methanone (Ex. 80), $^1$H NMR (400 MHz, DMSO-d6) δ 9.11 (1H, s), 9.06 (1H, d), 8.78 (1H, dd), 8.38 (1H, d), 8.34 (1H, dt), 8.25 (1H, dd), 8.18 (2H, s), 7.82 (1H, d), 7.57 (1H, ddd), 3.61 (4H, t), 3.13 (4H, t); MS m/z 460 [M+H]$^+$ 3-[5-Amino-6-(pyridine-3-carbonyl)-pyrazin-2-yl]-N-cyclopropylmethyl-benzenesulfonamide (Ex. 81), $^1$H NMR (400 MHz, DMSO-d6) δ 9.01 (2H, m), 8.73 (1H, m), 8.29 (1H, dt), 8.22 (1H, m), 8.09 (3H, m), 7.71 (1H, dt), 7.62 (1H, m), 7.51 (1H, ddd), 2.60 (2H, t), 0.72 (1H, m), 0.26 (2H, m), 0.01 (2H, m). MS m/z 410 [M+H]$^+$ are prepared by an analogous procedure to Example 58 by replacing 3-Bromo-N-(2-methoxy-ethyl)-benzenesulfonamide (Intermediate DD) with the appropriate halo compound. These are either commercially available or synthesised as described in section 'Preparation of Intermediate Compounds'.

Examples 82-85

These compounds, namely

{3-Amino-6-[3-(4-methyl-piperazine-1-sulfonyl)-phenyl]-pyrazin-2-yl}-(4-chloro-phenyl)-methanone (Ex. 82), $^1$H NMR (400 MHz, DMSO-d6) δ 9.09 (1H, s) 8.31 (1H, dt) 8.15-8.14 (1H, m) 8.07 (2H, s) 7.98-7.95 (2H, m,) 7.76-7.68 (2H, m) 7.60-7.57 (2H, m) 2.85 (4H, bs) 2.35 (4H, t) 2.13 (3H, s); MS m/z 472, 474 [M+H]$^+$ {3-amino-6-[4-chloro-3-(4-methyl-piperazine-1-sulfonyl)-phenyl]-pyrazin-2-yl}-(4-chloro-phenyl)-methanone (Ex. 83), $^1$H NMR (400 MHz, DMSO-d6) δ 9.09 (1H, s), 8.50 (1H, d), 8.28 (1H, dd), 8.12 (2H, s), 8.02 (2H, d), 7.85 (1H, d), 7.61 (2H, d), 3.86 (2H, bs), 3.47 (2H, bs), 3.08 (4H, bs), 2.83 (3H, s); MS m/z 506 [M+H]$^+$ {3-Amino-6-[4-chloro-3-(4-isopropyl-pierazine-1-sulfonyl)-phenyl]-pyrazin-2-yl}-(4-chloro-phenyl)-methanone (Ex. 84), $^1$H NMR (400 MHz, DMSO-d6) δ 9.07 (1H, s), 8.39 (1H, d), 8.24 (1H, dd), 8.10 (2H, s), 7.99 (2H, d), 7.80 (1H, d), 7.59 (2H, d), 3.10 (4H, bs), 2.69-2.64 (1H, m), 2.45 (4H, t), 0.93 (6H, d); MS m/z 534 [M+H]$^+$ 3-[5-Amino-6-(4-fluoro-benzoyl)-pyrazin-2-yl]-N-(2-methoxy-ethyl)-benzenesulfonamide (Ex. 85), $^1$H NMR (400 MHz, DMSO-d6) δ 9.04 (1H, s), 8.33 (1H, t), 8.20 (1H, dt), 8.11-806 (2H, m), 8.02 (2H, s), 7.78 (1H, dt), 7.73 (1H, bs), 7.68 (2H, t), 7.39-7.33 (2H, m), 3.30 (2H, t), 3.15 (3H, s), 2.92 (2H, t); MS m/z 431 [M+H]$^+$ are prepared in an analogous manner to Example 58 using the appropriate aryl bromide and pyrazine bromide intermediates, which are prepared as described in section 'Preparation of Intermediate Compounds'. The compounds are recovered from the reaction mixture and purified using conventional techniques.

Example 86

[3-Amino-6-(3,4-dichloro-phenyl)-pyrazin-2-yl]-(4-piperidin-1-ylmethyl-phenyl)-methanone A solution of 0.25 M [4-(1-piperidinyl-methyl)phenyl] magnesium bromide in THF (5.51 ml, 1.37 mmol) is added dropwise to a solution of 3-amino-6-(3,4-dichloro-phenyl)-pyrazine-2-carboxylic acid methoxy-methyl amide (Intermediate B) (0.09 g, 0.27 mmol) in THF (5 ml) and the resulting solution is stirred for 2 hours. The solution is cooled to 0° C., and 2M HCl (10 ml) is added. The solution is washed with EtOAc (20 ml) and then the pH is adjusted to 11 using 2M NaOH. Extraction with EtOAc (50 ml), drying (MgSO$_4$) and removal of solvent in vacuo affords a yellow oil. Purification by flash chromatography (SiO$_2$, 50-100% EtOAc in iso-hexane) followed by trituration with methanol affords the title compound as a yellow solid. $^1$H NMR (400 MHz, DMSO-d6) δ 9.04 (1H, s), 8.12 (1H, d), 7.97 (2H, bs), 7.93-7.88 (3H, m), 7.71 (1H, d), 7.47 (2H, d), 3.54 (2H, s), 2.36 (4H, bs), 1.52-1.51 (4H, m), 1.43-1.37 (2H, m); MS m/z 441, 443 [M+H]$^+$

Example 87

{3-Amino-6-[2-methyl-5-(morpholine-4-sulfonyl)-phenyl]-pyrazin-2-yl}-cyclopropyl-methanone A 1M solution of cyclopropyl magnesium bromide in THF (0.21 ml, 0.21 mmol) is added to a solution of 3-amino-6-[2-methyl-5-(morpholine-4-sulfonyl)-phenyl]-pyrazine-2-carboxylic acid methoxy-methyl amide (Intermediate C) (0.058 mg, 0.14 mmol) in anhydrous THF (3 ml) under N$_2$. The orange solution is stirred at room temperature for 2 hours after which time a 1M solution of cyclopropyl magnesium bromide in THF (0.21 ml, 0.21 mmol) is added. The orange solution is stirred at room temperature for 1 hour. 1M HCl (15 ml) is added, and the product extracted into EtOAc (30 ml), dried (MgSO$_4$), and concentrated in vacuo. Purification by flash chromatography (SiO$_2$, 33-50% EtOAc in iso-hexane) yields the title compound as a yellow solid. $^1$H NMR (400 MHz, DMSO-d6) δ 8.63 (1H, s), 7.92 (2H, bs), 7.79 (1H, s), 7.70-7.63 (2H, m), 3.64-3.62 (4H, m), 3.49-3.43 (1H, m), 2.90 (4H, bs) 2.54 (3H, s), 1.09-1.01 (4H, m); MS m/z 403 [M+H]$^+$

Example 88

3-[6-Amino-5-(4-tert-butyl-benzoyl)-pyridin-3-yl]-N-cyclopropyl-benzenesulfonamide A solution of 2-amino-5-(3-cyclopropylsulfamoyl-phenyl)-N-methoxy-N-methyl-nicotinamide (Intermediate GA) (0.08 g, 0.21 mmol) in THF (3 ml) is cooled to 0° C. 2M 4-tert Butyl phenyl magnesium bromide in THF (0.32 ml, 0.64 mmol) is added dropwise, and the resulting solution is stirred and allowed to warm to room temperature overnight. The reaction is quenched with 2M HCl (5 ml). The solvent is removed in vacuo and the residue purified by reverse phase column chromatography (Isolute™ C18, 0-100% MeCN in water –0.1% TFA). The solid obtained is dissolved in DCM, washed with 2M NaOH. The solvent is removed in vacuo and the resulting solid is dried in vacuo at 40° C. overnight to yield the title compound. $^1$H NMR (400 MHz, DMSO-d6) δ 8.69 (1H, d), 8.01 (1H, d), 7.97-7.89 (3H, m), 7.78 (1H, d), 7.72-7.67 (5H, m), 7.64 (2H, d), 2.18-2.13 (1H, m), 1.38 (9H, s), 0.47-0.38 (4H, m); MS m/z 450 [M+H]$^+$

Example 89

3-(6-Amino-5-benzoyl-pyridin-3-yl)-N-cyclopropyl-benzenesulfonamide

This compound prepared in an analogous manner to Example 88 using either Intermediate GA as prepared in section 'Preparation of Intermediate Compounds' and grignard reagent. The compound is recovered from the reaction mixture and purified using conventional techniques. $^1$H NMR (400 MHz, DMSO-d6) δ8.65 (1H, d), 7.94 (1H, d), 7.90 (1H, d), 7.88-7.86 (1H, m), 7.78 (2H, br s), 7.73-7.69 (3H, m), 7.64 (2H, t), 7.55 (2H, t), 7.13 (N14-H, t), 2.12-2.04 (1H, m), 0.44-0.33 (4H, m); MS m/z 394 [M+H]$^+$

Example 90

[2-Amino-5-(3-chloro5-methyl-phenyl)-pyridin-3-yl]-phenyl-methanone

A solution of 1M phenyl magnesium bromide in THF (0.79 ml, 0.79 mmol) is added dropwise to a solution of 2-amino-5-(3-chloro-5-methyl-phenyl)-N-methoxy-N-methyl-nicotinamide (intermediate GB) (0.08 g, 0.26 mmol) in THF (3 ml) at 0° C. The resulting solution is stirred at 0° C. for 30 minutes. 1M Phenyl magnesium bromide in THF (0.79 ml, 0.79 mmols) is added dropwise and the solution stirred for a further 30 minutes at 0° C. 2.5M HCl (10 ml) is added and the product extracted with EtOAc, and solvent removed in vacuo. Purification by reverse phase column chromatography (Isolute™ C18, 0-100% MeCN in water –0.1% TFA) yields the title compound. $^1$H NMR (400 MHz, DMSO-d6) δ 8.28 (1H, dd), 7.77 (2H, br s), 7.66-7.59 (4H, m), 7.55-7.51 (2H, m), 7.37 (1H, d), 7.29 (1H, dd), 7.23 (1H, d), 2.23 (3H, s); MS m/z 323 [M+H]$^+$

Example 91

{2-Amino-5-[2-methyl-5-(morpholine-4-sulfonyl)-phenyl]-pyridin-3-yl}-pyridin-3-yl-methanone A suspension of (2-amino-5-bromo-pyridin-3-yl)-pyridin-3-yl-methanone (intermediate H) (0.05 g, 0.18 mmol), 3-N-morpholinylsulfonylphenyl boronic acid (0.055 g, 0.19 mmol), Pd(dppf)Cl$_2$.DCM (0.015 g, 0.018 mmol) in 2M Na$_2$CO$_3$ (1 ml) and DME (3 ml) is heated at reflux for 1 hour. The reaction mixture is cooled to room temperature, absorbed onto silica and purified by flash chromatography (SiO$_2$, 20-80% EtOAc in iso-hexane). The product obtained is triturated with ethanol, and dried in vacuo at 45° C. overnight to yield the title compound. $^1$H NMR (400 MHz, DMSO-d6) δ 8.83 (1H, d), 8.76 (1H, d), 8.39 (1H, d), 8.08 (1H, dt), 7.84 (2H, s), 7.67 (1H, d), 7.60-7.53 (3H, m), 7.50 (1H, d), 3.60 (4H, t), 2.83 (4H, t), 2.35 (3H, s); MS m/z 439 [M+H]$^+$

Example 92

{2-Amino-5-[3-(4-methyl-piperazine-1-sulfonyl)-phenyl]-pyridin-3-yl}-pyridin-2-yl-methanone A suspension of (2-amino-5-bromo-pyridin-3-yl)-pyridin-3-yl-methanone (Intermediate H) (0.05 g, 0.18 mmol), bis(pinacolato)diboron (0.05 g, 0.19 mmol), Pd(dppf)Cl$_2$.DCM (0.015 g, 0.018 mmol) and potassium acetate (0.026 g, 0.27 mmol) in DME (4 ml) is heated at reflux for 3 hours. Pd(dppf)Cl$_2$.DCM (0.015 g, 0.02 mmol), 1-(3-bromo-benzensulfonyl)-4-methyl-piperazine (Intermediate DA) (0.05 g, 0.18 mmol), 2M Na$_2$CO$_3$ (1 ml) and DME (1 ml) are added and the reaction heated at reflux overnight. The reaction mixture is purified directly by reverse phase column chromatography (Isolute™ C18, 0-100% MeCN in water –0.1% TFA) to yield an oil which is triturated with iso-hexane and dried in vacuo at 45° C. overnight to yield the title compound. $^1$H NMR (400 MHz, DMSO-d6) δ 8.93 (1H, d), 8.87 (1H, dd), 8.78 (1H, d), 8.18 (1H, dt), 8.02-7.99 (2H, m), 7.92 (3H, s), 7.81-7.76 (1H, m), 7.66 (1H, dd), 3.96-2.18 (7H, br hump); MS m/z 438 [M+H]$^+$ Examples 93-96

These compounds, namely

5-[5-Amino-6-(pyridine-3-carbonyl)-pyrazin-2-yl]-N-cyclopropylmethyl-2,4-difluoro-benzenesulfonamide (Ex. 93), $^1$H NMR (400 MHz, DMSO-d6) δ 8.98 (1H, dd), 8.73 (1H, d), 8.12 (2H, t), 8.06 (1H, t), 7.65 (1H, t), 7.49 (3H, ddd), 2.68 (2H, t), 0.73-0.68 (1H, m), 0.28-0.23 (2H, m), 0.02-0.01 (2H, m). MS m/z 446 [M+H]$^+$ 5-[5-Amino-6-(pyridine-3-carbonyl)-pyrazin-2-yl]-2,4-difluoro-N-(2-methoxy-ethyl)-benzenesulfonamide (Ex. 94), $^1$H NMR (400 MHz, DMSO-d6) δ 9.04 (1H, d), 8.78-8.76 (1H, dt), 8.38 (2H, t), 8.18-8.14 (3H, m), 8.07 (1H, t), 7.69 (1H, t), 7.57 (1H, ddd), 3.27 (2H, t), 3.09 (3H, s), 3.02 (2H, q). MS m/z 450 [M+H]$^+$ 5-[5-Amino-6-(pyridine-3-carbonyl)-pyrazin-2-yl]-N-(2-methoxy-ethyl)-2-trifluoromethyl-benzenesulfonamide (EX. 95), $^1$H NMR (400 MHz, DMSO-d6) δ 9.19 (1H, s), 9.13 (1H, dd), 8.85 (1H, dd), 8.63 (1H, s), 8.41 (1H, dt), 8.34-8.31 (3H, m), 8.11-8.05 (2H, m), 7.65 (1H, ddd), 3.35 (2H, t), 3.17 (3H, s), 3.09 (2H, q). MS m/z 482 [M+H]$^+$ 5-[5-Amino-6-(pyridine-3-carbonyl)-pyrazin-2-yl]-2,4-difluoro-N-(4-hydroxy-cyclohexyl)-benzenesulfonamide (Ex. 96), $^1$H NMR (400 MHz, DMSO-d6) δ 9.05 (1H, dd), 8.79-8.77 (2H, m), 8.40 (1H, dt), 8.20-8.16 (3H, m), 7.99 (1H, d), 7.69 (1H, t), 7.58 (1H, ddd), 3.29-3.22 (1H, m), 3.01-2.92 (1H, m), 1.70-1.68 (2H, m), 1.59-1.56 (2H, m), 1.09-1.03 (2H, m). MS m/z 490 [M+H]$^+$ are prepared by an analogous procedure to Example 58 by replacing 3-Bromo-N-(2-methoxy-ethyl)-benzenesulfonamide (Intermediate DD) with the appropriate halide. The halides are either commercially available or synthesised as described in section 'Preparation of Intermediate Compounds'.

Example 97

{3-Amino-6-[2-methyl-5-(morpholine-4-sulfonyl)-phenyl]-pyrazin-2-yl}-pyridin-3-yl-methanone O-methyl-oxime {3-Amino-6-[2-methyl-5-(morpholine-4-sulfonyl)-phenyl]-pyrazin-2-yl}-pyridin-3-yl-methanone (Ex. 2) (0.05 g, 0.11 mmol), O-methylhydroxylamine hydrochloride (0.095 g, 1.14 mmol), ethanol (4 ml), water (1 ml) and triethylamine (0.07 g, 0.68 mmol) are heated at 120° C. in a microwave for 3.5 hours. The reaction mixture is purified by reverse phase column chromatography (C18, 0-100% MeCN in water –0.1% TFA) to yield the title compound. $^1$H NMR (400 MHz, DMSO-d6) δ 8.56 (1H, dd), 8.48 (1H, d), 8.35 (1H, s), 7.75 (1H, dt), 7.70 (2H, bs), 7.55-7.53 (2H, m), 7.48-7.43 (2H, m), 4.01 (3H, s), 3.61 (4H, t), 2.76 (4H, t) 2.19 (3H, s); MS m/z 469 [M+H]$^+$ Example 98

5-(5-Amino-6-cyclopropanecarbonyl-pyrazin-2-yl)-2,4-difluoro-N-(4-hydroxy-cyclohexyl)-benzenesulfonamide A 1M solution of cyclopropyl magnesium bromide in THF (0.65 ml, 0.65 mmol) is added to a solution of 2-amino-5-[2,4-difluoro-5-(4-hydroxy-cyclohexylsulfamoyl)-phenyl]-N-methoxy-N-methyl-nicotinamide (Intermediate CA) (0.154 mg, 0.33 mmol) in anhydrous THF (5 ml) under N$_2$. The orange solution is stirred at room temperature for 2 hours after which time a 1M solution of cyclopropyl magnesium bromide in THF (0.65 ml, 0.65 mmol) is added. The orange solution is stirred at room temperature for 1 hour. Saturated brine (10 ml) is added and the product extracted with EtOAc (2×100 ml). The combined organic extracts are dried (MgSO$_4$) and concentrated in vacuo. Purification by flash chromatography (SiO$_2$, 40-60% EtOAc in iso-hexane) yields the title compound as a yellow solid. $^1$H NMR (400 MHz, DMSO-d6) δ 8.61 (1H, d), 8.21 (1H, t), 7.98 (1H, d), 7.88 (2H, br), 7.57 (1H, t), 3.39 (1H, m), 3.23 (1H, m) 3.13 (1H, m), 2.92 (1H, m), 1.55 (4H, m), 1.31 (1H, m), 1.10 (2H, m), 0.94 (6H, m); MS m/z 453 [M+H]$^+$ Example 99

3-(5-Amino-6-cyclopropanecarbonyl-pyrazin-2-yl)-N-(2-methoxy-ethyl)-benzenesulfonamide A 1M solution of cyclopropyl magnesium bromide in THF (1.3 ml, 1.3 mmol) is added to a solution of 3-amino-6-[3-(2-methoxy-ethylsulfamoyl)-phenyl]-pyrazine-2-carboxylic acid methoxy-methyl-amide (Intermediate CB) (0.49 g, 1.24 mmol) in anhydrous THF (15 ml) under N$_2$. The orange solution is stirred at room temperature for 18 hours after which time a 1M solution of cyclopropyl magnesium bromide in THF (1.3 ml, 1.3 mmol) is added. The orange solution is stirred at room temperature for 1 hour. 1M HCl (45 ml) is added and the product extracted into EtOAc (120 ml), dried (MgSO$_4$), and concentrated in vacuo. Purification by flash chromatography (SiO$_2$, 50-100% EtOAc in iso-hexane) yields the title compound as a yellow solid. $^1$H NMR (400 MHz, DMSO-d6) δ 9.08 (1H, s), 8.51 (1H, m), 8.39 (1H, d), 8.22-7.90 (2H, br), 7.88 (2H, m), 7.76 (1H, t), 3.73 (1H, m) 3.37 (2H, t), 3.21 (3H, s), 3.02 (2H, q), 1.19 (2H, m), 1.14 (2H, m); MS m/z 377 [M+H]$^+$ Example 100

{3-Amino-6-[2-methyl-5-(morpholine-4-sulfonyl)-phenyl]-pyrazin-2-yl}-pyridin-3-yl-methanone O-(2-dimethylamino-ethyl)-oxime This compound is prepared by an analogous procedure to Example 97 by replacing O-methylhydroxylamine hydrochloride with 2-(aminooxy)-N,N-dimethyl-ethanamine dihydrochloride.
$^1$H NMR (400 MHz, CDCl$_3$-d1) δ 9.01 (1H, s), 8.71 (1H, d), 8.24 (1H, s), 8.22 (1H, dt), 7.85 (1H, d), 7.59 (1H, s), 7.58 (1H, dd), 7.37 (1H, d), 4.74 (2H, t), 3.73 (4H, t), 3.51 (2H, t), 2.95 (4H, t), 2.84 (6H, s), 2.21 (3H, s); MS m/z 526 [M+H]$^+$ Example 101

3-[5-Amino-6-(pyridin-3-yloxy)-pyrazin-2-yl]-N-cyclopropyl-benzenesulfonamide

This compound is prepared by an analogous procedure to Example 1 by replacing 5-(4,4,5,5-Tetramethyl-[1,3,2]-dioxaborolan-2-yl)-3-trifluoromethyl-pyridin-2-ylamine (Intermediate K) with the appropriate boronic acid and (3-amino-6-bromo-pyrazin-2-yl)-pyridin-3-yl-methanone (Intermediate AA) with the appropriate pyrazine bromide. The pyrazine bromide is prepared as outlined in section 'Preparation of intermediate compounds'. $^1$H NMR (400 MHz, DMSO-d6) δ 8.60 (1H, d), 8.47 (1H, dd), 8.35 (1H, s), 8.07-806 (1H, m), 7.95 (1H, dt), 7.83-7.80 (2H, m), 7.65 (1H, dt), 7.56 (1H, t), 7.54 (1H, dd), 6.99 (2H, s), 2.06 (1H, m), 0.42-0.36 (2H, m), 0.34-0.30 (2H, m); MS m/z No ion [M+H]$^+$

Example 102

5-(5-Amino-pyrazin-2-yl)-2-chloro-N-(4-hydroxy-cyclohexyl)-benzenesulfonamide (Ex. 102)

A suspension of 5-bromo-2-chloro-N-(4-hydroxy-cyclohexyl)-benzenesulfonamide (Intermediate DJ) (0.1 g, 0.27 mmol), bis(pinacolato)diboron (0.07 g, 0.29 mmol), Pd(dppf)Cl$_2$.DCM (0.011 g, 0.014 mmol) and potassium acetate (0.04 g, 0.40 mmol) in DME (3 ml) is heated at reflux for 1.5 hours. Pd(dppf)Cl$_2$.DCM (0.011 g, 0.014 mmol), 2-amino-5-bromopyrazine (0.05 g, 0.29 mmol), 2M Na$_2$CO$_3$ (1.5 ml) and DME (1 ml) are added and the reaction heated at reflux for 1 hour. The reaction mixture is purified by reverse phase column chromatography (C18, 0-100% MeCN in water –0.1% TFA) to yield a solid which was dried in vacuo at 45° C. overnight to yield the title compound. $^1$H NMR (400 MHz, DMSO-d6) δ 8.60 (1H, d), 8.55 (1H, d), 8.14 (1H, dd), 8.00 (1H, d), 7.85 (1H, d), 7.67 (1H, d), 7.14-6.45 (2H, br hump), 3.30-3.24 (1H, m), 3.02-2.93 (1H, m), 1.73-1.68 (2H, m), 1.64-1.60 (2H, m), 1.33-1.23 (2H, m) 1.10-1.00 (2H, m); MS m/z 383 [M+H]$^+$

Examples 103-104

These compounds namely,
5-(5-Amino-pyrazin-2-yl)-2,4-difluoro-N-(2-methoxy-ethyl)-benzenesulfonamide (Ex. 103), $^1$H NMR (400 MHz, DMSO-d6) δ 8.37 (1H, dd), 8.32 (1H, t), 8.09 (1H, t), 8.04 (1H, d), 7.64 (1H, t), 6.95 (2H, br s), 3.30 (2H, t), 3.10 (3H, s), 3.05 (2H, q); MS m/z 345 [M+H]$^+$ 5-(5-Amino-pyrazin-2-yl)-N-(4-hydroxy-cyclohexyl)-2-trifluoromethyl-benzenesulfonamide (Ex. 104), $^1$H NMR (400 MHz, DMSO-d6) δ 8.70-8.69 (2H, m), 8.31 (1H, d), 8.02 (1H, d), 7.97 (1H, d), 7.95 (1H, d), 6.93 (2H, s), 4.46 (1H, br s), 3.07-2.99 (1H, m), 1.74-1.66 (4H, m), 1.34-1.23 (2H, m), 1.12-1.02 (2H, m); MS m/z 458 [M+H]$^+$ are prepared by an analogous procedure to Example 102 by replacing of 5-bromo-2-chloro-N-(4-hydroxy-cyclohexyl)-benzenesulfonamide (Intermediate DJ) with the appropriate sulfonamide. The compounds are recovered from reaction mixtures and purified by reverse phase column chromatography.

Example 105

{3-Amino-6-[3-(morpholine-4-sulfonyl)-phenyl]-pyrazin-2-yl}-pyridin-3-yl-methanone This compound is prepared analogously to Example 1 by replacing 5-(4,4,5,5-tetramethyl-[1,3,2]-dioxaborolan-2-yl)-3-trifluoromethyl-pyridin-2-ylamine (Intermediate K) with the appropriate boronic acid. $^1$H NMR (400 MHz, DMSO-d6) δ 9.21 (1H, s), 9.18 (1H, d), 8.86 (1H, dd), 8.38 (2H, m), 8.24 (2H, s), 8.22 (1H, m), 7.82 (2H, m), 7.65 (2H, dd), 3.72 (4H, t), 2.94 (4H, t); MS m/z 426 [M+H]$^+$

Example 106

5-[5-Amino-6-(pyridine-3-carbonyl)-pyrazin-2-yl]-2-chloro-N-(2-methoxy-ethyl)-benzenesulfonamide This compound is prepared by an analogous procedure to Example 58 by replacing 3-bromo-N-(2-methoxy-ethyl)-benzenesulfonamide (Intermediate DD) with the appropriate halo compound. These are either commercially available or synthesised as described in section 'Preparation of Intermediate Compounds'.
$^1$H NMR (400 MHz, DMSO-d6) δ 9.10 (1H, s), 9.07 (1H, d), 8.81 (1H, dd), 8.47 (1H, d), 8.39 (1H, dt), 8.19 (2H, s), 8.16 (1H, dd), 7.97 (1H, t), 7.76 (1H, d), 7.60 (1H, dd), 3.30 (2H, t), 3.11 (3H, s), 3.05 (2H, q); MS m/z 448 [M+H]$^+$

Example 107

{3-(2-Methoxy-ethylamino)-6-[2-methyl-5-(morpholine-4-sulfonyl)-phenyl]-pyrazin-2-yl}-pyridin-3-yl-methanone (Ex. 107)

This compound is prepared in an analogous manner to Example 53, substituting 3-acetamidobenzene boronic acid (25.5 mg, 0.14 mmol) and [6-bromo-3-(2-methoxy-ethylamino)pyrazin-2-yl]pyridin-2yl-methanone (Intermediate AC) with the appropriate boronic acid and pyrazine bromide. The pyrazine bromides are prepared as described in section 'Preparation of Intermediate Compounds'.
$^1$H NMR (400 MHz, DMSO-d6) δ 9.07 (1H, d), 9.01 (1H, t), 8.75 (1H, s), 8.72 (1H, dd), 8.23 (1H, dt), 7.76 (1H, d), 7.64 (1H, m), 7.58 (1H, d), 7.51 (1H, ddd), 3.81 (2H, m), 3.64 (6H, m), 3.35 (3H, s) 2.84 (4H, m), 2.43 (3H, s); MS m/z 498 [M+H]$^+$

Example 108

5-[2-Methyl-5-(morpholine-4-sulfonyl)-phenyl]-N*3*-pyridin-3-yl-pyrazine-2,3-diamine A suspension of NaH (60% dispersion in oil) (12 mg, 0.298 mmol) is stirred in THF (3 ml). Pyridine-3-ylamine (28 mg, 0.293 mmol) is added and gas evolved. Once all gas production is stopped 3-Chloro-5-[2-methyl-5-(morpholine-4-sulfonyl)-phenyl]-pyrazin-2-ylamine (Intermediate M) (100 mg, 0.271 mmol) in THF (3 ml) is added. The reaction mixture is microwaved at 120° C. for 10 minutes. More NaH (60%) (33 mg, 0.813 mmol) is added to the reaction mixture and the sample is microwaved at 120° C. for 40 minutes. The reaction is quenched with water (100 ml) and evaporated to dryness in vacuo. The brown residue is purified by reverse phase column chromatography to yield the title compound as a brown glass. $^1$H NMR (400 MHz, DMSO-d6) δ 9.14 (1H, d), 8.99 (1H, s), 8.38-8.33 (3H, m), 7.81 (1H, s), 7.70 (1H, d), 7.66-7.60 (5H, m), 3.64 (4H, t), 2.88 (4H, t), 2.54 (3H, s); MS m/z 427 [M+H]$^+$

Example 109

N-{3-[5-Amino-6-(pyridine-3-carbonyl)-pyrazin-2-yl]-phenyl}-methanesulfonamide

Methanesulfonyl chloride (24.6 μl, 0.31 mmol) is added to a solution of Example 51 (68 mg, 0.21 mmol) in pyridine (1 ml) under N₂. The resulting solution is stirred at room temperature for 1.5 h. The solvent is removed in vacuo, and the residue purified by flash chromatography (SiO2, 0-7.5% MeOH in DCM) to yield the title compound; MS m/z 370 [M+H]⁺

Example 110

[3-Amino-6-(5-amino-2-methyl-phenyl)-pyrazin-2-yl]-methanone

This compound is prepared in an analogous manner to Example 47 by replacing 5-indoylboronic acid with the appropriate boronic acid. The compound is recovered from the reaction mixture and purified using conventional techniques; MS m/z 306 [M+H]⁺

Example 111

N-{3-[5-Amino-6-(pyridine-3-carbonyl)-pyrazin-2-yl]-4-methyl-phenyl}-acetamide

Acetic anhydride (19.7 ml, 0.21 mmol) is added to solution of Example 110 (48.5 mg, 0.15 mmol) in pyridine (1.5 ml), and the resulting solution is stirred at room temperature for 2 hours. The solvent is removed in vacuo and trituration with methanol and diethyl ether yields the title compound as a yellow solid; MS m/z 348 [M+H]⁺

Preparation of Intermediate Compounds

The following intermediates of formula (A)

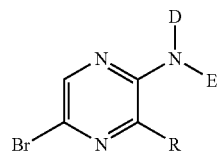

are shown in Table 2 below, their method of preparation being described hereinafter.

TABLE 2

| Intermediate | R | D | E | M/s MH+ |
|---|---|---|---|---|
| AA | 3-pyridinyl-C(=O)- | H | H | 279 |
| AB | 6-(trifluoromethyl)pyridin-3-yl-C(=O)- | H | H | 359 (M + Na) |
| AC | 3-pyridinyl-C(=O)- | H | -CH₂CH₂-O-CH₃ | 337 |
| AD | 3-pyridinyl-C(=O)- | H | -CH(CH₃)₂ (isopropyl) | No mass ion |
| AE | 3-pyridinyl-C(=O)- | R1-R2 joined | N-methylmorpholine | No mass ion |
| AF | 4-chlorophenyl-C(=O)- | H | H | 312 |
| AG | 4-fluorophenyl-C(=O)- | H | H | 296 |
| AH | phenyl-C(=O)- | H | H | 278 |
| AI | 3,5-difluorophenyl-C(=O)- | H | H | 314 |
| AJ | 3-pyridinyl-O-CH₃ | H | H | No mass ion |

Intermediate AA (3-Amino-6-bromo-pyrazin-2-yl)-pyridin-3-yl-methanone

Step 1

2,2,6,6 Tetramethyl piperidine (1.97 ml, 11.6 mmol) is added dropwise to a solution o of n-Butyl lithium (6.87 ml, 11.0 mmol of 1.6 M solution in THF) in THF (40 ml) at −78° C., and the resulting solution stirred at this temperature for 5 minutes. The reaction mixture is allowed to warm to 0° C. and the reaction stirred at this temperature for 35 minutes. The reaction is cooled to −78° C., and 2-chloropyrazine (0.78 ml, 8.73 mmol) is added dropwise to form a red solution, which is stirred at −78° C. for 40 minutes. Pyridine-3-carbaldehyde (0.93 ml, 9.95 mmol) is added dropwise and stirred at −78° C. for 1 hour and 40 minutes. The reaction is quenched using 5M HCl (5 ml) at −78° C. and the reaction then allowed to warm slowly to room temperature. The pH is adjusted to 7 by the addition of sat. aq. $NaHCO_3$ solution, and the product extracted into ethyl acetate (2×200 ml), dried ($MgSO_4$) and the solvent removed in vacuo to afford a black oil which is purified using flash chromatography ($SiO_2$, iso-hexane/EtOAc) to afford (3-chloro-pyrazin-2-yl)-pyridin-3-yl-methanol as a pale brown solid $[M+H]^+$ 222.

Step 2

$MnO_2$ (1.82 g, 20.95 mmol) is added to a solution of (3-chloro-pyrazin-2-yl)-pyridin-3-yl-methanol (929 mg, 4.19 mmol) in toluene (35 ml), and the reaction heated at reflux for 2 hours. The reaction is allowed to cool to room temperature and filtered through a pad of celite, which is washed with toluene. The solvent is removed in vacuo to afford (3-Chloro-pyrazin-2-yl)-pyridin-3-yl-methanone as a pale brown solid which is used in step 3 with no further purification $[M+H]^+$ 220.

Step 3

A solution of (3-Chloro-pyrazin-2-yl)-pyridin-3-yl-methanone (727 mg, 3.31 mmol) and 7M $NH_4$ in methanol (20 ml) is heated at 110° C. and 3.5 Bar pressure for 5 hours, and allowed to cool to room temperature. After standing at room temperature, orange crystals form which are collected by filtration and washing with methanol affords (3-amino-pyrazin-2-yl)-pyridin-3-yl-methanone as orange crystals $[M+H]^+$ 201.

Step 4

(3-Amino-pyrazin-2-yl)-pyridin-3-yl-methanone (1.00 g, 4.99 mmol) is dissolved in glacial acetic acid (10 ml). $Na_2CO_3$ (0.583 g, 5.49 mmol) is added. After evolution of gas has finished, a solution of bromine (0.192 ml, 3.74 mmol) in acetic acid (5 ml) is added dropwise. $Na_2CO_3$ (0.583 mg, 5.49 mmol) is added, followed by a second solution of bromine (0.192 ml, 3.74 mmol) in acetic acid (5 ml). The resulting orange suspension is left to stir for 1 hour. The reaction is quenched by pouring onto ice water (150 ml), and the orange solid formed is collected by filtration, washed with water and dried in vacuo at 40° C. overnight to yield the title compound. $[M+H]^+$ 279.

Intermediate AB (3-Amino-6-bromopyrazin-2-yl)-(6-(trifluoromethyl)pyridine-3-yl)methanone This compound can be synthesised in an analogous manner to intermediate AA by replacing pyridine-3-carbaldehyde in step 1 with 6-(trifluoromethyl)pyridine-3-carboxaldehyde.

Step 1

Yields (3-Chloroprazin-2-yl)pyridine-2-yl-methanol $[M+Na]^+$ 244

Step 2

Yields (3-Chloropyrazin-2-yl)(6-trifluoromethyl)pyridine-3-yl)methanone $[M+H]^+$ 288

Step 3

Yields (3-Aminopyrazin-2-yl)(6-(tifluoromethyl)pyridine-3-yl)methanone. $^1$H NMR (400 MHz, DMSO-d6) δ 9.09 (1H, d), 8.42 (1H, dd), 8.36 (1H, d), 8.03 (1H, d), 7.95 (3H, m)

Step 4

Yields (3-Amino-6-bromopyrazin-2-yl)-(6-(trifluoromethyl)pyridine-3-yl)methanone, $^1$H NMR (400 MHz, DMSO-d6) δ 9.11 (1H, d), 8.52 (1H, s), 8.43 (1H, dd), 8.18 (2H, s), 8.06 (1H, d).

Intermediate AC

[6-Bromo-3-(2-methoxy-ethylmino)pyrazin-2-yl]-pyridin-3-yl-methanone

Steps 1 and 2 afford (3-Chloro-pyrazin-2-yl)-pyridin-3-yl-methanone as described for intermediate AA.

Step 3

A microwave tube is charged with (3-chloro-pyrazin-2-yl)-pyridin-3-yl-methanone (85 mg, 0.39 mmol), DME (2 ml) and 2-methoxyethylamine (0.95 g, 4.26 mmol) and the tube is sealed with a microwave cap. The mixture is heated at 120° C. for 15 hours, then the solvent is removed in vacuo. [3-(2-Methoxy-ethylamino)-pryazin-2-yl]-pyridin-3-yl-methanone is obtained by flash chromatography ($SiO_2$, toluene/EtOAc, 2:1)

Step 4

The title compound is prepared in an analogous manner to step 4 of intermediate AA. $[M+H]^+$ 337

Intermediate AD (6-Bromo-3-isopropylamino-pyrazin-2-yl)pyridine-3-yl-methanone This compound is prepared in an analogous manner to intermediate AC, replacing 2-methoxyethylamine with isopropylamine in step 3.

Step 3

Yields (3-Isopropylamino-pyrazin-2-yl)pyridine-3-yl-methanone $[M+H]+$ 243.

Step 4

Yields the title compound $[M+H]^+$ 321.

Intermediate E (6-Bromo-3-morpholin-4-yl-pyrazin-2-yl)pyridine-3-yl-methanone This compound is prepared in an analogous manner to Intermediate AC, replacing 2-methoxyethylamine with morpholine in step 3.

Step 3

(3-Morpholin-4-yl-pyrazin-2-yl)pyridine-3-yl-methanone $[M+H]+$ 271.

Step 4

Yields the title compound, $^1$H NMR (400 MHz, DMSO-d6) δ 8.09 (1H, dd), 8.81 (1H, dd), 8.47 (1H, s), 8.30 (1H, dt), 7.62 (1H, m), 3.59 (4H, t), 3.35 (4H, t).

Intermediate AF (3-Amino-6-bromo-pyrazin-2-yl)-4-chloro-phenyl)-methanone

Step 1

To a solution of 3-aminopyrazine-2-carboxylic acid (1 g, 7.2 mmol) in DMF (15 ml) is added EDC hydrochloride (1.7 g, 8.6 mmol), HOBt (1.16 g, 8.6 mmol), diisopropylethylamine (3.08 ml, 18 mmol) and N-methoxy-N-methylamine hydrochloride (0.84 g, 8.6 mmol), and the resulting solution is stirred at room temperature for 15 hours. The reaction is concentrated in vacuo, and sat. aq. NaHCO$_3$ (50 ml) is added to the residue. The product is extracted into EtOAc (3×60 ml), washed with sat. aq. NaCl (2×50 ml), dried (MgSO$_4$) and concentrated in vacuo to afford a yellow residue. Purification by flash chromatography (SiO$_2$, 0-5% MeOH in DCM) yields 3-amino-pyrazine-2-carboxylic acid methoxy-methylamide as a yellow solid.

Step 2

A solution of 0.9 M 4-chlorophenyl magnesium bromide in THF/toluene (9.15 ml, 8.24 mmol) is added dropwise to a solution of 3-amino-pyrazine-2-carboxylic acid methoxy-methylamide (0.5 g, 2.74 mmol) in THF (15 ml) at 0° C. The reaction is allowed to warm to room temperature and stirred for 1.5 hours. The reaction mixture is cooled to 0° C. and 2 M HCl (20 ml) is added. The product is extracted into EtOAc (3×40 ml), dried (MgSO$_4$) and concentrated in vacuo. Purification by flash chromatography (SiO$_2$, 0-5% MeOH in DCM) yields (3-Amino-pyrazin-2-yl)-(4-chloro-phenyl)-methanone as a yellow solid.

Step 3

(3-Amino-pyrazin-2-yl)-(4-chloro-phenyl)-methanone (0.51 g, 2.20 mmol) is dissolved in glacial acetic acid (10 ml). Na$_2$CO$_3$ (0.257 g, 2.4 mmol) is added. After evolution of gas has finished, a solution of bromine (0.169 ml, 3.30 mmol) in acetic acid (5 ml) is added dropwise. Na$_2$CO$_3$ (0.257 mg, 2.4 mmol) is added, followed by a second solution of bromine (0.169 ml, 2.4 mmol) in acetic acid (5 ml). The resulting yellow suspension is left to stir for 15 hours. The reaction is quenched by pouring onto ice water (150 ml), and stirring for 10 minutes. The bright yellow precipitate is collected by filtration and dried in vacuo at 40° C. to yield the title product. [M+H]+ 541

Intermediates AG-AI

These intermediates, namely
(3-Amino-6-bromo-pyrazin-2-yl)-(4-fluoro-phenyl)-methanone (Intermediate AG), [M+H]+ 296
(3-Amino-6-bromo-pyrazin-2-yl)-phenyl-methanone (Intermediate AH), [M+H]+ 278.
(3-Amino-6-bromo-pyrazin-2-yl)-(3,5-difluoro-phenyl)-methanone (Intermediate AI), [M+H]+ 314.
are prepared in an analogous manner to Intermediate AF, replacing 4-chlorophenyl magnesium bromide with the appropriate grignard reagent in step 2, and using the subsequent product in step 3.

Intermediate AJ

6-Bromo-3-(pyridin-3-yloxy)-pyrazin-2-ylamine

A solution of pyridin-3-ol (0.045 g, 0.47 mmol), sodium hydride (12 m g, 0.47 mmol) in DMF (2 ml) is stirred at room temperature for 20 minutes. 3,5-Dibromo-pyrazin-2-ylamine (0.1 g, 0.39 mmol) is added and the reaction is heated at 170° C. for 15 minutes in a microwave. The solvent is concentrated in vacuo and the residue is purified using flash chromatography (SiO$_2$, DCM/MeOH) to afford 6-bromo-3-(pyridin-3-yloxy)-pyrazin-2-ylamine. $^1$H NMR (400 MHz, DMSO-d6) δ 8.53 (1H, d), 8.47 (1H, dd), 7.78 (1H, s), 7.75 (1H, dt), 7.51 (1H, dd), 6.89 (2H, s).

Intermediate B

3-Amino-6-(3,4-cihloro-phenyl)-pyrazine-2-carboxylic acid methoxy-methyl-amide

Step 1

A solution of 3-amino-6-bromo-pyrazine-2-carboxylic acid (0.62 g, 2.8 mmol), HATU (1.3 g, 3.4 mmol) and di-isopropylethylamine (1.72 ml, 3.5 mmol) in DMF (20 ml) is stirred at room temperature for 5 minutes. N-Methoxy-N-methylamine hydrochloride (0.33 g, 3.4 mmol) is added and the reaction is stirred at room temperature for 2 hours. The solvent is concentrated in vacuo and the residue dissolved in EtOAc (30 ml), and washed with sat. aq. NaHCO$_3$ (20 ml), 0.1N HCl (20 ml), dried (MgSO$_4$) and concentrated in vacuo to yield a brown oil. Purification by flash chromatography (SiO$_2$, 30% EtOAc in iso-hexane) yields 3-amino-6-bromo-pyrazine-2-carboxylic acid methoxy-methyl-amide as a yellow solid [M+H]+ 261.

Step 2

A suspension of 3-amino-6-bromo-pyrazine-2-carboxylic acid methoxy-methyl-amide (0.2 g, 0.76 mmol) and 3,4 dichlorophenyl boronic acid (0.16 g, 0.83 mmol) in 2M Na$_2$CO$_3$ (2 ml) is stirred at room temperature for 5 minutes. DME (6 ml), and Pd(dppf)Cl$_2$.DCM (0.031 g, 0.03 mmol) are added and the reaction is heated at reflux for 15 hours. The crude reaction mixture is purified by reverse phase chromatography (Isolute™ C18, 0-100% MeCN in water −0.1% TFA) to afford a pale yellow solid. The solid is dissolved in DCM (50 ml), washed with 2M NaOH (30 ml), dried (MgSO$_4$) and concentrated in vacuo to yield the title compound as an off-white solid. [M+H]$^+$ 327

Intermediate C

3-Amino-6-[2-methyl-5-(morpholine-4-sulfonyl)-phenyl]-pyrazine-2-carboxylic acid methoxy-methyl amide This compound is prepared in an analogous manner to intermediate B substituting 3,4 dichlorophenyl boronic acid with 2-methyl-5-(N-morpholinylsulfonyl) phenyl boronic acid in step 2. The title compound is obtained as an off-white solid. [M+H]$^+$ 422.

Intermediate CA

2-Amino-5-[2,4-difluoro-5-(4-hydroxy-cyclohexyl-sulfamoyl)-phenyl]-N-methoxy-N-methyl-nicotinamide Step 1

A solution of 3-amino-6-bromo-pyrazine-2-carboxylic acid (0.62 g, 2.8 mmol), HATU (1.3 g, 3.4 mmol) and di-isopropylethylamine (1.72 ml, 3.5 mmol) in DMF (20 ml) is stirred at room temperature for 5 minutes. N-Methoxy-N-methylamine hydrochloride (0.33 g, 3.4 mmol) is added and the reaction is stirred at room temperature for 2 hours. The solvent is concentrated in vacuo and the residue dissolved in EtOAc (30 ml), and washed with sat. aq. NaHCO$_3$ (20 ml), 0.1N HCl (20 ml), dried (MgSO$_4$) and concentrated in vacuo to yield a brown oil. Purification by flash chromatography (SiO$_2$, 30% EtOAc in iso-hexane) yields 3-amino-6-bromo-pyrazine-2-carboxylic acid methoxy-methyl-amide as a yellow solid [M+H]$^+$ 261.

Step 2

A suspension of 5-bromo-2,4-difluoro-N-(4-hydroxy-cyclohexyl)-benzenesulfonamide-intermediate DX (300 mg, 0.81 mmol), BIS(pinacolato)diboron (222 mg, 0.88 mmol) and Pd(dppf)Cl$_2$.DCM (0.066 g, 0.08 mmol) in DME (12 ml) is heated at reflux for 4 hours. 2M Na2CO3 (4 ml) is added to the reaction mixture followed by 3-amino-6-bromo-pyrazine-2-carboxylic acid methoxy-methyl-amide (0.211 g, 0.81 mmol) and Pd(dppf)Cl$_2$.DCM (0.066 g, 0.08 mmol). The reaction mixture is refluxed for 30 minutes. The crude reaction mixture is purified by normal phase chromatography (30-100% EtOAc/iso-hexane) to afford a white solid as the titled compound. [M+H]+ 472

Intermediate CB

3-Amino-6-[3-(2-methoxy-ethylsulfamoyl)-phenyl]-pyrazine-2-carboxylicacid methoxy-methyl-amide This compound is prepared in an analogous manner to Intermediate CA by replacing 5-bromo-2,4-difluoro-N-(4-hydroxy-cyclohexyl)-benzenesulfonamide (Intermediate DX) in step 2 with 3-bromo-N-(2-methoxy-ethyl)-benzene sulfonamide (Intermediate DD). The title compound is obtained as brown glass. [M+H]+ 396.

The following intermediates of formula (D)

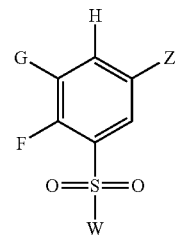

are shown in Table 3 below, their method of preparation being described hereinafter.

TABLE 3

| Intermediate | W | Z | F | G | H | M/s [M + H]+ |
|---|---|---|---|---|---|---|
| DA | 4-methyl-piperazin-1-yl | Br | H | H | H | 345 |
| DB | 4-cyclopropyl-piperazin-1-yl | Br | H | H | H | 319 |
| DC | cyclobutyl(methyl)amino | Br | H | H | H | No mass ion |
| DD | (2-methoxyethyl)(methyl)amino | Br | H | H | H | 296 |
| DE | (cyclopropylmethyl)(methyl)amino | Br | H | H | H | No mass ion |
| DF | (1-methyl-azepan-4-yl)(methyl)amino | Br | H | H | H | 334 |

TABLE 3-continued

| Intermediate | W | Z | F | G | H | M/s [M + H]⁺ |
|---|---|---|---|---|---|---|
| DG | 1-(2-hydroxyethyl)piperazin-4-yl (N-methyl) | Br | H | H | H | 351 |
| DH | 2-(4-methylpiperazin-1-yl)ethyl(methyl)amino | Br | H | H | H | 362 |
| DI | 4-isopropylpiperazin-1-yl (N-methyl) | Br | Cl | H | H | No mass ion |
| DJ | trans-4-hydroxycyclohexyl(methyl)amino | Br | Cl | H | H | No mass ion |
| DK | 4-methylpiperazin-1-yl (N-methyl) | Br | Cl | H | H | 353 |
| DL | morpholin-4-yl (N-methyl) | Br | Cl | H | H | 342 |
| DM | cyclopropyl(methyl)amino | Br | H | CF₃ | H | No mass ion |
| DN | morpholin-4-yl (N-methyl) | Br | F | H | F | No mass ion |

TABLE 3-continued

| Intermediate | W | Z | F | G | H | M/s [M + H]+ |
|---|---|---|---|---|---|---|
| DO | 4-methylpiperazin-1-yl | Br | F | H | F | 355 |
| DP | cyclopropylamino (N-methyl) | Br | F | H | F | No mass ion |
| DQ | 4-methylpiperazin-1-yl | Br | H | CF$_3$ | H | 389 |
| DR | morpholin-4-yl | Cl | CF$_3$ | H | H | 330 |
| DS | 4-methylpiperazin-1-yl | Cl | CF$_3$ | H | H | 343 |
| DT | (2-methoxyethyl)(methyl)amino | Cl | CF$_3$ | H | H | 318 |
| DU | cyclopropyl(methyl)amino | 4,4,5,5-tetramethyl-1,3,2-dioxaborolan-2-yl | H | H | CH$_3$ | No mass ion |
| DV | (cyclopropylmethyl)(methyl)amino | Br | F | H | F | No mass ion |

TABLE 3-continued

| Intermediate | W | Z | F | G | H | M/s [M + H]+ |
|---|---|---|---|---|---|---|
| DW | —NH—CH$_2$CH$_2$—O—CH$_3$ | Br | F | H | F | No mass ion |
| DX | —NH—(trans-cyclohexyl)—OH | Br | F | H | F | No mass ion |
| DY | —NH—(trans-cyclohexyl)—OH | Cl | CF3 | H | H | No mass ion |
| DZ | —NH—CH$_2$CH$_2$—O—CH$_3$ | Br | Cl | H | H | No mass ion |

Intermediate DA

1-(3-bromo-benzensulfonyl)-4-methyl-piperazine

A solution of 1-methylpiperazine (0.072 ml, 0.65 mmol) and 3-bromobenzene-1-sulfonyl chloride (0.2 g, 0.78 mmol) in pyridine (3 ml) is stirred at room temperature for 2 hours. The reaction mixture is diluted with 2M HCl, and extracted with DCM. The aqueous layer is made basic with 2M NaOH, and is extracted with DCM. The DCM layers are combined, dried (MgSO$_4$) and the solvent removed in vacuo to afford the title compound as an orange oil. [M+H]+ 345.

Intermediates DB-DH

These compounds, namely
1-(3-Bromo-benzenesuflonyl)-4-cyclopropyl-piperazine (Intermediate DB), [M+H]+ 319. 3-Bromo-N-cyclobutyl-benzenesulfonamide (Intermediate DC), $^1$H NMR (400 MHz, d6-DMSO) δ 8.2 (1H, d), 8.0 (1H, t), 7.93 (1H, m), 7.86 (1H, m), 7.63 (1H, t), 3.75 (1H, septet), 2.0 (2H, m), 1.82 (2H, m), 1.6 (2H, m),
3-Bromo-N-(2-methoxy-ethyl)-benzenesulfonamide (Intermediate DD), [M+H]+ 296.
3-Bromo-N-cyclopropylmethyl-benzenesulfonamide (Intermediate DE), $^1$H NMR (400 MHz, d6-DMSO) δ 7.86 (1H, t), 7.82 (1H, m), 7.77 (1H, m), 7.72 (1H, m), 7.48 (1H, t), 2.60 (2H, m), 0.7 (1H, m), 0.28 (2H, m), 0.01 (2H, m),
1-(3-Bromo-benzenesulfonyl)-4-methyl-[1,4]diazepane (Intermediate DF), [M+H]+ 334
2-[4-(3-Bromo-benzenesuflonyl)-piperazin-1-yl]-ethanol (Intermediate DG), [M+H]+ 351
3-Bromo-N-[2-(4-methyl-piperazin-1-yl)-ethyl]-benzenesulfonamide (Intermediate DH), [M+H]+ 351
are prepared in an analogous manner to Intermediate DA, substituting 1-methypiperazine with the appropriate amine. The compounds are recovered from reaction mixtures and purified using conventional techniques.

Intermediate DI

1-(5-Bromo-2-chloro-benzenesulfonyl)-4-isopropyl-piperazine

Step 1

A solution of 2-chloro-5-bromoaniline (0.99 g, 4.7 mmol) in glacial acetic acid (30 ml) and concentrated HCl (10 ml) is cooled to 0° C., and a solution of sodium nitrite (0.32 g, 4.7 mmol) in water (40 ml) is added dropwise. The resulting solution is allowed to warm to room temperature and stirred for 2 hours. A solution of SO$_2$/AcOH/CuCl$_2$/H$_2$O (100 ml) (the preparation of the reagent is described below) is added and the resulting bright green solution stirred at room temperature overnight. After this time, the reaction mixture is poured into water (400 ml) to give a milky liquid, which is extracted with ethyl acetate. The organic layer is washed with sat. aq. NaCl, dried (MgSO$_4$), and concentrated in vacuo to afford 5-Bromo-2-chloro-benzenesulfonyl chloride as a cream solid, which is used crude in step 2.

Preparation of the reagent SO$_2$/AcOH/CuCl$_2$/H$_2$O:

According to the reported procedure (E. E. Gilbert, Synthesis 1969, 1-10, p6), glacial acetic acid (100 ml) vigorously stirred at room temperature is treated by bubbling SO$_2$ gas. Once a saturated solution is achieved (approximately 10 g per 100 ml), the solution is treated with copper (II) chloride (4 g) in water (5 ml). The resulting mixture is allowed to settle to give a green solution.

Step 2

5-Bromo-2-chloro-benzenesulfonyl chloride (0.2 g, 0.69 mmol) is added to a solution of 1-isopropyl-piperazine (0.19 g, 1.45 mmol) in DCM (5 ml) and the resulting solution stirred at room temperature overnight. The reaction mixture is diluted with DCM, and washed with sat. aq. NaHCO$_3$ solution, dried (MgSO$_4$) and the concentrated in vacuo to yield the title compound. $^1$H NMR (400 MHZ, d6-DMSO) δ 8.11 (1H, d), 7.99 (1H, dd), 7.76 (1H, d) 3.24 (4H, t) 2.75-2.71 (1H, m) 2.52 (4H, t) 1.00 (6H, d).

Intermediates DJ-DL and DZ

These compounds, namely 5-Bromo-2-chloro-N-(4-hydroxy-cyclohexyl)-benzenesulfonamide (Intermediate DJ), $^1$H NMR (400 MHz, d6-DMSO) δ 8.07 (1H, d), 8.03 (1H, s), 7.85 (1H, dd), 7.64 (1H, d), 4.49 (1H, d), 2.99 (1H, s), 1.73 (2H, d), 1.60 (2H, d), 1.28-1.19 (2H, m), 1.14-1.04 (2H, m),
1-(5-Bromo-2-chloro-benzenesulfonyl)-4-methyl-piperazine (Intermediate DK), [M+H]+ 353,
5-(5-Bromo-2-chloro-benzenesulfonyl)-morpholine (Intermediate DL), [M+H]+ 342,
5-Bromo-2-chloro-N-(2-methoxy-ethyl)-benzenesulfonamide (Intermediate DZ), $^1$H NMR (400 MHz, d6-DMSO) δ 8.13 (1H, br s), 8.06 (1H, d), 7.84 (1H, dd), 7.62 (2H, d), 3.28 (2H, t), 3.10-3.08 (5H, m),
are prepared in an analogous manner to Intermediate DI substituting 1-isopropyl-piperazine with the appropriate amine.

Intermediate DM

3-Bromo-N-cyclopropyl-5-trifluoromethyl-benzenesulfonamide

3-Bromo-5-(trifluoromethyl)benzenesulfonyl chloride (0.2 g, 0.62 mmol) is added to a solution of cyclopropylamine (0.09 μl, 1.3 mmol) in DCM (5 ml), and the resulting solution is stirred at room temperature overnight. The reaction mixture is diluted with DCM (2×10 ml), washed with 0.1M HCl (5 ml), sat. aq. NaHCO$_3$ (5 ml), dried (MgSO$_4$) and concentrated in vacuo to yield the title compound. $^1$H NMR (400 MHz, d6-DMSO) δ 8.37 (1H, s), 8.23 (1H, s), 8.06 (1H, s), 2.21-2.17 (1H, m), 0.55-0.50 (2H, m) 0.40-0.36 (2H, m).

Intermediates DN-DQ, DV-DX

These compounds, namely 4-(5-Bromo-2,4-difluoro-benzenesulfonyl)-morpholine (Intermediate DN), $^1$H NMR (400 MHz, d6-DMSO) δ 8.03 (1H, t) 7.89 (1H, d), 3.64 (4H, t), 3.07 (4H, t),
1-(5-Bromo-2,4-difluoro-benzenesulfonyl)-4-methyl-piperazine (Intermediate DO), [M+H]+ 355.
5-Bromo-N-cyclopropyl-2,4-difluoro-benzenesulfonamide (Intermediate DP), $^1$H NMR (400 MHz, d6-DMSO) δ 8.41 (NH, s), 8.04 (1H, t), 7.82 (1H, dd), 2.29-2.25 (1H, m), 0.54-0.49 (2H, m), 0.42-0.38 (2H, m),
1-(3-Bromo-5-trifluoromethyl-benzenesulfonyl)-4-methyl-piperazine (Intermediate DQ), [M+H]+ 389.
5-Bromo-N-cyclopropylmethyl-2,4-difluoro-benzenesulfonamide (Intermediate DV), $^1$H NMR (400 MHz, d6-DMSO) δ 7.24 (1H, t), 6.52 (1H, dd), 2.01 (2H, d), 0.01 (1H, m), −0.44 (2H, m) −0.73 (2H, m).
5-Bromo-2,4-difluoro-N-(2-methoxy-ethyl)-benzenesulfonamide (Intermediate DW) (QBI798), $^1$H NMR (400 MHz, d6-DMSO) δ 7.31 (1H, t), 6.60 (1H, dd), 2.59 (2H, td), 2.40 (3H, s), 2.38 (2H, t).
5-Bromo-2,4-difluoro-N-(4-hydroxy-cyclohexyl)-benzenesulfonamide (Intermediate DX) (QBI797), $^1$H NMR (400 MHz, d6-DMSO) δ 7.32 (1H, t), 6.60 (1H, dd), 2.69-2.62 (1H, m), 2.35-2.29 (1H, m), 1.08-1.05 (2H, m), 0.99-0.96 (2H, m), 0.57-0.39 (4H, m).
are prepared in an analogous manner to Intermediate DM by substituting 3-bromo-5-(trifluoromethyl)benzenesulfonyl chloride and cyclopropylamine with the appropriate sulfonyl chloride and amine.

Intermediate DR 4-(5-chloro-2-trifluoromethyl-benzenesulfonyl)-morpholine

Step 1

To a stirred solution of 2-(trifluoromethyl)-5-chloro-aniline (3.9 g, 19.5 mmol) in glacial acetic acid (120 ml) and conc. HCl (39 ml) is added sodium nitrite (1.39 g, 19.5 mmol) in water (16 ml). The reaction mixture is allowed to warm to room temperature and stirred for 3 hours, then added to a solution of SO$_2$/AcOH/CuCl$_2$/H$_2$O (400 ml) (preparation of reagent described under Intermediate DI), and stirred at room temperature for 18 hours. The reaction mixture is poured onto ice/water (1.5 L), and extracted with EtOAc (3×300 ml). The combined organic layers are washed with 1N HCl and water, and dried (Na$_2$SO$_4$). Concentration in vacuo yields 5-Chloro-2-trifluoromethyl-benzenesulfonyl chloride.

Step 2

5-Chloro-2-trifluoromethyl-benzenesulfonyl chloride (0.17 g, 0.62 mmol) is added to a solution of morphline (0.114 ml, 1.3 mol) in DCM (5 ml) and the resulting white suspension is stirred at room temperature overnight. The reaction mixture is diluted with DCM (5 ml), and washed with 0.1M HCl, dried (MgSO$_4$) and concentrated in vacuo to yield the title compound. [M+H]+ 330.

Intermediates DS, DT and DY

These compounds, namely
1-(5-Chloro-2-trifluoromethyl-benzenesulfonyl)-4-methyl-piperazine (Intermediate DS), [M+H]+ 343.
5-Chloro-N-(2-methoxy-ethyl)-2-trifluoromethyl-benzenesulfonamide (Intermediate DT), [M+H]+ 318
5-Chloro-N-(4-hydroxy-cyclohexyl)-2-trifluoromethyl-benzenesulfonamide (Intermediate DY), $^1$H NMR (400 MHz, DMSO-d6) δ 8.14 (1H, d), 8.08 (1H, s), 8.00 (1H, d), 7.93 (1H, d), 7.91 (1H, d), 4.50 (1H, d), 3.34-3.26 (1H, m), 3.08-3.02 (1H, m), 1.75-1.72 (2H, m), 1.65-1.61 (2H, m), 1.32-1.22 (2H, m) 1.15-1.05 (2H, m).

are prepared in an analogous manner to Intermediate DR replacing morpholine with the appropriate amine.

Intermediate DU

Cyclopropanesulfonic acid [4-methyl-3-(4,4,5,5-tetramethyl-[1,3,2]-dioxaborolan-2-yl)-phenyl]-amide A solution of 5-amino-2-methylphenyl boronic acid, pinacol ester (0.138 g, 0.59 mmol) and cyclopropane sulfonyl chloride (0.1 g, 0.71 mmol) in pyridine (3 ml) is stirred at room temperature for 1 hours. The reaction mixture is diluted with 2M HCl, and extracted with DCM. The organic phase is dried (MgSO$_4$), concentrated and dried in vacuo at 45° C. for 6 hours to yield the title compound as a deep red oil. $^1$H NMR (400 MHz, d6-DMSO) δ 9.48 (1H, s), 7.51 (1H, d), 7.25 (1H, dd), 7.13 (1H, d), 2.42 (3H, s), 1.31 (1H, m), 1.30 (12H, s), 0.9 (4H, m).

Intermediate E

Cyclopropanecarboxylic acid [4-methyl-3-(4,4,5,5-tetramethyl-[1,3,2]dioxaborolan-2-yl)-phenyl]-amide A solution of 5-amino-2-methylphenyl boronic acid, pinacol ester (0.5 g, 2.14 mmol), cyclopropanecarbonyl chloride (0.22 ml, 2.35 mmol) and triethylamine (0.89 ml, 6.42 mmol) in DCM (10 ml) is stirred at room temperature for 3 hours. 2M HCl is added and the product is extracted with DCM, and dried (MgSO$_4$). Concentration in vacuo, followed by trituration with EtOH yields the title compound as a pink solid. $^1$H NMR (400 MHz, d$_6$-DMSO) d 10.1 (1H, s), 7.89 (1H, d), 7.68 (1H, dd), 7.1 (1H, d), 2.4 (3H, s), 1.75 (1H, m), 1.32 (12H, s), 0.78 (4H, m).

Intermediate F

6-Chloro-5-(phenylsulfonamido)pyridin-3-ylboronic acid

Step 1
A solution of DMAP (0.012 g, 0.096 mmol), 5-bromo-2-chloropyridin-3-amine (0.2 g, 0.96 mmol) and benzene sulfonyl chloride (0.61 ml, 4.8 mmol) in pyridine (0.16 ml, 1.92 mmol) is heated at 50° C. overnight. The reaction is cooled to room temperature and absorbed onto silica. Purification by flash chromatography (SiO2, 10-20% EtOAc in iso-hexane) yields N-(5-Bromo-2-chloro-pyridin-3-yl)-benzenesulfonamide as a white solid. [M+H]$^+$ 347.
Step 2
Triisopropyl borate (5.69 ml, 24.7 mmol) is added to a solution of N-(5-Bromo-2-chloro-pyridin-3-yl)-benzenesulfonamide (1 g, 2.87 mmol) in anhydrous THF (25 ml) under argon, and the resulting solution is cooled to −78° C. A 1.6 M solution of n-butyl lithium in hexanes (5.39 ml, 8.63 mmol) is added dropwise keeping the temperature below −70° C. The reaction is stirred at −78° C. for 50 minutes. The reaction is quenched with sat. aq. NaCl (20 ml) at −78° C. and then allowed to warm to room temperature and washed with EtOAc. The aqueous layer is concentrated in vacuo, and the residue is dissolved in 2.5M HCl, and the product is extracted into EtOAc, dried (MgSO$_4$) and concentrated in vacuo to yield the title compound as a yellow oil. [M+H]$^+$ 313.

The following intermediates of formula (G)

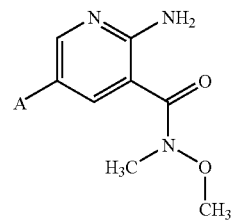

are shown in Table X below, their method of preparation being described hereinafter.

| Intermediate | A | M/s MH+ |
|---|---|---|
| GA | ![structure with sulfonamide, cyclopropyl-NH, phenyl with methyl] | 377 |
| GB | ![Cl-phenyl-CH3 dimethyl] | 306 |

Intermediate GA 2-amino-5-(3-cyclopropylsulfamoyl-phenyl)-N-methoxy-N-methyl-nicotinamide Step 1
To a solution of 2-Amino-5-bromonicotinic acid (1 g, 4.6 mmol) in DMF (15 ml) is added EDC hydrochloride (1.06 g, 5.53 mmol), HOBt (0.747 g, 5.53 mmol), diisopropylethylamine (2 ml, 11.5 mmol) and N-methoxy-N-methylamine hydrochloride (0.54 g, 5.53 mmol), and the resulting solution is stirred at room temperature overnight. The reaction is concentrated in vacuo, and the residue is dissolved in EtOAc, washed with sat. aq. NaHCO$_3$, dried (MgSO$_4$) and concentrated in vacuo. Purification by flash chromatography (SiO$_2$, 0-10% ethanol in DCM) yields 2-Amino-5-bromo-N-methoxy-N-methyl-nicotinamide.
Step 2
A suspension of 2-Amino-5-bromo-N-methoxy-N-methyl-nicotinamide (0.2 g, 0.77 mmol), N-cyclopropyl 3-boronobenzenesulfonamide (0.2 g, 0.84 mmol), Pd(dppf)Cl$_2$.DCM (0.063 g, 0.077 mmol) in 2M Na$_2$CO$_3$ (1 ml) and DME (3 ml) is heated at reflux for 1 hour. The crude reaction mixture is subjected to column chromatography (Isolute™ C18, 0-100% MeCN in water −0.1% TFA). All the acetonitrile is removed in vacuo, and the aqueous solution remaining is adjusted to basic pH using NaHCO$_3$. The product is extracted into DCM, and dried (MgSO$_4$). Concentration and drying in vacuo at 40° C. yields the title compound. [M+H]+ 726

Intermediate GB

2-Amino-5-(3-chloro-5-methyl-phenyl)-N-methoxy-N-methyl-nicotinamide

This compound can be made in an analogous manner to 2-amino-5-(3-cyclopropylsulfamoyl-phenyl)-N-methoxy-N-methyl-nicotinamide (Intermediate GA), [M+H]+ 698, substituting N-cyclopropyl 3-boronobenzenesulfonamide with 4-Chloro-2-methylphenylboronic acid.

Intermediate H (2-Amino-5-bromo-pyridin-3-yl)-pyridin-3-yl-methanone

Step 1
TMEDA (2.54 ml, 16.8 mmol) is added to a solution of pivaloylamino pyridine (1 g, 5.6 mmol) in diethyl ether (40 ml), and the resulting solution is cooled to −70° C. A solution of 2.5M N-Butyl lithium in hexanes (6.73 ml, 16.8 mmol) is added dropwise to the solution, which turns a golden yellow colour. The solution is allowed to warm to −20° C. and stirred at this temperature for 2 hours. The solution is cooled to −70° C. and a solution of pyridine-3-carbaldehyde (1.16 ml, 12.3 mmol) in THF (20 ml) is added and resulting suspension is allowed to warm to room temperature and stirred overnight. H$_2$O is added and the phases are separated, the aqueous phase is washed with DCM, and the organic phases combined, and concentrated in vacuo to afford a yellow oil. Purification by flash chromatography (SiO$_2$, 70-100% EtOAc in iso-hexane), and drying in vacuo at 45° C. overnight yields N-[3-(hydroxyl-pyridin-2-yl-methyl)-pyridin-2-yl]-2,2-dimethyl-propionamide [M+H]$^+$ 286.
Step 2
A suspension of N-[3-(hydroxyl-pyridin-2-yl-methyl)-pyridin-2-yl]-2,2-dimethyl-propionamide (0.73 g, 2.55 mmol) and MnO$_2$ (1.11 g, 12.76 mmol) in toluene (15 ml) is heated at reflux for 1 hour. The reaction mixture is filtered hot through Celite®, which is washed with further toluene. Concentration in vacuo, followed by purification by flash chromatography (SiO$_2$, 50-100% EtOAc in is-hexane) and drying in vacuo at 45° C. overnight yields as a 2,2-dimethyl-N-[3-(pyridine-3-carbonyl)-pyridin-2-yl]-propionamide as a white solid [M+H]$^+$ 284.
Step 3
A solution of 2,2-dimethyl-N-[3-(pyridine-3-carbonyl)-pyridin-2-yl]-propionamide (0.225 g, 0.79 mmol) in 3M HCl (10 ml) is heated at reflux for 4 hours. The reaction mixture is allowed to cool to room temperature and the pH adjusted to basic with 2M NaOH. The product is extracted into DCM, dried (MgSO$_4$), and concentrated in vacuo to afford a yellow solid. Drying in vacuo at 45° C. overnight yields (2-Amino-pyridin-3-yl)-pyridin-3-yl-methanone [M+H]$^+$ 200.
Step 4
(2-Amino-pyridin-3-yl)-pyridin-3-yl-methanone (0.13 g, 0.65 mmol) is dissolved in glacial acetic acid (6 ml). Na$_2$CO$_3$ (0.075 g, 0.72 mmol) is added. After evolution of gas has finished, a solution of bromine (0.025 ml, 0.49 mmol) in acetic acid (3 ml) is added dropwise. Na$_2$CO$_3$ (0.075 g, 0.72 mmol) is added, followed by a second solution of bromine (0.025 ml, 0.49 mmol) in acetic acid (3 ml). The resulting yellow suspension is left to stir for 2 hour. The reaction is quenched by pouring onto ice water (150 ml), and neutralised using NaHCO$_3$. The product is extracted with EtOAc and dried (MgSO$_4$). Concentration in vacuo affords an oil, which is trituatuted with methanol to yield the title compound [M+H]$^+$ 277.

Intermediate I (3-Amino-6-bromo-5-methyl-pyrazin-2-yl)-phenyl-methanone

Step 1:
7-Methyl-pteridine-2,4-diol (prepared by the procedure of 'Synthesis of 2,6-Disubstituted pyrazines and Related Derivates', Sharefkin, D. M. J. Am. Chem. Soc., 1959, 345) (4 g, 22.5 mmol) is suspended in a solution of NaOH (2.17 g, 53 mmol) in H$_2$O (20 ml), in an autoclave, and the mixture is heated to 150° C. for 3 days. The reaction mixture is cooled to room temperature and the pH is adjusted to 2.5 by the slow addition of 6M HCl (98 ml). The resulting suspension is cooled in a fridge for 1.5 hours, and the solid is then collected by filtration, washed with cold H$_2$O, and MeOH, and dried in vacuo to yield 3-amino-5-methyl-pyrazin-2-carboxylic acid as a beige solid. [M+H]$^+$ 154
Step 2
3-Amino-5-methyl-pyrazin-2-carboxylic acid (0.48 g, 3.12 mmol) is dissolved in anhydrous DMF (10 ml) under N$_2$. The brown solution is cooled to 0° C., and diisopropylethylamine (1.48 ml, 7.9 mmol), EDC.HCl (0.75 g, 3.8 mmol), HOBt (0.58 g, 3.8 mmol) and N,O-dimethoxyhydroxylamine hydrochloride (0.37 g, 3.8 mmol) are added and the reaction is stirred at 0° C. for 1 hour and at room temperature for 4 hours. The solvent is concentrated in vacuo, and the residue is diluted with EtOAc and aq. NaHCO$_3$. The phases are separated and the aqueous layer washed with EtOAc. The organic layers are combined, washed with brine, dried (MgSO$_4$) and concentrated in vacuo. Purification by flash chromatography (SiO$_2$, 0-5% MeOH in DCM) yields 3-amino-5-methyl-pyrazin-2-carboylic acid methoxy-methyl-amide as a pale yellow solid. [M+H]$^+$ 197.
Step 3
3-Amino-5-methyl-pyrazin-2-carboylic acid methoxy-methyl-amide (0.3 g, 1.53 mmol) is dissolved in anhydrous THF (30 ml) under N$_2$. The clear yellow solution is cooled to −78° C., and a 1M solution of phenyl magnesium bromide in THF (7.6 ml, 7.6 mmol) is added. The resulting reaction mixture is stirred at −78° C. for 1 hour, and is then allowed to warm to room temperature and stirred for a further 2.5 hours. The reaction mixture is poured onto aq. NaHCO$_3$ and EtOAc. The phases are separated and the aqueous layer is washed with EtOAc. The combined organic layers are washed with brine, dried (MgSO$_4$) and concentrated in vacuo. Purification by flash chromatography (SiO$_2$, 0-7% MeOH in DCM) yields (3-amino-5-methyl-pyrazin-2-yl)-phenyl-methanone as a yellow solid. [M+H]$^+$ 214.
Step 4
Potassium carbonate (0.23 g, 1.64 mmol) is dissolved in glacial acetic acid (5 ml, 1.64 mmol) and (3-amino-5-methyl-pyrazin-2-yl)-phenyl-methanone (0.17 g, 0.82 mmol) and bromine (0.055 ml, 1.07 mmol) are added. The resulting yellow solution is stirred at room temperature for 1.5 hours. The solvent is removed in vacuo, and the residue is suspended in DCM, filtered and washed with DCM. The filtrated is concentrated and dried in vacuo to yield the title compound as a yellow solid. [M+H]$^+$ 292.

Intermediate J

5-(Trifluoromethyl)pyridin-3-ylboronic acid

Triethylborate (24 ml, 139 mmol) is added to a solution of 3-bromo-5-trifluoromethyl-pyridine (30 g, 133 mmol) in THF (300 ml) and the resulting pale yellow solution is cooled to −78° C. A solution of 1.6 M n-butyl lithium in hexanes (97 ml, 139 mmol) is added via cannula dropwise over 40 minutes, keeping the temperature below −65° C. Once addition is complete, the reaction mixture is allowed to warm slowly to room temperature and stirred for 1 hour. 1M HCl (200 ml) is added and the reaction mixture stirred for 15 minutes. The layers are separated and the organic layer is washed with 1M HCl (200 ml). The aqueous layers are combined and washed with EtOAc (2×250 ml). The pH of the aqueous phase is adjusted by the addition of 2M NaOH, and extracted with EtOAc (2×250 ml). Concentration in vacuo affords a solid, which is recyrstallised from EtOAc/iso-hexane to yield the title compound as a yellow solid [M+H]$^+$ 192.

Intermediate K

5-(4,4,5,5-Tetramethyl-[1,3,2]-dioxaborolan-2-yl)-3-trifluoromethyl-pyridin-2-ylamine The title compound is prepared by the procedure of 'PI-3 Kinase inhibitors and methods of their use.' Ni, Zhi-Jie; Pecchi, Sabina; Burger, Matthew; Han, Wooseok; Smith, Aaron; Atallah, Gordana; Bartulis, Sarah; Frazier, Kelly; Verhagen, Joelle; Zhang, Yanchen; Iwanowicz, Ed; Hendrickson, Tom; Knapp, Mark; Merritt, Hanne; Voliva, Charles; Wiesmann, Marion; Legrand, Darren Mark; Bruce, Ian; Dale, James; Lan, Jiong; Levine, Barry; Costales, Abran; Liu, Jie; Pick, Teresa; Menezes, Daniel. (Novartis) PCT Int. Appl. (2007), 236 pp. WO 2007/095591.

Intermediate L

1-(6-Bromo-2,3-dihydro-inol-1-yl)-ethanone

The compound is prepared by the procedure of 'Hydroxylation and bromination of indoline and tetrahydroquinoline in superacids.' Berrier, C.; Jacquesy, J. C.; Jouannetaud, M. P.; Renoux, A. New Journal of Chemistry (1987), 11(8-9), 605-9.

Intermediate M

3-Chloro-5-[2-methyl-5-(morpholine-4-sulfonyl)-phenyl]-pyrazin-2-ylamine

Step 1

To 2,3-Dichloro-pyrazine (18 g, 120.82 mmol), ammonium hydroxide (50 ml, 1280 mmol) is added and the reaction mixture is microwaved at 140° C. for 25 minutes. The reaction mixture is filtered and washed with water to yield 3-Chloro-pyrazin-2-ylamine.

Step 2

3-Chloro-pyrazin-2-ylamine (0.750 g, 5.79 mmol) is suspended in acetic acid (7 ml) with stirring at room temperature and sodium carbonate (0.675 g, 6.37 mmol) is added. When all the gas has evolved bromine (0.171 ml, 3.34 mmol) in acetic acid (4 ml) is added dropwise. Sodium carbonate (0.675 g, 6.37 mmol) is added and a gas evolves. Once all gas has evolved bromine (0.171 ml, 3.34 mmol) in acetic acid (4 ml) is added. The reaction mixture is stirred at room temperature for 1 hour. The reaction mixture is poured onto iced water and left to stir for 30 minutes. A pale yellow suspension has formed. This solid is filtered off and rinsed with cold water to give 5-Bromo-3-chloro-pyrazin-2-ylamine.

Step 3

5-Bromo-3-chloro-pyrazin-2-ylamine (0.600 g, 2.88 mmol), 2-methyl-5-(N-morpholinylsulfonyl)phenylboronic acid (0.821 g, 2.88 mmol), 1,1'BIS(Diphenylphosphino-ferrocene)dichloropalladium (II) complex with DCM (0.118 g, 0.14 mmol), 2N Na$_2$CO$_3$ (aq.) (5 ml) and DME (15 ml) are stirred together at 100° C. for 1 hour. Product is purified by reverse phase chromatography and evaporation of the clean fractions yields a cream solid. The solid is dissolved in DCM (100 ml) and washed with 2N NaOH (aq.) (50 ml). The organic phase is dried over magnesium sulphate, filtered and the solvent evaporated to yield an orange semi-solid. This is dissolved ethyl acetate (10 ml) and iso-hexane is added. A precipitate forms and is filtered off to yield the title compound as an off white solid. [M+H]$^+$ 410.

The invention claimed is:
1. A compound of formula I

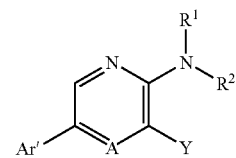

or a pharmaceutically acceptable salt thereof, wherein:
R$^1$ and R$^2$ are each independently selected from hydrogen and C$_1$-C$_6$ alkyl;
Y is selected from —C(O)C$_3$-C$_8$ cycloalkyl, —C(O)aryl, and —C(O)heteroaryl, where the cycloalkyl, aryl and heteroaryl ring systems are each optionally substituted by one or more substituents selected from List X;
A is N;
List X is represented by hydroxy, halo, cyano, nitro, C$_1$-C$_6$-alkyl, C$_3$-C$_8$ cycloalkyl, C$_1$-C$_3$ alkyl-C$_3$-C$_8$ cycloalkyl, —OC$_1$-C$_6$-alkyl, —OC$_3$-C$_8$ cycloalkyl, —OC$_1$-C$_3$ alkyl-C$_3$-C$_8$ cycloalkyl, where each of the alkyl groups are optionally substituted by one or more halogen, hydroxy, or cyano;
Ar' is a group

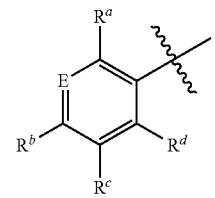

wherein
E is N or CR$^e$;
R$^a$ is selected from H, halo, C$_1$-C$_6$ alkyl, C$_1$-C$_6$ haloalkyl, OC$_1$-C$_6$ alkyl and —OC$_1$-C$_6$ haloalkyl;
R$^b$ is selected from H, —NR$^{40}$R$^{41}$, halo, C$_1$-C$_6$ alkyl, C$_1$-C$_6$ haloalkyl, —OC$_1$-C$_6$ alkyl and —OH;
R$^c$ is (CH$_2$)$_c$NR$^{44}$S(O)$_2$R$^{45}$;
R$^d$ is selected from H, C$_1$-C$_6$ alkyl and —OC$_1$-C$_6$ alkyl;
R$^e$ is selected from H, C$_1$-C$_3$ alkyl, C$_1$-C$_3$ haloalkyl and halo;

$R^{40}$, $R^{42}$ and $R^{44}$ are each independently selected from H and $C_1$-$C_6$ alkyl;

$R^{41}$ and $R^{43}$ are each independently selected from H, $C_1$-$C_6$ alkyl, $C_3$-$C_6$ cycloalkyl, $C_1$-$C_3$ alkyl-$C_3$-$C_6$ cycloalkyl, $C_1$-$C_3$ alkyl-aryl, $C_1$-$C_3$ alkyl-heterocyclyl, aryl, heterocyclyl, C(O)$C_1$-$C_6$ alkyl and $C_1$-$C_3$ alkyl-O$C_1$-$C_3$ alkyl, wherein the cycloalkyl ring is optionally substituted by one or more substituents selected from —OH and —$NH_2$;

$R^{45}$ is selected from $C_1$-$C_6$ alkyl, $C_3$-$C_6$ cycloalkyl, $C_1$-$C_3$ alkyl-$C_3$-$C_6$ cycloalkyl, —$NR^{42}R^{43}$, aryl and heterocyclyl;

a and b are each independently 0, 1, 2, or 3;

c is 1 or 2; and heterocyclyl is a 5- to 7-membered nitrogen-containing heterocyclic group which is optionally substituted by one or more groups selected from —OH, $C_1$-$C_3$ alkyl, $C_3$-$C_6$ cycloalkyl, $C_1$-$C_3$ alkyl-$C_3$-$C_6$ cycloalkyl and $C_1$-$C_3$ hydroxyalkyl;

provided that when Y is a ketone group, then Ar' is not a phenyl group substituted in the 3-position by a benzyl substituted amide group.

2. The compound according to claim 1, wherein Y is selected from —C(O)aryl and —C(O)heteroaryl, where the —C(O)aryl and —C(O)heteroaryl are each optionally substituted by one or more substituents selected from List X.

3. The compound according to claim 2, wherein aryl is phenyl and heteroaryl is selected from 5- and 6-membered nitrogen-containing heteroaromatic groups.

4. A pharmaceutical composition comprising a compound of claim 1, or a pharmaceutically acceptable salt thereof, and a pharmaceutically acceptable excipient.

5. A compound selected from

[3-Amino-6-(6-amino-5-trifluoromethyl-pyridin-3-yl)-pyrazin-2-yl]-pyridin-3-yl-methanone, {3-Amino-6-[2-methyl-5-(morpholine-4-sulfonyl)-phenyl]pyrazin-2-yl}-pyridin-3-yl-methanone, N-{5-[5-Amino-6-(pyridine-3-carbonyl)-pyrazin-2-yl]-2-chloro-pyridin-3-yl}-benzenesulfonamide,

[3-Amino-6-(3-methanesulfonyl-phenyl)-pyrazin-2-yl]-pyridin-3-yl-methanone,

{3-Amino-6-[3-(pyrrolidine-1-sulfonyl)-phenyl]-pyrazin-2-yl}-pyridin-3-yl-methanone,

[3-Amino-6-(4-chloro-3-methyl-phenyl)-pyrazin-2-yl]-pyridin-3-yl-methanone,

N'-{3-[5-amino-6-(pyridine-3-carbonyl)-pyrazin-2-yl]-phenyl}-N,N-dimethyl-sulfamide,

[3-Amino-6-(5-methanesulfonyl-pyridin-3-yl)-pyrazin-2-yl]-pyridin-3-yl-methanone,

[3-Amino-6-(3-chloro-5-methyl-phenyl)-pyrazin-2-yl]-pyridin-3-yl-methanone,

3-[5-Amino-6-(pyridine-3-carbonyl)-pyrazin-2-yl]-N-cyclopropyl-benzenesulfonamide,

[3-Amino-6-(3,4-dichloro-phenyl)pyrazin-2-yl]-pyridin-3-yl-methanone,

Cyclopropanesulfonic acid {3-[5-amino-6-(pyridine-3-carbonyl)-pyrazin-2-yl]-4-methyl-phenyl}-amide, 5-[5-Amino-6-(pyridine-3-carbonyl)-pyrazin-2-yl]-2-chloro-N-phenyl-benzenesulfonamide,

[3-Amino-6-(4-chloro-3-trifluoromethyl-phenyl)-pyrazin-2-yl]-pyridin-3-yl-methanone,

[3-Amino-6-(3-chloro-phenyl)-pyrazin-2-yl]-pyridin-3-yl-methanone,

[3-Amino-6-(3-amino-4-chloro-phenyl)-pyrazin-2-yl]-pyridin-3-yl-methanone,

{3-Amino-6-[4-methoxy-3-morpholine-4-sulfonyl)-phenyl]-pyrazin-2-yl}-pyridin-3-yl-methanone,

[3-Amino-6-(6-chloro-pyridin-3-yl)-pyrazin-2-yl]-pyridin-3-yl-methanone,

1-{3-[5-Amino-6-(pyridine-3-carbonyl)-pyrazin-2-yl]-phenyl}-ethanone,

[3-amino-6-(5-triflouoromethyl-pyridin-3-yl)-pyrazin-2-yl]-pyridin-3-yl-methanone,

[3-Amino-6-(3-furan-2-yl-phenyl-pyrazin-2-yl]-pyridin-3-yl-methanone,

5-[5-Amino-6-(pyridine-3-carbonyl)-pyrazine-2-yl]-2-chloro-N,N-dimethyl-benzamide,

[3-Amino-6-(2-chloro-pyridin-4-yl)-pyrazin-2-yl]-pyridin-3-yl-methanone,

3-[5-Amino-6-(pyridine-3-carbonyl)-pyrazin-2-yl]-N-benzyl-4-methyl-benzene sulphonamide,

[3-Amino-6-(1-benzyl-1H-pyrazol-4-yl)-pyrazin-2-yl]-pyrdin-3-yl-methanone,

3-[5-Amino-6-(pyridine-3-carbonyl)-pyrazin-2-yl]-4-fluoro-N-methyl-benzamide,

[3-Amino-6-(6-hydroxy-pyridin-3-yl)-pyrazin-2-yl]-pyridin-3-yl-methanone,

{3-Amino-6-[5-morpholine-4-carbonyl)-pyridin-3-yl]-pyrazin-2-yl}-pyridin-3-yl-methanone,

[3-Amino-6-(3-pyrazol-1yl-phenyl)-pyrazin-2-yl]-pyridin-3-yl-methanone,

[3-Amino-6-(3-morpholin-4-yl-phenyl)-pyrazin-2-yl]-pyridin-3-yl-methanone,

[3-Amino-6-(4-methoxy-pyridin-3-yl)-pyrazin-2-yl]-pyridin-3-yl-methanone,

[3-Amino-6-(2-methoxy-pyridin-4-yl)-pyrazin-2-yl]-pyridin-3-yl-methanone,

N-{3-[5-Amino-6-(pyridine-3-carbonyl)-pyrazin-2-yl]-benzyl}-methansulfonamide,

[3-Amino-6-(1H-pyrazol-4-yl)-pyrazin-2-yl]-pyridin-3-yl-methanone, (3-Amino-6-benzo[1,3]dioxol-5-yl-pyrazin-2-yl)-pyridin-3-yl-methanone,

[3-Amino-6-(2-trifluoromethoxy-phenyl)-pyrazin-2-yl]-pyridin-3-yl-methanone,

{3-Amino-6-[3-morpholine-4-carbonyl)-phenyl]-pyrazin-2-yl}-pyridin-3-yl-methanone, {3-Amino-6-[4-fluoro-3-(morpholine-4-carbonyl)-phenyl]-pyrazin-2-yl}-pyridin-3-yl-methanone, 3-[5-Amino-6-(pyridine-3-carbonyl)-pyrazin-2-yl]-4-fluoro-N-isopropyl-benzamide, {3-Amino-6-[2-methyl-5-(morpholine-4-sulfonyl)-phenyl]-pyrazin-2-yl}-(4-chloro-phenyl)-methanone, {3-Amino-5-methyl-6-[2-methyl-5-(morpholine-4-sulfonyl)-phenyl]-pyrazin-2-yl}-phenyl-methanone, {3-Amino-6-[2-methyl-5-(morpholine-4-sulfonyl)-phenyl]-pyrazin-2-yl}-phenyl-methanone, 3-(5-Amino-6-benzoyl-pyrazin-2-yl)-N-cyclopropyl-benzenesulfonamide, {3-Amino-6-[2-methyl-5-(morpholine-4-sulfonyl)-phenyl]-pyrazin-2-yl}-(3,5-difluoro-phenyl)-methanone, {3-Amino-6-[3-(morpholine-4-sulfonyl)-phenyl]-pyrazin-2-yl}-(4-fluoro-phenyl)-methanone,

[3-Amino-6-(1H-indol-5-yl)-pyrazin-2-yl]-pyridin-3-yl-methanone,

[3-Amino-6-(6-amino-pyridin-3-yl)-pyrazin-2-yl]-pyridin-3-yl-methanone,

3-[5-Amino-6-(pyridine-3-carbonyl)-pyrazin-2-yl]-benzoic acid,

3-[5-Amino-6-(pyridine-3-carbonyl)-pyrazin-2-yl]-benzaldehyde,

[3-Amino-6-(3-amino-phenyl)-pyrazin-2-yl]-pyridin-3-yl-methanone,

[3-Amino-6-(1H-indol-6-yl)-pyrazin-2-yl]-pyridin-3-yl-methanone,
N-{3-[5-Amino-6-(-trifluoromethylpyridine-3-carbonyl)pyrazin-2-yl]phenyl}acetamide,
3-[5-Amino-6-(pyridine-3-carbonyl)-pyrazin-2-yl]-N-(2-methoxy-ethyl)-benzenesulfonamide,
5-[5-Amino-6-(pyridine-3-carbonyl)-pyrazin-2-yl]-2-chloro-N-(4-hydroxy-cyclohexyl)-benzene sulfonamide,
{3-Amino-6-[3-(morpholine-4-sulfonyl)-4-trifluoromethyl-phenyl]-pyrazin-2-yl}-pyridin-3-yl-methanone,
5-[5-Amino-6-(pyridine-3-carbonyl)-pyrazin-2-yl-N-cyclopropyl-2,4-difluoro-benzenesulfonamide,
1-{6-[5-Amino-6-(pyridine-3-carbonyl)-pyrazin-2-yl]-2,3-dihydro-indol-1-yl}-ethanone,
6-[5-Amino-6-(pyridine-3-carbonyl)-pyrazin-2-yl]-1,3-dihydro-indol-2-one,
{3-Amino-6-[3-(4-methyl-piperazine-1-sulfonyl)-5-trifluoromethyl-phenyl]-pyrazin-2-yl}-pyridin-3-yl-methanone,
6-[5-Amino-6-(pyridine-3-carbonyl)-pyrazin-2-yl]-4H-benzo[1,4]oxazin-3-one,
[3-Amino-6-(1H-indol-4-yl)-pyrazin-2-yl]-pyridin-3-yl-methanone,
3-[5-Amino-6-(pyridine-3-carbonyl)-pyrazin-2-yl]-5-trifluoromethyl-benzenesulfonamide,
{3-Amino-6-[3-(4-methyl-piperazine-1-sulfonyl)-4-trifluoromethyl-phenyl]-pyrazin-2-yl}-pyridin-3-yl-methanone,
{3-Amino-6-[5-morpholine-4-sulfonyl)-pyridin-3-yl]-pyrazin-2-yl}-pyridin-3-yl-methanone,
{3-Amino-6-[2,4-difluoro-5-(4-methyl-piperazine-1-sulfonyl)-phenyl]-pyrazin-2-yl}-pyridin-3-yl-methanone,
{3-Amino-6-[–4-chloro-3-(4-methyl-piperazine-1-sulfonyl)-phenyl]-pyrazin-2-yl}-pyridin-3-yl-methanone,
{3-Amino-6-[3-(4-cyclopropyl-piperazine-1-sulfonlyl)-phenyl]-pyrazin-2-yl}-pyridin-3-yl-methanone,
{3-Amino-6-[3-(4-methyl-[1,4]diazepane-1-sulfonyl)-phenyl]-pyrazin-2-yl}pyridine-3-yl-methanone,
{3-Amino-6-[2,4-difluoro-5-(morpholine-4-sulfonyl)-phenyl]-pyrazin-2-yl}-pyridin-3-yl-methanone,
(3-Amino-6-{3-[4-(2-hydroxy-ethyl)-piperazine-1-sulfonyl]-phenyl}-pyrazin-2-yl)-pyridin-3-yl-methanone,
3-[5-Amino-6-(pyridine-3-carbonyl)-pyrazin-2-yl]-N-[2-(4-methyl-piperazin-1-yl)-ethyl]-benzenesulfonamide,
3-[5-Amino-6-(pyridine-3-carbonyl)-pyrazin-2-yl]-N-cyclobutyl-benzenesuflonamide,
{3-Amino-6-[3-(4-methyl-piperazine-1-sulfonyl)-phenyl]-pyrazin-2-yl}-pyridin-3-yl-methanone,
5-[5-Amino-6-(pyridine-3-carbonyl)-pyrazin-2-yl]-2-chloro-N-cyclopropyl-benzenesuflonamide,
{3-Amino-6-[4-chloro-3-(morpholine-4-sulfonyl)-phenyl]-pyrazin-2-yl}-pyridin-3-yl-methanone,
3-[5-Amino-6-(pyridine-3-carbonyl)-pyrazin-2-yl]-N-cyclopropylmethyl-benzenesulfonamide,
{3-Amino-6-[3-(4-methyl-piperazine-1-sulfonyl)-phenyl]-pyrazin-2-yl}-(4-chloro-phenyl)-methanone,
{3-amino-6-[4-chloro-3-(4-methyl-piperazine-1-sulfonyl)-phenyl]-pyrazin-2-yl}-(4-chloro-phenyl)-methanone,
{3-Amino-6-[4-chloro-3-(4-isopropyl-piperazine-1-sulfonyl)-phenyl]-pyrazin-2-yl}-(4-chloro-phenyl)-methanone,
3-[5-Amino-6-(4-fluoro-benzoyl)-pyrazin-2-yl]-N-(2-methoxy-ethyl)-benzenesulfonamide,
[3-Amino-6-(3,4-dichloro-phenyl)-pyrazin-2-yl]-(4-piperidin-1-ylmethyl-phenyl)-methanone,
{3-Amino-6-[2-methyl-5-(morpholine-4-sulfonyl)-phenyl]-pyrazin-2-yl}-cyclopropyl-methanone,
5-[5-Amino-6-(pyridine-3-carbonyl)-pyrazin-2-yl]-N-cyclopropylmethyl-2,4-difluoro-benzenesulfonamide,
5-[5-Amino-6-(pyridine-3-carbonyl)-pyrazin-2-yl]-2,4-difluoro-N-(2-methoxy-ethyl)-benzenesulfonamide,
5-[5-Amino-6-(pyridine-3-carbonyl)-pyrazin-2-yl]-N-(2-methoxy-ethyl)-2-trifluoromethyl-benzenesulfonamide,
5-[5-Amino-6-(pyridine-3-carbonyl)-pyrazin-2-yl]-2,4-difluoro-N-(4-hydroxy-cyclohexyl)-benzenesulfonamide,
5-(5-Amino-6-cyclopropanecarbonyl-pyrazin-2-yl)-2,4-difluoro-N-(4-hydroxy-cyclohexyl)-benzenesulfonamide,
3-(5-Amino-6-cyclopropanecarbonyl-pyrazin-2-yl)-N-(2-methoxy-ethyl)-benzenesulfonamide,
{3-Amino-6-[3-(morpholine-4-sulfonyl)-phenyl]-pyrazin-2-yl}-pyridin-3-yl-methanone,
5-[5-Amino-6-(pyridine-3-carbonyl)-pyrazin-2-yl]-2-chloro-N-(2-methoxy-ethyl)-benzenesulfonamide, and
N-{3-[5-Amino-6-(pyridine-3-carbonyyl)-pyrazin-2-yl]-phenyl}-methanesulfonamide,
[3-Amino-6-(5-amino-2-methyl-phenyl)-pyrazin-2-yl]-methanone, and
N-{3-[5-Amino-6-(pyridine-3-carbonyl)-pyrazin-2-yl]-4-methyl-phenyl}-acetamide or
pharmaceutically acceptable salts thereof.

6. A pharmaceutical composition, comprising a compound selected from the group consisting of:
[3-Amino-6-(6-amino-5-trifluoromethyl-pyridin-3-yl)-pyrazin-2-yl]-pyridin-3-yl-methanone,
{3-Amino-6-[2-methyl-5-(morpholine-4-sulfonyl)-phenyl]pyrazin-2-yl}-pyridin-3-yl-methanone,
N-{5-[5-Amino-6-(pyridine-3-carbonyl)-pyrazin-2-yl]-2-chloro-pyridin-3-yl}-benzenesulfonamide,
[3-Amino-6-(3-methanesulfonyl-phenyl)-pyrazin-2-yl]-pyridin-3-yl-methanone,
{3-Amino-6-[3-(pyrrolidine-1-sulfonyl)-phenyl]-pyrazin-2-yl}-pyridin-3-yl-methanone,
[3-Amino-6-(4-chloro-3-methyl-phenyl)-pyrazin-2-yl]-pyridin-3-yl-methanone,
N'-{3-[5-amino-6-(pyridine-3-carbonyl)-pyrazin-2-yl]-phenyl}-N,N-dimethyl-sulfamide,
[3-Amino-6-(5-methanesulfonyl-pyridin-3-yl)-pyrazin-2-yl]-pyridin-3-yl-methanone,
[3-Amino-6-(3-chloro-5-methyl-phenyl)-pyrazin-2-yl]-pyridin-3-yl-methanone,
3-[5-Amino-6-(pyridine-3-carbonyl)-pyrazin-2-yl]-N-cyclopropyl-benzenesulfonamide,
[3-Amino-6-(3,4-dichloro-phenyl)pyrazin-2-yl]-pyridin-3-yl-methanone,
Cyclopropanesulfonic acid {3-[5-amino-6-(pyridine-3-carbonyl)-pyrazin-2-yl]-4-methyl-phenyl}-amide,
5-[5-Amino-6-(pyridine-3-carbonyl)-pyrazin-2-yl]-2-chloro-N-phenyl-benzenesulfonamide,
[3-Amino-6-(4-chloro-3-trifluoromethyl-phenyl)-pyrazin-2-yl]-pyridin-3-yl-methanone,
[3-Amino-6-(3-chloro-phenyl)-pyrazin-2-yl]-pyridin-3-yl-methanone,
[3-Amino-6-(3-amino-4-chloro-phenyl)-pyrazin-2-yl]-pyridin-3-yl-methanone,
{3-Amino-6-[4-methoxy-3-morpholine-4-sulfonyl)-phenyl]-pyrazin-2-yl}-pyridin-3-yl-methanone,
[3-Amino-6-(6-chloro-pyridin-3-yl)-pyrazin-2-yl]-pyridin-3-yl-methanone, 1-{3-[5-Amino-6-(pyridine-3-carbonyl)-pyrazin-2-yl]-phenyl}-ethanone,
[3-amino-6-(5-triflouoromethyl-pyridin-3-yl)-pyrazin-2-yl]-pyridin-3-yl-methanone,
[3-Amino-6-(3-furan-2-yl-phenyl-pyrazin-2-yl]-pyridin-3-yl-methanone,
5-[5-Amino-6-(pyridine-3-carbonyl)-pyrazine-2-yl]-2-chloro-N,N-dimethyl-benzamide,
[3-Amino-6-(2-chloro-pyridin-4-yl)-pyrazin-2-yl]-pyridin-3-yl-methanone,
3-[5-Amino-6-(pyridine-3-carbonyl)-pyrazin-2-yl]-N-benzyl-4-methyl-benzene sulphonamide,
[3-Amino-6-(1-benzyl-1H-pyrazol-4-yl)-pyrazin-2-yl]-pyrdin-3-yl-methanone,
3-[5-Amino-6-(pyridine-3-carbonyl)-pyrazin-2-yl]-4-fluoro-N-methyl-benzamide,
[3-Amino-6-(6-hydroxy-pyridin-3-yl)-pyrazin-2-yl]-pyridin-3-yl-methanone,
{3-Amino-6-[5-morpholine-4-carbonyl)-pyridin-3-yl]-pyrazin-2-yl}-pyridin-3-yl-methanone,
[3-Amino-6-(3-pyrazol-1yl-phenyl)-pyrazin-2-yl]-pyridin-3-yl-methanone,
[3-Amino-6-(3-morpholin-4-yl-phenyl)-pyrazin-2-yl]-pyridin-3-yl-methanone,
[3-Amino-6-(4-methoxy-pyridin-3-yl)-pyrazin-2-yl]-pyridin-3-yl-methanone,
[3-Amino-6-(2-methoxy-pyridin-4-yl)-pyrazin-2-yl]-pyridin-3-yl-methanone,
N-{3-[5-Amino-6-(pyridine-3-carbonyl)-pyrazin-2-yl]-benzyl}-methansulfonamide,
[3-Amino-6-(1H-pyrazol-4-yl)-pyrazin-2-yl]-pyridin-3-yl-methanone,
(3-Amino-6-benzo[1,3]dioxol-5-yl-pyrazin-2-yl)-pyridin-3-yl-methanone,
[3-Amino-6-(2-trifluoromethoxy-phenyl)-pyrazin-2-yl]-pyridin-3-yl-meth a none,
{3-Amino-6-[3-morpholine-4-carbonyl)-phenyl]-pyrazin-2-yl}-pyridin-3-yl-meth a none,
{3-Amino-6-[4-fluoro-3-(morpholine-4-carbonyl)-phenyl]-pyrazin-2-yl}-pyridin-3-yl-methanone,
3-[5-Amino-6-(pyridine-3-carbonyl)-pyrazin-2-yl]-4-fluoro-N-isopropyl-benzamide,
{3-Amino-6-[2-methyl-5-(morpholine-4-sulfonyl)-phenyl]-pyrazin-2-yl}-(4-chloro-phenyl)-methanone,
{3-Amino-5-methyl-6-[2-methyl-5-(morpholine-4-sulfonyl)-phenyl]-pyrazin-2-yl}-phenyl-methanone,
{3-Amino-6-[2-methyl-5-(morpholine-4-sulfonyl)-phenyl]-pyrazin-2-yl}-phenyl-methanone,
3-(5-Amino-6-benzoyl-pyrazin-2-yl)-N-cyclopropyl-benzenesulfonamide,
{3-Amino-6-[2-methyl-5-(morpholine-4-sulfonyl)-phenyl]-pyrazin-2-yl}-(3,5-difluoro-phenyl)-methanone,
{3-Amino-6-[3-(morpholine-4-sulfonyl)-phenyl]-pyrazin-2-yl}-(4-fluoro-phenyl)-methanone,
[3-Amino-6-(1H-indol-5-yl)-pyrazin-2-yl]-pyridin-3-yl-methanone,
[3-Amino-6-(6-amino-pyridin-3-yl)-pyrazin-2-yl]-pyridin-3-yl-methanone,
3-[5-Amino-6-(pyridine-3-carbonyl)-pyrazin-2-yl]-benzoic acid,
3-[5-Amino-6-(pyridine-3-carbonyl)-pyrazin-2-yl]-benzaldehyde,
[3-Amino-6-(3-amino-phenyl)-pyrazin-2-yl]-pyridin-3-yl-methanone,
[3-Amino-6-(1H-indol-6-yl)-pyrazin-2-yl]-pyridin-3-yl-methanone,
N-{3-[5-Amino-6-(-trifluoromethylpyridine-3-carbonyl)pyrazin-2-yl]phenyl}acetamide,
3-[5-Amino-6-(pyridine-3-carbonyl)-pyrazin-2-yl]-N-(2-methoxy-ethyl)-benzenesulfonamide,
5-[5-Amino-6-(pyridine-3-carbonyl)-pyrazin-2-yl]-2-chloro-N-(4-hydroxy-cyclohexyl)-benzene sulfonamide,
{3-Amino-6-[3-(morpholine-4-sulfonyl)-4-trifluoromethyl-phenyl]-pyrazin-2-yl}-pyridin-3-yl-methanone,
5-[5-Amino-6-(pyridine-3-carbonyl)-pyrazin-2-yl-N-cyclopropyl-2,4-difluoro-benzenesulfonamide,
1-{6-[5-Amino-6-(pyridine-3-carbonyl)-pyrazin-2-yl]-2,3-dihydro-indol-1-yl}-ethanone,
6-[5-Amino-6-(pyridine-3-carbonyl)-pyrazin-2-yl]-1,3-dihydro-indol-2-one,
{3-Amino-6-[3-(4-methyl-piperazine-1-sulfonyl)-5-trifluoromethyl-phenyl]-pyrazin-2-yl}-pyridin-3-yl-methanone,
6-[5-Amino-6-(pyridine-3-carbonyl)-pyrazin-2-yl]-4H-benzo[1,4]oxazin-3-one,
[3-Amino-6-(1H-indol-4-yl)-pyrazin-2-yl]-pyridin-3-yl-methanone,
3-[5-Amino-6-(pyridine-3-carbonyl)-pyrazin-2-yl]-5-trifluoromethyl-benzenesulfonamide,
{3-Amino-6-[3-(4-methyl-piperazine-1-sulfonyl)-4-trifluoromethyl-phenyl]-pyrazin-2-yl}-pyridin-3-yl-methanone,
{3-Amino-6-[5-morpholine-4-sulfonyl)-pyridin-3-yl]-pyrazin-2-yl}-pyridin-3-yl-methanone,
{3-Amino-6-[2,4-difluoro-5-(4-methyl-piperazine-1-sulfonyl)-phenyl]-pyrazin-2-yl}-pyridin-3-yl-methanone,
{3-Amino-6-[4-chloro-3-(4-methyl-piperazine-1-sulfonyl)-phenyl]-pyrazin-2-yl}-pyridin-3-yl-methanone,
{3-Amino-6-[3-(4-cyclopropyl-piperazine-1-sulfonlyl)-phenyl]-pyrazin-2-yl}-pyridin-3-yl-methanone,
{3-Amino-6-[3-(4-methyl-[1,4]diazepane-1-sulfonyl)-phenyl]-pyrazin-2-yl}pyridine-3-yl-methanone,
{3-Amino-6-[2,4-difluoro-5-(morpholine-4-sulfonyl)-phenyl]-pyrazin-2-yl}-pyridin-3-yl-methanone,
(3-Amino-6-{3-[4-(2-hydroxy-ethyl)-piperazine-1-sulfonyl]-phenyl}-pyrazin-2-yl)-pyridin-3-yl-methanone,
3-[5-Amino-6-(pyridine-3-carbonyl)-pyrazin-2-yl]-N-[2-(4-methyl-piperazin-1-yl)-ethyl]-benzenesulfonamide,
3-[5-Amino-6-(pyridine-3-carbonyl)-pyrazin-2-yl]-N-cyclobutyl-benzenesufonamide,
{3-Amino-6-[3-(4-methyl-piperazine-1-sulfonyl)-phenyl]-pyrazin-2-yl}-pyridin-3-yl-methanone,
5-[5-Amino-6-(pyridine-3-carbonyl)-pyrazin-2-yl]-2-chloro-N-cyclopropyl-benzenesufonamide,
{3-Amino-6-[4-chloro-3-(morpholine-4-sulfonyl)-phenyl]-pyrazin-2-yl}-pyridin-3-yl-methanone,
3-[5-Amino-6-(pyridine-3-carbonyl)-pyrazin-2-yl]-N-cyclopropylmethyl-benzenesulfonamide,
{3-Amino-6-[3-(4-methyl-piperazine-1-sulfonyl)-phenyl]-pyrazin-2-yl}-(4-chloro-phenyl)-methanone,
{3-amino-6-[4-chloro-3-(4-methyl-piperazine-1-sulfonyl)-phenyl]-pyrazin-2-yl}-(4-chloro-phenyl)-methanone,
{3-Amino-6-[4-chloro-3-(4-isopropyl-piperazine-1-sulfonyl)-phenyl]-pyrazin-2-yl}-(4-chloro-phenyl)-methanone,
3-[5-Amino-6-(4-fluoro-benzoyl)-pyrazin-2-yl]-N-(2-methoxy-ethyl)-benzenesulfonamide,
[3-Amino-6-(3,4-dichloro-phenyl)-pyrazin-2-yl]-(4-piperidin-1-ylmethyl-phenyl)-methanone, {3-Amino-6-[2-methyl-5-(morpholine-4-sulfonyl)-phenyl]-pyrazin-2-yl}-cyclopropyl-methanone, 5-[5-Amino-6-(pyridine-3-carbonyl)-pyrazin-2-yl]-N-cyclopropylmethyl-2,4-difluoro-benzenesulfonamide, 5-[5-Amino-6-(pyridine-3-carbonyl)-pyrazin-2-yl]-2,4-difluoro-N-(2-methoxy-ethyl)-benzenesulfonamide, 5-[5-Amino-6-(pyridine-3-carbonyl)-pyrazin-2-yl]-N-(2-methoxy-ethyl)-2-trifluoromethyl-benzenesulfonamide, 5-[5-Amino-6-(pyridine-3-carbonyl)-pyrazin-2-yl]-2,4-difluoro-N-(4-hydroxy-cyclohexyl)-benzenesulfonamide, 5-(5-Amino-6-cyclopropanecarbonyl-pyrazin-2-yl)-2,4-difluoro-N-(4-hydroxy-cyclohexyl)-benzenesulfonamide, 3-(5-Amino-6-cyclopropanecarbonyl-pyrazin-2-yl)-N-(2-methoxy-ethyl)-benzenesulfonamide, {3-Amino-6-[3-(morpholine-4-sulfonyl)-phenyl]-pyrazin-2-yl}-pyridin-3-yl-methanone, 5-[5-Amino-6-(pyridine-3-carbonyl)-pyrazin-2-yl]-2-chloro-N-(2-methoxy-ethyl)-benzenesulfonamide, and N-{3-[5-Amino-6-(pyridine-3-carbonyyl)-pyrazin-2-yl]-phenyl}-methanesulfonamide,

[3-Amino-6-(5-amino-2-methyl-phenyl)-pyrazin-2-yl-methanone, and

N-{3-[5-Amino-6-(pyridine-3-carbonyl)-pyrazin-2-yl]-4-methyl-phenyl}-acetamide;

or a pharmaceutically acceptable salt thereof, and a pharmaceutically acceptable excipient.

\* \* \* \* \*